(12) United States Patent
Jacobi

(10) Patent No.: US 11,885,790 B2
(45) Date of Patent: Jan. 30, 2024

(54) SOURCE PRODUCTIVITY ASSAY INTEGRATING PYROLYSIS DATA AND X-RAY DIFFRACTION DATA

(71) Applicant: Saudi Arabian Oil Company, Dhahran (SA)

(72) Inventor: David Jacobi, Houston, TX (US)

(73) Assignee: Saudi Arabian Oil Company, Dhahran (SA)

( * ) Notice: Subject to any disclaimer, the term of this patent is extended or adjusted under 35 U.S.C. 154(b) by 43 days.

(21) Appl. No.: 17/549,267

(22) Filed: Dec. 13, 2021

(65) Prior Publication Data

US 2023/0184737 A1 Jun. 15, 2023

(51) Int. Cl.
*G01N 33/24* (2006.01)
*G01N 23/207* (2018.01)

(52) U.S. Cl.
CPC ......... *G01N 33/241* (2013.01); *G01N 23/207* (2013.01); *G01N 2223/304* (2013.01); *G01N 2223/616* (2013.01)

(58) Field of Classification Search
CPC ............... G01N 33/241; G01N 23/207; G01N 2223/304; G01N 2223/616
See application file for complete search history.

(56) References Cited

U.S. PATENT DOCUMENTS

| | | |
|---|---|---|
| 2,900,269 A | 8/1959 | Bauman et al. |
| 2,904,445 A | 9/1959 | Sellers |
| 3,072,502 A | 1/1963 | Salvatore |
| 3,284,281 A | 11/1966 | Thomas |
| 3,456,183 A | 7/1969 | Codrington et al. |
| 3,616,855 A | 11/1971 | Colgate |
| 3,716,387 A | 2/1973 | Simmons et al. |
| 3,807,557 A | 4/1974 | Miller |
| 3,834,122 A | 9/1974 | Allison et al. |
| 3,912,330 A | 10/1975 | Carnahan et al. |
| 3,926,575 A | 12/1975 | Meyers |
| 3,996,062 A | 12/1976 | Frost |
| 4,043,599 A | 8/1977 | Lingane |
| 4,043,885 A | 8/1977 | Yen et al. |
| 4,220,550 A | 9/1980 | Frenier et al. |
| 4,223,726 A | 9/1980 | Cha |
| 4,252,189 A | 2/1981 | Bodine |
| 4,289,639 A | 9/1981 | Buske |
| 4,324,560 A | 4/1982 | Fonseca |
| 4,381,950 A | 5/1983 | Lawson |
| 4,444,058 A | 4/1984 | Ratigan |
| 4,485,071 A | 11/1984 | Larter |

(Continued)

FOREIGN PATENT DOCUMENTS

| | | |
|---|---|---|
| CN | 87213495 | 6/1988 |
| CN | 101916522 | 12/2010 |

(Continued)

OTHER PUBLICATIONS

U.S. Appl. No. 17/107,428, filed Nov. 30, 2020, Hull et al.

(Continued)

*Primary Examiner* — Michael J Dalbo
*Assistant Examiner* — Kaleria Knox
(74) *Attorney, Agent, or Firm* — Fish & Richardson P.C.

(57) ABSTRACT

The disclosure relates to a source productivity assay integrating pyrolysis data and X-ray diffraction data.

17 Claims, 30 Drawing Sheets

(56) References Cited

U.S. PATENT DOCUMENTS

| | | |
|---|---|---|
| 4,587,739 A | 5/1986 | Holcomb |
| 4,589,490 A | 5/1986 | Darr et al. |
| 4,594,170 A | 6/1986 | Brown et al. |
| 4,640,692 A | 2/1987 | Audeh |
| 4,882,128 A | 11/1989 | Hukvari et al. |
| 4,959,401 A | 9/1990 | Bellasalma et al. |
| 5,180,556 A | 1/1993 | Nolte et al. |
| 5,193,396 A | 3/1993 | Gorski |
| 5,224,543 A | 7/1993 | Watkins |
| 5,232,490 A | 8/1993 | Bender et al. |
| 5,302,297 A | 4/1994 | Barthrope |
| 5,390,529 A | 2/1995 | Ghiselli |
| 5,435,187 A | 7/1995 | Ewy |
| 5,441,343 A | 8/1995 | Pylkki et al. |
| 5,757,473 A | 5/1998 | Kanduth et al. |
| 5,759,964 A | 6/1998 | Shuchart |
| 5,869,750 A | 2/1999 | Onan |
| 5,905,657 A | 5/1999 | Celniker |
| 5,999,887 A | 12/1999 | Giannakopoulos et al. |
| 6,095,679 A | 8/2000 | Hammiche et al. |
| 6,138,760 A | 10/2000 | Lopez et al. |
| 6,411,902 B1 | 6/2002 | Wiltshire |
| 6,488,091 B1 | 12/2002 | Weaver |
| 6,491,425 B1 | 12/2002 | Hammiche et al. |
| 6,494,263 B2 | 12/2002 | Todd |
| 6,516,080 B1 | 2/2003 | Nur |
| 6,590,647 B2 | 7/2003 | Stephenson |
| 6,749,022 B1 | 6/2004 | Fredd |
| 6,866,048 B2 | 3/2005 | Mattox |
| 6,942,840 B1 | 9/2005 | Broderick |
| 6,947,843 B2 | 9/2005 | Fisher et al. |
| 6,989,391 B2 | 1/2006 | Funkhouser |
| 7,077,199 B2 | 7/2006 | Vinegar et al. |
| 7,086,484 B2 | 8/2006 | Smith |
| 7,098,663 B1 | 8/2006 | Bader |
| 7,344,889 B2 | 3/2008 | Kelemen et al. |
| 7,369,980 B2 | 5/2008 | Deffenbaugh et al. |
| 7,526,418 B2 | 4/2009 | Pita et al. |
| 7,565,831 B2 | 7/2009 | Miyahara |
| 7,588,827 B2 | 9/2009 | Nie et al. |
| 7,706,981 B2 | 4/2010 | Wilkinson et al. |
| 7,770,647 B2 | 8/2010 | Watson et al. |
| 7,879,625 B1 | 2/2011 | Boss |
| 7,983,845 B2 | 7/2011 | Minh |
| 8,165,817 B2 | 4/2012 | Betancourt et al. |
| 8,177,422 B2 | 5/2012 | Kjoller et al. |
| 8,225,866 B2 | 7/2012 | Rouffignac et al. |
| 8,278,931 B2 | 10/2012 | Fang et al. |
| 8,337,783 B2 | 12/2012 | Locascio et al. |
| 8,352,228 B2 | 1/2013 | Walters et al. |
| 8,380,437 B2 | 2/2013 | Abousleiman et al. |
| 8,473,213 B2 | 6/2013 | Zhu et al. |
| 8,701,788 B2 | 4/2014 | Wigand et al. |
| 8,729,903 B2 | 5/2014 | Srnka et al. |
| 8,821,806 B2 | 9/2014 | Hersherwitz et al. |
| 8,839,860 B2 | 9/2014 | Wigand et al. |
| 8,851,177 B2 | 10/2014 | Wigand |
| 8,865,482 B2 | 10/2014 | Wang et al. |
| 8,868,385 B2 | 10/2014 | Fertig et al. |
| 8,899,331 B2 | 12/2014 | Burnham |
| 8,936,089 B2 | 1/2015 | Wigand |
| 9,033,033 B2 | 5/2015 | Thomas et al. |
| 9,057,797 B2 | 6/2015 | Omeragic et al. |
| 9,128,210 B2 | 9/2015 | Pomerantz |
| 9,152,745 B2 | 10/2015 | Glinsky |
| 9,244,182 B2 | 1/2016 | Loseth et al. |
| 9,552,462 B2 | 1/2017 | Walters et al. |
| 9,696,270 B1 | 7/2017 | Roy et al. |
| 9,784,882 B2 | 10/2017 | Vinegar et al. |
| 9,834,721 B2 | 12/2017 | Chang et al. |
| 9,863,231 B2 | 1/2018 | Hull et al. |
| 9,869,649 B2 | 1/2018 | Hull et al. |
| 10,260,319 B2 | 4/2019 | Sarduy et al. |
| 10,329,478 B2 | 6/2019 | Schnoor et al. |
| 10,351,758 B2 | 7/2019 | Hull et al. |
| 10,472,555 B2 | 11/2019 | Hutchins et al. |
| 10,479,927 B2 | 11/2019 | Hull et al. |
| 10,611,967 B2 | 4/2020 | Inan |
| 10,619,469 B2 | 4/2020 | Han et al. |
| 10,753,190 B1 | 8/2020 | Schipper et al. |
| 10,871,060 B2 | 12/2020 | Han et al. |
| 10,871,061 B2 | 12/2020 | Hull et al. |
| 10,900,339 B2 | 1/2021 | Schipper et al. |
| 11,078,406 B2 | 8/2021 | Hull et al. |
| 11,150,206 B2 | 10/2021 | Eichmann et al. |
| 11,186,806 B2 | 11/2021 | Hull |
| 11,236,020 B2 | 2/2022 | Haque et al. |
| 11,268,919 B2 | 3/2022 | Eichmann et al. |
| 2004/0101457 A1 | 5/2004 | Pahlman et al. |
| 2005/0060130 A1 | 3/2005 | Shapiro et al. |
| 2005/0103118 A1 | 5/2005 | Workman |
| 2006/0047489 A1 | 3/2006 | Scheidt et al. |
| 2006/0092766 A1 | 5/2006 | Shelley et al. |
| 2006/0265204 A1 | 11/2006 | Wallis et al. |
| 2007/0203677 A1 | 8/2007 | Awwiller |
| 2007/0246649 A1 | 10/2007 | Jacobi et al. |
| 2007/0298979 A1 | 12/2007 | Perry et al. |
| 2008/0006410 A1 | 1/2008 | Looney et al. |
| 2008/0059140 A1 | 3/2008 | Salmon et al. |
| 2008/0070806 A1 | 3/2008 | Lin et al. |
| 2008/0110253 A1 | 5/2008 | Stephenson et al. |
| 2008/0111064 A1 | 5/2008 | Andrews et al. |
| 2009/0044945 A1 | 2/2009 | Wilberg et al. |
| 2009/0071239 A1 | 3/2009 | Rojas et al. |
| 2009/0087912 A1 | 4/2009 | Ramos et al. |
| 2009/0143252 A1 | 6/2009 | Lehmann |
| 2009/0145607 A1 | 6/2009 | Li et al. |
| 2009/0193881 A1 | 8/2009 | Finnberg |
| 2009/0203557 A1 | 8/2009 | Barnes et al. |
| 2009/0248309 A1 | 10/2009 | Nelville et al. |
| 2009/0313772 A1 | 12/2009 | Talley |
| 2010/0010106 A1 | 1/2010 | Crews |
| 2010/0049625 A1 | 2/2010 | Biebesheimer et al. |
| 2010/0051511 A1 | 3/2010 | Faerman |
| 2010/0092865 A1 | 4/2010 | Kanno et al. |
| 2010/0186520 A1 | 7/2010 | Wheeler |
| 2010/0213579 A1 | 8/2010 | Henry |
| 2010/0224365 A1 | 9/2010 | Abad |
| 2010/0224823 A1 | 9/2010 | Yin et al. |
| 2010/0258265 A1 | 10/2010 | Karanikas et al. |
| 2010/0276142 A1 | 11/2010 | Skildum et al. |
| 2010/0279136 A1 | 11/2010 | Bonucci |
| 2010/0323933 A1 | 12/2010 | Fuller et al. |
| 2011/0065612 A1 | 3/2011 | Stokes et al. |
| 2011/0207231 A1 | 8/2011 | Natan et al. |
| 2011/0257944 A1 | 10/2011 | Du et al. |
| 2011/0259588 A1 | 10/2011 | Ali et al. |
| 2011/0260051 A1 | 10/2011 | Preudhomme et al. |
| 2011/0275061 A1 | 11/2011 | Weidemaier et al. |
| 2012/0026037 A1 | 2/2012 | Thomson et al. |
| 2012/0179444 A1 | 7/2012 | Ganguly et al. |
| 2012/0193578 A1 | 8/2012 | Pan et al. |
| 2012/0247774 A1 | 10/2012 | Li et al. |
| 2012/0257199 A1 | 10/2012 | Liu et al. |
| 2012/0261617 A1 | 10/2012 | Pan et al. |
| 2013/0013209 A1 | 1/2013 | Zhu et al. |
| 2013/0040292 A1 | 2/2013 | Lopez et al. |
| 2013/0056213 A1 | 3/2013 | Medvedev et al. |
| 2013/0084643 A1 | 4/2013 | Commarieu et al. |
| 2013/0160994 A1 | 6/2013 | Alsop et al. |
| 2013/0161002 A1 | 6/2013 | Wigand |
| 2013/0213120 A1 | 8/2013 | Lebedev |
| 2013/0228019 A1 | 9/2013 | Meadows |
| 2013/0231908 A1 | 9/2013 | Williams et al. |
| 2013/0233536 A1 | 9/2013 | Alqam |
| 2013/0238304 A1 | 9/2013 | Glinsky |
| 2013/0259808 A1 | 10/2013 | Chen et al. |
| 2013/0264121 A1 | 10/2013 | Young |
| 2013/0269933 A1 | 10/2013 | Pomerantz et al. |
| 2013/0310492 A1 | 11/2013 | Morgan |
| 2013/0341028 A1 | 12/2013 | Christian et al. |
| 2014/0008305 A1 | 1/2014 | Nichols et al. |
| 2014/0045732 A1 | 2/2014 | Mazyar |
| 2014/0048694 A1 | 2/2014 | Pomerantz |

(56) References Cited

U.S. PATENT DOCUMENTS

| | | | |
|---|---|---|---|
| 2014/0067351 | A1 | 3/2014 | Gray et al. |
| 2014/0077121 | A1 | 3/2014 | Sun et al. |
| 2014/0116710 | A1 | 5/2014 | Naser-El-Din et al. |
| 2014/0186939 | A1 | 7/2014 | Peterman et al. |
| 2014/0231077 | A1 | 8/2014 | Rivero et al. |
| 2014/0251605 | A1 | 9/2014 | Hera |
| 2014/0260694 | A1 | 9/2014 | Szlendak |
| 2014/0271321 | A1 | 9/2014 | Maderud |
| 2014/0360973 | A1 | 12/2014 | Yin et al. |
| 2014/0374104 | A1 | 12/2014 | Kushal |
| 2015/0019183 | A1 | 1/2015 | Suzuki |
| 2015/0038347 | A1 | 2/2015 | Johnson et al. |
| 2015/0075782 | A1 | 3/2015 | Sharma |
| 2015/0079270 | A1 | 3/2015 | Wang et al. |
| 2015/0152724 | A1 | 6/2015 | Amendt |
| 2015/0233214 | A1 | 8/2015 | Dusterhoft et al. |
| 2015/0293256 | A1 | 10/2015 | Dusterhoft |
| 2015/0300140 | A1 | 10/2015 | Eoff et al. |
| 2016/0017202 | A1 | 1/2016 | Yang et al. |
| 2016/0061017 | A1 | 3/2016 | Nguyen et al. |
| 2016/0103047 | A1 | 4/2016 | Liu |
| 2016/0103049 | A1 | 4/2016 | Liu |
| 2016/0265331 | A1 | 9/2016 | Weng et al. |
| 2016/0289543 | A1 | 10/2016 | Chang et al. |
| 2016/0362965 | A1 | 12/2016 | Parlar |
| 2017/0066959 | A1 | 3/2017 | Hull et al. |
| 2017/0067836 | A1 | 3/2017 | Hull et al. |
| 2017/0235016 | A1 | 8/2017 | Prioul et al. |
| 2017/0336528 | A1 | 11/2017 | Badri et al. |
| 2017/0370197 | A1 | 12/2017 | Han et al. |
| 2018/0112126 | A1 | 4/2018 | Yang et al. |
| 2019/0003298 | A1* | 1/2019 | Stolyarov ............... E21B 47/18 |
| 2019/0118265 | A1 | 4/2019 | Nie et al. |
| 2019/0211658 | A1 | 7/2019 | Hull et al. |
| 2020/0340342 | A1 | 10/2020 | Schipper et al. |
| 2021/0024808 | A1 | 1/2021 | Schipper et al. |
| 2021/0024814 | A1 | 1/2021 | Schipper et al. |
| 2021/0080413 | A1 | 3/2021 | Eichmann et al. |
| 2021/0080414 | A1 | 3/2021 | Eichmann et al. |
| 2021/0087915 | A1 | 3/2021 | Han et al. |
| 2021/0198558 | A1 | 7/2021 | Hull et al. |
| 2021/0198559 | A1 | 7/2021 | Hull et al. |
| 2021/0222055 | A1 | 7/2021 | Schipper et al. |
| 2021/0310966 | A1 | 10/2021 | Soua |

FOREIGN PATENT DOCUMENTS

| | | | |
|---|---|---|---|
| CN | 102015959 | | 4/2011 |
| CN | 102220116 | | 10/2011 |
| CN | 101819111 | | 12/2011 |
| CN | 1621803 | | 5/2012 |
| CN | 102183410 | | 5/2014 |
| CN | 105219948 | | 1/2016 |
| CN | 105445440 | | 3/2016 |
| CN | 106525898 | | 3/2017 |
| CN | 113702088 A * | | 11/2021 ............... G01N 1/32 |
| EP | 0247669 | | 12/1987 |
| EP | 2040075 | | 3/2009 |
| EP | 2480625 | | 4/2013 |
| EP | 2480626 | | 4/2013 |
| GB | 2161269 | | 8/1988 |
| KR | 101384986 | | 4/2014 |
| WO | WO 1997028098 | | 8/1997 |
| WO | WO 2002064702 | | 8/2002 |
| WO | WO 2003095382 | | 11/2003 |
| WO | WO 2004005435 | | 1/2004 |
| WO | WO 2008001218 | | 1/2008 |
| WO | WO 2010019256 | | 2/2010 |
| WO | WO 2010138914 | | 12/2010 |
| WO | WO 2011035292 | | 3/2011 |
| WO | WO 2011035294 | | 3/2011 |
| WO | WO 2012051647 | | 4/2012 |
| WO | WO 2012087887 | | 6/2012 |
| WO | WO 2012171857 | | 12/2012 |
| WO | WO 2013149122 | | 10/2013 |
| WO | WO 2014008496 | | 1/2014 |
| WO | WO 2014014919 | | 1/2014 |
| WO | WO 2015041669 | | 3/2015 |
| WO | WO 2015058206 | | 4/2015 |
| WO | WO 2015097116 | | 7/2015 |
| WO | WO 2015181028 | | 12/2015 |
| WO | WO 2015200060 | | 12/2015 |
| WO | WO 2016087397 | | 6/2016 |
| WO | WO 2016089813 | | 6/2016 |
| WO | WO 2016205894 | | 12/2016 |
| WO | WO 2017136641 | | 8/2017 |
| WO | WO 2017161157 | | 9/2017 |
| WO | WO 2017164822 | | 9/2017 |
| WO | WO 2018118024 | | 6/2018 |
| WO | WO-2018170032 A1 * | 9/2018 | ......... A61B 1/00006 |
| WO | WO 2018170035 | | 9/2018 |
| WO | WO 2018170065 | | 9/2018 |
| WO | WO-2022005473 A1 * | 1/2022 | |

OTHER PUBLICATIONS

U.S. Appl. No. 62/506,263, filed May 15, 2017, Jacobi et al.
U.S. Appl. No. 63/289,308, filed Dec. 14, 2021, Hull et al.
"Hydraulic Fracturing Fluid Product Component Information Disclosure," Jan. 2012, 2 pages.
Abad et al., "Evaluation of the Material Properties of the Multilayered Oxides formed on HCM12A using New and Novel Techniques," Manuscript Draft, Manuscript No. OXID-D-15-00019, 2015, 44 pages.
Abousleiman et al., "A Micromechanically Consistent Poroviscoelasticity Theory for Rock Mechanics Applications," Int. J. Rock Mech. Min. Sci. & Geomech. Abstr., 30:7, 1993, 4 pages.
Abousleiman et al., "Anisotropic Porothermoelastic Solution and Hydro-Thermal Effects on Fracture Width in Hydraulic Fracturing," Int. J. Numer. Anal. Meth. Geomech., 2013, 25 pages.
Abousleiman et al., "GeoGenome Industry Consortium (G2IC)," JIP, 2004-2006, 6 pages.
Abousleiman et al., "Geomechanics Field and Laboratory Characterization of Woodford Shale: The Next Gas Play," SPE International, SPE 110120, Society of Petroleum Engineers (SPE), presented at the 2007 SPE Annual Technical Conference and Exhibition on Nov. 11-14, 2007, 14 pages.
Abousleiman et al., "GeoMechanics Field Characterization of the Two Prolific U.S. Mid-West Gas Plays with Advanced Wire-Line Logging Tools," SPE 124428, Society of Petroleum Engineers (SPE), SPE International, presented at the 2009 SPE Annual Technical Conference and Exhibition, Oct. 4-7, 2009, 19 pages.
Abousleiman et al., "Mandel's Problem Revisited," Geotechnique, 46:2, 1996, 9 pages.
Abousleiman et al., "Mechanical Characterization of Small Shale Samples subjected to Fluid Exposure using the Inclined Direct Shear Testing Device," Int. J. Rock Mech. & Min. Sci., 47:3, 2010, 13 pages.
Abousleiman et al., "Poroelastic Solutions in Transversely Isotropic Media for Wellbore and Cylinder," Int. J. Solids Structures, 35:34-35, 1998, 25 pages.
Abousleiman et al., "Poroviscoelastic Analysis of Borehole and Cylinder Problems," ACTA Mechanica, 119, 1996, 21 pages.
Abousleiman et al., "The Granular and Polymer Composite Nature of Kerogen-Rich Shale," Acta Geotechnica, Feb. 5, 2016, 24 pages.
Agenet et al., "Fluorescent Nanobeads: a First Step Toward Intelligent Water Tracers," SPE 157019, Society of Petroleum Engineers (SPE), SPE International Oilfield Nanotechnology conference, Jun. 12-14, 2012, 13 pages.
Agilent Technologies, "Field-Deployable Solution for Nanoporosity Measurements in Mud Logging Operations and a Novel Method for Fracability Analysis Using Mud Cuttings," Agilent Technologies, Oct. 2013, 44 pages.
Al-Kattan and Al-Ameri, "Estimation of the Rock Mechanical Properties Using Conventional Log Data in North Rumaila Field," Iraqi Journal of Chemical and Petroleum Engineering, 13:4, Dec. 2012, 7 pages.

(56) References Cited

OTHER PUBLICATIONS

Allan et al., "A Multiscale Methodology for the Analysis of Velocity Anisotropy in Organic-Rich Shale," Geophysics, 80:4, Jul.-Aug. 2015, 16 pages.

Altowairqi, "Shale elastic property relationships as a function of total organic carbon content using synthetic samples," Journal of Petroleum Science and Engineering 133, Sep. 2015, 9 pages.

Ananthan et al., "Influence of Strain Softening on the Fracture of Plain Concrete Beams," Int. J. of Fracture, 45, 1990, 25 pages.

Anderson et al., "RockFlow: Fast Generation of Synthetic Source Rock Images Using Generative Flow Models," energies, Dec. 2020, 19 pages.

Anisimov, "The Use of Tracers for Reservoir Characterization," SPE 118862, Society of Petroleum Engineers (SPE), presented at SPE Middle East Oil and Gas Show and Conference, Mar. 15-18, 2009, 8 pages.

Archer and Rasouli, "A log based analysis to estimate mechanical properties and in-situ stresses in a shale gas well in North Perth Basin," Petroleum and Mineral Resources, WIT Transactions on Engineering Sciences, 81, 2012, 12 pages.

Aslan et al., "Fluorescent Core—Shell AG@$SiO_2$ Nanocomposites for Metal-Enhanced Fluorescence and Single Nanoparticle Sensing Platforms," Jan. 19, 2007, 2 pages.

Asylum Research MFP-3D (Year: NA), 1 page.

Atarita et al., "Predicting Distribution of Total Organic Carbon (TOC) and S2 with Δ Log Resistivity and Acoustic Impedance Inversion on Talang Akar Formation, Cipunegara Sub Basin, West Java," Procedia Engineering, 170:, 2017, 390-397, 8 pages.

Ballice, "Solvent Swelling Studies of Goynuk (Kerogen Type-I) and Beypazari Oil Shales (Kerogen Type-II)," Science Direct, Fuel 82, 2003, 5 pages.

Bazant et al., "Deformation of Progressively Cracking Reinforced Concrete Beams," ACI Journal, Technical Paper, Title No. 81-26, 81:3, May-Jun. 1984, 11 pages.

Bazant et al., "Size Effect in Brazilian Split-Cylinder Tests: Measurements and Fracture Analysis," ACI Materials Journal, 88:3 (325-332), May 31, 1991.

Bazant et al., "Strain-Softening Bar and Beam: Exact Non-Local Solution," Int. J. Solids Structures, 24:7, 1988, 15 pages.

Behura et al., "The shear properties of oil shales," Special Selection: Unconventional Resources and CO2 Monitoring, The Leading Edge, Jul. 2009, 6 pages.

Bell et al., "Molecular Level Study of Hot Water Extracted Green Tea Buried in Soils—a Proxy for Labile Soil Organic Matter," Scientific Reports, Jan. 2020, 10(1):1-13.

Beloborodov et al., "Compaction Trends of Full Stiffness Tensor and Fluid Permeability in Artificial Shales," Geophysical Journal International, Mar. 2018, 212(3):1687-1693.

Bennett et al., "Instrumented Nanoindentation and 3D Mechanistic Modeling of a Shale at Multiple Scales," Acta Geotechnica, 10:21, Jan. 9, 2015, 14 pages.

Bhandari et al., "Two-Dimensional DEM Analysis of Behavior of Geogrid-Reinforced Uniform Granular Bases under a Vertical Cyclic Load," Acta Geotechnica, 2014, 12 pages.

Biot et al., "Temperature analysis in hydraulic fracturing," Journal of Petroleum Technology, Nov. 1987, 39(11): 1389-1397.

Biot, "General Theory of Three-Dimensional Consolidation," Journal of Applied Physics, 12:2, Feb. 1941, 11 pages.

Blanz et al., "Nuclear Magnetic Resonance Logging While Drilling (NMR-LWD): From an Experiment to a Day-to-Day Service for the Oil Industry," Diffusion Fundamentals, 14(2), 2010, 5 pages.

Bobko et al., "The Nanogranular Origin of Friction and Cohesion in Shale—A Strength Homogenization Approach to Interpretation of Nanoindentation Results," Int. J. Numer. Anal. Meth. Geomech., 2010, 23 pages.

Borah et al., "Preparation of Ordered Porous Carbon from Tea by Chemical Activation and its Use in Cr(VI) Adsorption," Journal of Porous Materials, Oct. 2012, 19(5):767-774.

Boskey et al., "Perspective—Collagen and Bone Strength," Journal of Bone and Mineral Research, 14:3, 1999, 6 pages.

Bousige et al., "Realistic molecular model of kerogen's nanostructure," Nature Materials, Advance Online Publication, Feb. 1, 2016, 8 pages.

Brochard et al., "Fracture Properties of Kerogen and Importance for Organic-Rich Shales," Annual World Conference on Carbon (Carbon 2013), Jul. 2013, 5 pages.

Bunzil et al., "Taking advantage of luminescent lanthanide ions," Chemical Society Reviews, Dec. 2005, 29 pages.

Cahill et al., "Nanoscale Thermal Transport II," Applied Physics Reviews 1.1, 2014, 46 pages.

Cahill et al., "Nanoscale thermal transport," Journal of applied physics vol. 93, No. 2, Jan. 2003, 28 pages.

Cai et al., "Thermal Degradations and Processes of Waste Tea and Tea Leaves via TG-FTIR: Combustion Performances, Kinetics, Thermodynamics, Products and Optimization," Bioresource Technology, Nov. 2018, 268:715-25.

Carcione and Avseth, "Rock-physics templates for clay-rich source rocks," Geophysics 80:5 (D481-D500), Sep. 2015, 21 pages.

Carter and Hanson, "Fake Moon Dirt, HOOD Solar System Science," UT Dallas Magazine, 6:2, Spring 2016, 1 page.

Chang et al., "Magnetic SERS Composite Nanoparticles for Microfluidic Detection," 251st ACE National Meeting, Mar. 13-17, 2016, 1 pages.

Chen et al., "Size Effect in Micro-Scale Cantilever Beam Bending," Acta Mech., 2011, 17 pages.

Chen et al., "FITC functionalized magnetic core-shell $Fe_3O_4$/Ag hybrid nanoparticle for selective determination of molecular biothiols," Elsevier Ltd., Dec. 2013, 7 pages.

Chern et al., "Deformation of Progressively Cracking Partially Prestressed Concrete Beams," PCI Journal, 37:1, 1992, 11 pages.

Choi et al., "Enhanced Lithium Storage in Hierarchically Porous Carbon Derived from Waste Tea Leaves," Scientific Reports, Dec. 2016, 6(1): 1-10.

Chuang et al., "Ultra-sensitive in-situ detection of novel near-infrared persistent luminescent tracer nanoagents in crude oil-water mixtures," a natureresearch journal, Scientific Reports, Jun. 15, 2016, 5 pages.

Chupin et al., "Finite Strain Analysis of Nonuniform Deformation Inside Shear Bands in Sands," Int. J. Numer. Anal. Meth. Geomech., 2012, 16 pages.

Clough et al., "Characterization of Kerogen and Source Rock Maturation Using Solid-State NMR Spectroscopy," Energy & Fuels, 29(10):, 2015, 6370-6382, 42 pages.

Clough et al., "Characterization of Kerogen and Source Rock Maturation Using Solid-State NMR Spectroscopy," Energy & Fuels, Oct. 2015, 29(10):6370-82.

Committee on Field Tests, "International Society of Rock Mechanics—Commission on Standardization of Laboratory and Field Tests, Suggested methods for quantitative description of discontinuities in rock," Int. J. Rock Mech. Min. Sci. & Geomech. Abstr. 15: 319-368, Committee on Field Tests, Oct. 1977, 50 pages.

Corapcioglu, "Fracturing Fluid Effects on Young's Modulus and Embedment in the Niobrara Formation," Thesis for degree of Master of Science (Petroleum Engineering), Colorado School of Mines, 2014, 189 pages.

Cubillos et al., "The Value of Inter-well and Single Well Tracer Technology for De-Risking and Optimizing a CEOR Process—Caracara Field Case," SPE 174394-MS, Society of Petroleum Engineers (SPE), presented at EUROPEC 2015, Jun. 1-4, 2015, 19 pages.

Custelcean et al., "Aqueous Sulfate Separation by Crystallization of Sulfate-Water Clusters," Angew. Chem. Int. Ed., 2015, 54: 10525-10529.

Daneshy, "Hydraulic Fracturing to Improve Production," Tech 101, TheWayAhead, 6:3, Oct. 2010, 4 pages.

Danuor et al., "Determination of the Source and Depositional Environment of Sediments of Lake Bosumtwi using X-Ray Diffraction (XRD) Techniques," International Research Journal of Geology and Mining (IRJGM) 2:7 (186-198), Sep. 2012, 13 pages.

Das et al., "Molecular Fluorescence, Phosphorescence, and Chemiluminescence Spectrometry," Analytical Chemistry, Nov. 3, 2011, 29 pages.

(56) References Cited

OTHER PUBLICATIONS

De Block et al., "A New Solution for the Characterization of Unconventional Shale Resources Based on Analysis or Drill Cutting," SPE-177601-MS, Society of Petroleum Engineers (SPE), SPE International, presented at the Abu Dhabi International Petroleum Exhibition and Conference, Nov. 9-12, 2015, 6 pages.

Deans, "Using Chemical Tracers to Measure Fractional Flow and Saturation In-Situ," SPE 7076, Society of Petroleum Engineers (SPE), presented at SPE Symposium on improved Methods of Oil Recovery, Apr. 16-17, 1978, 10 pages.

Deere et al., "Engineering classifications and index properties for intact rock," Technical Report No. AFWL-TR 65-116, Air Force Weapons Library, Kirtland Air Force Base, New Mexico, USA, Dec. 1966, 327 pages.

Deirieh et al., "Nanochemomechanical Assessment of Shale: A Coupled WDS-Indentation Analysis," Acta Geotechnica, 2012, 25 pages.

Delafargue and Ulm, "Explicit approximations of the indentation modulus of elastically orthotropic solids for conical indenters," International Journal of Solids and Structures 41:26, Dec. 2004, 10 pages.

Devarapalli et al., "Micro-CT and FIB-SEM imaging and pour structure characterization of dolomite rock at multiple scales," Arabian Journal of Geosciences, Aug. 2017, 9 pages.

Dor et al., "Assembly of Clay Mineral Platelets, Tactoids, and Aggregates: Effect of Mineral Structure and Solution Salinity," Journal of Colloid and Interface Science, Apr. 2020, 566:163-170.

Dow et al., "Kerogen studies and geological interpretations," Journal of Geochemical Exploration, 1977, 7:79-99, 21 pages.

Du et al., "Interwell Tracer Tests: Lessons Learned from past Field Studies," SPE 93140, Society of Petroleum Engineers (SPE), presented at SPE Asia Pacific Oil and Gas Conference and Exhibition, Apr. 5-7, 2005, 9 pages.

Ducros, "Source Rocks of the Middle East," Source Rock Kinetics: Goal and Perspectives. AAPG Geosciences Technology Workshop, Jul. 2016, 30 pages.

Durand, "A History of Organic Geochemistry," Oil and Gas Science Technology, 2003, 58(2):203-231, 29 pages.

Ekbote et al., "Porochemoelastic Solution for an Inclined Borehole in a Transversely Isotropic Formation," J. of Eng. Mech., ASCE, Jul. 2006, 10 pages.

El-Aneed et al., "Mass Spectrometry, Review of the Basics: Electrospray, MALDI, and Commonly Used Mass Analyzers," Applied Spectroscopy Reviews, Mar. 16, 2009, 22 pages.

Elijah, "Numerical Modeling of Wellbore Instability (Tensile Failure) Using Fracture Mechanics Approach," Thesis for the degree of Master of Science, African University of Science and Technology Abuja, May 2013, 77 pages.

Elkatatny et al., "Development of a new correlation to determine the static Young's modulus," Journal of Petroleum Exploration and Production Technology, 8:1, Mar. 2018, 14 pages.

Equotip, "Equotip Operating Instructions," Manual, 2016, PROCEQ, 52 pages.

Ertas et al., "Petroleum Expulsion Part 1. Theory of Kerogen Swelling in Multicomponent Solvents," Energy & Fuels, 2006, 6 pages.

Esfahani et al., "Quantitative nanoscale mapping of three-phase thermal conductivities in filled skutterudites via scanning thermal microscopy," Nature Science Review, vol. 5, Issue 1, Feb. 2017, 31 pages.

Ewy, "Shale Swelling/Shrinkage and Water Content Change due to Imposed Suction and Due to Direct Brine Contact," Acta Geotechnica, 2014, 18 pages.

Frazer et al., "Localized Mechanical Property Assessment of SiC/SiC Composite Materials," Science Direct, 2015, Part A:70 (93-101).

Fu et al., "Hierarchical porous carbons: Design, preparation, and performance in energy storage," New Carbon Materials, Jun. 2011, 26(3):171-179.

Gao et al., "A Surface Functional Monomer-Directing Strategy for Highly Dense Imprinting of TNT at Surface of Silica Nanoparticles," Journal of American Chemical Society, vol. 129, No. 25, Jun. 2007, 7859-7866, 8 pages.

Gao et al., "Materials Become Insensitive to Flaws at Nanoscale: Lessons from Nature," PNAS, May 13, 2003, 100:10 (5597-600).

Gardiner et al., "Practical Raman Spectroscopy," Springer-Verlag, 1989, 9 pages.

Garnero, "The Contribution of Collagen Crosslinks to Bone Strength," Int. Bone & Mineral Society, Sep. 2012, 8 pages.

Georgi et al., "Physics and Chemistry in Nanoscale Rocks", SPE Forum Series: Frontiers of Technology, Mar. 22-26, 2015, La Jolla, California, USA, 4 pages.

Global Status of CCS Report, Dec. 11, 2020, Global CCS Institute, 44 pages.

Glossary.oilfield.slb.com' [online], "Oilfield Glossary: fluid-friction reducer," available on or before Jun. 15, 2017, retrieved from URL< http://www.glossary.oilfield.slb.com/Terms/f/fluid-friction_reducer.aspx>, 1 page.

Glover et al., "The Use of Measurements Made on Drill Cuttings to Construct and Apply Geomechanical Well Profiles," ARMA 16-0737, ARMA, presentation at the 50th US Rock Mechanics/Geomechanics Symposium, Jun. 26-29, 2016, 11 pages.

Goeppert et al., "Air as the renewable carbon source of the future: an overview of CO2 capture from the atmosphere," Energy Environ. Sci., 2012, 5: 7833, 12 pages.

Goodman, "Chapter 3: Rock Strength and Failure Criteria," in Introduction to Rock Mechanics, John Wiley & Sons, 21 pages.

Han et al., "Chapter 2: Principles of Drilling and Excavation," in Drilling in Extreme Environments: Penetration and Sampling on Earth and Other Plants, Aug. 2009, 107 pages.

Han et al., "LBM-DEM Modeling of Fluid-Solid Interaction in Porous Media," Int. J. Numer. Anal. Meth. Geomech., 2013, 37: 1391-1407.

Han et al., "Numerical Modeling of Elastic Hemispherical Contact for Mohr-Coulomb Type Failures in Micro-Geomaterials," Experimental Mechanics, 57, Jun. 16, 2017, 15 pages.

Han et al., "Application of Silver-Coated Magnetic Microspheres to a SERS-Based Optofluidic Sensor," The Journal of Physical Chemistry (JPCC), Mar. 7, 2011, 7 pages.

Havens, "Mechanical Properties of the Bakken Formation," thesis for degree of Master of Science (Geophysics) at the Colorado School of Mines, Department of Geophysics, 2012, 123 pages.

Hepburn et al., "The technological and economic prospects for CO2 utilization and removal," Nature, Nov. 2019, 575, 11 pages.

Hillier, "Accurate quantitative analysis of clay and other minerals in sandstones by XRD: comparison of a Rietveld and a reference intensity ratio (RIR) method and the importance of sample preparation," Clay Minerals, 2000, 35:391-302.

Ho et al., "Tea Aroma Formation," Food Science and Human Wellness, Mar. 2015, 4(1):9-27.

Hoang et al., "Correspondence Principle Between Anisotropic Poroviscoelasticity and Poroelasticity using Micromechanics and Application to Compression of Orthotropic Rectangular Strips," Journal of Applied Physics, American Institute of Physics, Aug. 2012, 112, 16 pages.

Hornby et al., "Anisotropic Effective-Medium Modeling of the Elastic Properties of Shales," Geophysics, Oct. 1994, 59:10 (1570-1583).

Hosemann et al., "Mechanical Characteristics of SiC Coating Layer in TRISO Fuel Particles," Journal of Nuclear Materials, 2013, 442: 133-142.

Hosemann et al., "An Exploratory Study to Determine Applicability of Nano-Hardness and Micro-compression Measurements for Yield Stress Estimation," Science Direct, 2008, 375: 135-143.

Hu et al., "Smart Liquid SERS Substrates based on $Fe_3O_4$/Au Nanoparticles with Reversibility Tunable Enhancement Factor for Practical Quantitative Detection," a natureresearch journal, Scientific Reports, Nov. 2014, 4:7204, 10 pages.

Hull and Abousleiman, "Chapter 10: Insights of the Rev of Source Shale from Nano- and Micromechanics," in New Frontiers in Oil and Gas Exploration, Springer International Publishing Switzerland, 2016, 29 pages.

(56) References Cited

OTHER PUBLICATIONS

Hull et al., "Chemomechanical Effects of Oxidizer-CO2 Systems Upon Hydraulically Fractured Unconventional Source Rock," Canadian Journal of Chemical Engineering, 2021.
Hull et al., "Oxidative Kerogen Degradation: A Potential Approach to Hydraulic Fracturing in Unconventionals," Energy Fuels, 2019, 33: 4758-4766, 8 pages.
Hull et al., "Synthesis and structural characterization of CO2-soluble oxidizers [Bu4N]BrO3 and [Bu4N]ClO3 and their dissolution in cosolvent-modified CO2 for reservoir applications," RSC Advances, Royal Society of Chemistry, Dec. 21, 2020, 10: 44973, 8 pages.
Hur et al., "Reactive force fields for modeling oxidative degradation of organic matter in geological formations," Sep. 1, 2021.
Huseby et al., "High Quality Flow Information from Tracer Data," SPE-169183-MS, Society of Petroleum Engineers (SPE), presented at the SPE Bergen One Day Seminar, Grieghallen, Bergen, Norway, Apr. 2, 2014, 9 pages.
Hutchins et al., "Aqueous Tracers for Oilfield Applications," SPE-21049, Society of Petroleum Engineers (SPE), presented at the SPE International Symposium on Oilfield Chemistry, Anaheim, California, Feb. 20-22, 1991; Society of Petroleum Engineers, 1991, 9 pages.
Iqbal et al., "In situ micro-cantilver tests to study fracture properties of NiAl single crystals," Acta Materialia, Feb. 2012, 60:3 (1193-1200).
Itasca "Three-dimensional Fast Lagrangian Analysis of Continua (FLAC3D)," available on or before 2012, [retrieved on Jun. 7, 2018], retrieved from URL: < https://www.itascacg.com/software/flac3d>, 4 pages.
Iyengar et al., "Analysis of Crack Propagation in Strain-Softening Beams," Engineering Fracture Mechanics, 2002, 69: 761-778.
Jacobi, "Source productivity assay for reservoir knowledge," Saudi Aramco, Jan. 2021, 37 pages.
Jarvie et al., "Oil and shale gas from the Barnett Shale, Fort Worth Basin, Texas," American Association of Petroleum Geologists National Convention, Jun. 2001, Denver, CO, 29 pages.
Jia et al., "Highly Efficient Extraction of Sulfate Ions with a Tripodal Hexaurea Receptor," Angew. Chem. Int. Ed., 2011, 50: 486-490.
Jianhong et al., "Estimation of the Tensile Elastic Modulus using Brazilian disc by Applying Diametrically Opposed Concentrated Loads," International Journal of Rock Mechanics & Mining Sciences, 2009, 46(3): 568-576.
Jose et al., "Continuous multi cycle nanoindentation studies on compositionally graded $Ti_{1-x}Al_xN$ multilayer thin films," Materials Science and Engineering, ELSEVIER, Apr. 2011, 528(21): 6438-6444.
Jun et al., "Multifunctional Silver-Embedded Magnetic Nanoparticles as SERS Nanoprobes and Their Applications," Wiley-VCH Verlag GmbH& Co. KGaA, Weinheim, Jan. 4, 2010, 7 pages.
Kadhim et al., "Using Well Logs Data to Estimate Dynamic Elastic Properties of Carbonate Formation," International Journal of Physical and Human Geography, Jun. 2016, 4(2): 1-15.
Kelemen et al., "Petroleum Expulsion Part 2. Organic Matter Type and Maturity Effects on Kerogen Swelling by Solvents and Thermodynamic Parameters for Kerogen from Regular Solution Theory," Energy & Fuels, 2006, 20: 301-308.
Kernan, "Electrofacies, elemental composition, and source rock characteristics along seismic reflectors of the Vaca Muerta formation in the Loma La Lata area, Neuquen Basin, Argentina," Master Thesis, Colorado School of Mines, 2014, 123 pages.
Kethireddy, "Quantifying the effect of kerogen on Electrical Resistivity Measurements in Organic Rich Source Rocks," Thesis in partial fulfillment of the requirements for the degree of Master of Science, Dec. 2013, 78 pages.
Khatibi et al., "Raman spectroscopy to study thermal maturity and elastic modulus of kerogen," International Journal of Coal Geology, Jan. 2018, 185: 103-118.

Kim et al., "Numerical analysis of fracture propagation during hydraulic fracturing operations in shale gas systems," International Journal of Rock and Mechanics Mining Sciences, 2015, 76:127-137, 11 pages.
Kimber, "X-Ray Diffraction of Lacustrine Mineral as an Indicator of Late Pleistocene and Holocene Paleoclimate, Tulare Lake, California," A Thesis Submitted to the Department of Geological Sciences California State University, Bakersfield, In Partial Fulfillment for the Degree of Masters of Science in Geology, Jun. 2018.
Klapetek, "Chapter 11: Thermal Measurements," Quantitative Data Processing in Scanning Probe Microscopy: SPE Applications for Nanometrology, 2018, 26 pages.
Kneipp et al., "Single Molecule Detection Using Surface-Enhanced Raman Scattering (SERS)," Physical Review Letters, American Physical Society 78:9, Mar. 3, 1997, 4 pages.
Kolymbas, "Kinematics of Shear Bands," Acta Geotechnica, 2009, 4: 315-318.
Kumar et al., "Nano to Macro Mechanical Characterization of Shale," SPE 159804, Presented at the SPE Annual Technical Conference and Exhibition, San Antonio, Texas, Oct. 8-10, 2012; Society of Petroleum Engineers, 2012, 23 pages.
Kwabi, "Mineral, Fluid, Elastic Property Quantification from Well Logs and Core Data in the Eagle Ford Shale Play: A Comparative Study," Thesis for Degree of Master of Science and Engineering at the University of Texas at Austin, Aug. 2013, 135 pages.
Lafargue et al., "Rock-Eval applications in hydrocarbon exploration, production and soil contamination studies," Revue de Institut Francais du Petrole, 1998, 53(4):421-437, 17 pages.
Lam et al., "Experiments and Theory in Strain Gradient Elasticity," J. Mech. and Phys. of Solids, 2003, 51: 1477-1508.
Larsen et al., "Changes in the Cross-Link Density of Paris Basin Toarcian Kerogen During Maturation," Organic Geochemistry, 2002, 33: 1143-1152.
Lee et al., "Comparison of different methods to estimate uniaxial compressive strength in a Barnett shale," in proceedings of the 50th US Rock Mechanics/Geomechanics Symposium, ARMA 16-0455, Jun. 26-29, 2016, 9 pages.
Lee et al., "New application of rebound hardness Nos. to generate logging of unconfined compressive strength in laminated shale formations," in proceedings of the 48th US Rock Mechanics/Geomechanics Symposium, Minneapolis, MN, AMRA 14-6972, Jun. 1-4, 2014, 7 pages.
Lee, "A study on rock slope stability in Boeun region using distinct element method," MS Thesis, Department of Earth System Sciences, Yonsei University, Seoul, South Korea, 2001, English Translation.
Lee, "Calibration of rebound hardness Nos. to unconfined compressive strength in shale formations," Journal of Petroleum Technology, JPT, Jan. 2015, 5 pages.
Lee, "Time-dependent crack growth in brittle rocks and field applications to geologic hazards," PhD Dissertation. Department of Mining and Geological Engineering, University of Arizona, Tucson, AZ 2007, 272 pages.
Leeb, "New dynamic method for hardness testing of metallic materials," VDI-Report, 308: 123-128, 1978, 5 pages.
Lewan, "Evaluation of petroleum generation by hydrous pyrolysis experimentation," Phil. Trans. R. Soc. Lond. A, 315:, 1985, 123-134, 13 pages.
Lewan, "Experiments on the role of water in petroleum formation," Geochimica et Cosmochimica Acta, Pergamon, 61:17, 1997, 3691-3723, 33 pages.
Li et al., "Mechanical Characterization of Micro/Nanoscale Structures for MEMS/NEMS Applications using Nanoindentation Techniques," Science Direct, 2003, 775 pages.
Li et al., "The Brazilian Disc Test for Rock Mechanics Applications: Review and New Insights," Rock Mech Rock Eng, 2013, 46: 269-287.
Liu, "Dimension effect on mechanical behavior of silicon microcantilver beams," Measurement, 41:8, Oct. 2008, 11 pages.
Liu, "Elastic Constants Determination and Deformation Observation Using Brazilian Disk Geometry," Experimental Mechanics, 2010, 50: 1025-1039.

(56) References Cited

OTHER PUBLICATIONS

Liu, "Fracture Toughness Assessment of Shales by Nanoindentation," Thesis for the degree of Master of Science in Civil Engineering, Geotechnical Engineering Masters Projects, University of Massachusetts Amherst, Sep. 2015, 80 pages.
Liu, "Micro-cantilver Testing to Evaluate the Mechanical Properties of Thermal Barrier Coatings," 19th European Conference on Fracture (ECF19): Fracture Mechanics for Durability, Reliability and Safety; Conference Proceedings held Aug. 26-31, 2012, Kazan, Russia; 7 pages.
Lu et al., "Quantitative prediction of seismic rock physics of hybrid tight oil reservoirs of the Permian Lucaogou Formation, Junggar Basin, Northwest China," Journal of Asian Earth Sciences, 178:, 2019, 216-223, 8 pages.
Luan et al., "Creation of synthetic samples for physical modelling of natural shale," Geophysical Prospecting, 64, Jul. 2016, 17 pages.
Mahabadi et al., "A novel approach for micro-scale characterization and modeling of geomaterials incorporating actual material heterogeneity," Geophysical Research Letters, American Geophysical Union, 39:1 (L01303), Jan. 1, 2012, 6 pages.
Mahmoud et al., "Removal of Pyrite and Different Types of Iron Sulfide Scales in Oil and Gas Wells without H2S Generation," (IPTC-18279-MS) Presented at the International Petroleum Technology Conference (IPTC), Doha, Qatar, Dec. 6-9, 2015; 8 pages.
Maio et al., "Measuring Fracture Toughness of Coatings using Focused-ion-beam-machined Microbeams," 2004, 4 pages.
Mao et al., "Chemical and nanometer-scale structure of kerogen and its change during thermal maturation investigated by advanced solid-state 13C NMR spectroscopy," Geochimica et Cosmochimica Acta, 74(7):, 2010, 2110-2127, 18 pages.
Marchetti et al., "Fluorous affinity chromatography for enrichment and determination of perfluoroalkyl substances," Annual Review of Analytical Chemistry 84, Jul. 19, 2012, 8 pages.
Marinos and Hoek, "Estimating the geotechnical properties of heterogeneous rock masses such as flysch," Bull. Enginng. Geol. & the Environment (IAEG), 60:85-92, 2001, 8 pages.
Maxwell, "Microseismic hydraulic fracture imaging: The path toward optimizing shale gas production," The Leading Edge, Mar. 2011, 6 pages.
McCann and Entwisle, "Determination of Young's modulus of the rock mass from geophysical well logs," Geological Applications of Wireline Logs II, Geological Society of Special Publication 65, Dec. 1, 1992, 9 pages.
Mesa, "Spherical and rounded cone nano indenters," Micro Star Technologies Inc., available on or before Jan. 23, 2018, 24 pages.
Meyer et al., "Identification of Source Rocks on Wireline Logs by Density/Resistivity and Sonic Transit Time/Resistivity Crossplots," AAPG Bulletin, 68(2):, 1984, 121-129, 9 pages.
Michael et al., "Determination of Insitu Hydrocarbon Volumes in Liquid Rich Plays," presented at the Geoscience Technology Workshop, hydrocarbon charge considerations in Liquid-rich uncoventional petroleum systems, Mar. 2014, 24 pages.
Montaut et al., "Detection and quantification of rock physics properties for improved hydraulic fracturing in hydrocarbon-bearing shale," SPWLA 54th Annual Logging Symposium, Jun. 22-26, 2013, 16 pages.
Montgomery, "Chapter 2: Fracturing Fluid Components," in Intech open science | open minds, Montgomery, 2013, 21 pages.
Moyer, "A Case for Molecular Recognition in Nuclear Separations: Sulfate Separation from Nuclear Wastes," Inorganic Chemistry, 2012, 3473-3490.
Moyner et al., "The Application of Flow Diagnostics for Reservoir Management," Society of Petroleum Engineers (SPE), Apr. 2015, 18 pages.
Muktadir et al., "Application of X-ray Diffraction (XRD) and Rock-Eval Analysis for the Evaluation of Middle Eastern Petroleum Source Rock," Energies, 2021, 14:6672, 16 pages.
Nie et al., "Probing Single Molecules and Single Nanoparticles by Surface-Enhanced Raman Scattering," Science, vol. 275, No. 5303, Feb. 1997, 1102-1106, 6 pages.

Nottenburg et al., "Temperature and stress dependence of electrical and mechanical properties of Green River oil shale," Fuel, IPC Science and Technology Press, 58:2 (144-148), Feb. 1, 1979, 5 pages.
Oliver and Pharr, "An improved technique for determining hardness and elastic modulus using load and displacement sensing indentation experiments," Journal of Materials Research, 7:6, Jun. 1992, 20 pages.
Oliver and Pharr, "Measurement of hardness and elastic modulus by instrumented indentation: Advances in understanding and refinements to methodology," Journal of Materials Research, 19:1, Jan. 2004, 18 pages.
Ortega et al., "The Effect of Particle Shape and Grain-Scale Properties of Shale: A Micromechanics Approach," Int. J. Numer. Anal. Methd. Geomech., 2010, 33 pages.
Ortega et al., "The Effect of the Nanogranular Nature of Shale on their Poroelastic Behavior," Acta Geotechnica, 2007, 28 pages.
Ortega et al., "The Nanogranular Acoustic Signature of Shale," Geophysics, 74:3, May-Jun. 2009, 20 pages.
Pant, "Nanoindentation characterization of clay minerals and clay-based hybrid bio-geomaterials," dissertation for degree of Doctor of Philosophy in the Department of Civil and Environmental Engineering at the Louisiana State University and Agricultural and Medical College, Dec. 2013, 111 pages.
Passey et al., "From Oil-Prone Source Rock to Gas Producing Shale Reservoir—Geologic and Petrophysical Characterization of Unconventional Shale-Gas Reservoirs," SPE 131350, presented at the SPE International Oil & Gas Conference and Exhibition, Bejing, China, Jun. 2010, 29 pages.
Petoud et al., "Brilliant SM, Eu, Tb, and Dy Chiral Lanthanide Complexes with Strong Circularly Polarized Luminescence," Journal of the American Chemical Society (JACS), Dec. 15, 2006, 7 pages.
Podio et al., "Dynamic Properties of Dry and Water-Saturated Green River Shale under Stress," SPE 1825, Society of Petroleum Engineers (SPE), Jun. 11, 1968, 16 pages.
Pollard et al., "Fundamentals of Structural Geology," Cambridge University Press, Sep. 1, 2005, p. 291.
Pollock and Hammiche, "Micro-thermal analysis: techniques and applications," Journal of Physics D: Applied Physics, 34.9, 2001, 31 pages.
Poon et al., "An Analysis of Nanoindentation in Linearly Elastic Solids," International Journal of Solids and Structures, 45:24, Dec. 1, 2008, 16 pages.
Potter and Foltinek, "Formation elastic parameters by deriving S-wave velocity logs," CREWES Research Report—vol. 9, Jan. 1997, 13 pages.
Prasad et al., "Acoustic Signatures, Impedance Microstructure, Textural Scales and Anisotrophy of Kerogen-Rich Shales," SPE 124840-MS, Society of Petroleum Engineers (SPE), Annual Technical Conference and Exhibition, Oct. 4-7, 2009, 13 pages.
Proceq S.A. 2014. 2014 Equotip, Copyright, Switzerland, 1 page.
Rajbanshi et al., "Sulfate Separation from Aqueous Alkaline Solutions by Selective Crystallization of Alkali Metal Coordination Capsules," Cryst. Growth Des., 2011, 2702-2706.
Rashadan et al., "Effect of the Preparation Route, PEG and Annealing on the Phase Stability of Fe3O4 Nanoparticles and Their Magnetic Properties" Journal of Experimental Nanoscience, vol. 8, No. 2, 2013, 210-222, 14 pages.
Rezaee et al., "Depositional Environment Interpretation of Lar Formation (Upper Jurassic) Based on Study of Clay Mineralogy and Microfacies in East Azarbaijan (North Western of Iran)," Asian Journal of Earth Sciences, 7:1 (17-26), 2014, 10 pages.
Richard et al, "Slow Relaxation and Compaction of Granular Systems," Nature Materials, Feb. 4, 2005, 8 pages.
Rowan et al., "Dynamic Covalent Chemistry," Angewante Chemie International Edition, Mar. 15, 2002, 55 pages.
Selvin et al., "Principles and biophysical applications of lanthanide-based probes," Annual Review of Biophysics and Biomolecular Structure, Jun. 2002, 28 pages.
Serres-Piole et al., "Water tracers in oilfield applications: Guidelines," Elsevier Ltd., Journal of Science and Engineering, Nov. 2012, 18 pages.

(56) References Cited

OTHER PUBLICATIONS

Shabro et al., "Pore-scaling modeling of electrical resistivity and permeability in FIB-SEM images of organic mudrock," Geophysics, Society of Exploration Geophysicists 79:5 (D289-D299), Sep.-Oct. 2014, 11 pages.
Shahid et al., "Natural-fracture reactivation in shale gas reservoir and resulting microseismicity," Journal of Canadian Petroleum Technology 54.06, 2015.
Sharma and Arya, "Formation strength estimation from well log data for sand cut analysis in Tapti—Daman Area, Western Offshore Basin, India," presented at the 6th International Conference and Exposition on Petroleum Geophysics, Kolkata 2006, Jan. 9-11, 2006, 4 pages.
Shin et al., "Development and Testing of Microcompression for Post Irradiation Characterization of ODS Steels," J. Nuclear Materials, 2014, 6 pages.
Shook et al., "Determining Reservoir Properties and Flood Performance from Tracer Test Analysis," SPE 124614, Society of petroleum Engineers (SPE), presented at SPE Annual Technical Conference and Exhibition, Oct. 4-7, 2009, 19 pages.
Shukla et al., "Nanoindentation Studies on Shales," ARMA 13-578, ARMA, presented at the 47th US Rock Mechanics/Geomechanics Symposium, Jun. 23-26, 2013, 10 pages.
Sierra et al., "Woodford Shale Mechanical Properties and the Impacts of Lithofacies," ARMA 10-461, copyright 2010, 10 pages.
Singh et al., "Facies classification based on seismic waveform," presented at the 5th Conference & Exposition on Petroleum Geophysics, Jan. 15-17, 2004, 7 pages.
Siskin et al., "Reactivity of organic compounds in hot water: geochemical and technological implications," Science, Oct. 11, 1991, 8 pages.
Slatt et al., "Merging Sequence Stratigraphy and Geomechanics for Unconventional Gas Shales," The Leading Edge, Mar. 2011, 8 pages.
Slatt et al., "Outcrop/Behind Outcrop (Quarry), Multiscale Characterization of the Woodford Gas Shale," 2011, 22 pages.
Solomon et al., "Synthesis and Study of Silver Nanoparticles" Journal of Chemical Education vol. 84, No. 2, 2007, 332-325, 4 pages.
Sone et al., "Mechanical Properties of Shale-Gas Reservoir Rocks—Part 1: Static and Dynamic Elastic Properties and Anisotropy," Geophysics, vol. 78, No. 5, Sep.-Oct. 2013, 12 pages.
Sone et al., "Mechanical Properties of Shale-Gas Reservoir Rocks—Part 2: Ductile creep, brittle strength, and their relation to the elastic modulus," 2013, Geophysics, vol. 78, No. 5, 10 pages.
Song et al., "SERS-Encoded Nanogapped Plasmonic Nanoparticles: Growth of Metallic Nanoshell by Templating Redox-Active Polymer Brushes," Journal of the American Chemical Society (JACS), Apr. 28, 2014, 4 pages.
Stiles et al., "Surface-enhanced Raman Spectroscopty," Annual Review of Analytical Chemistry, Mar. 18, 2008, 29 pages.
Tabatabaei et al., "Well performance diagnosis with temperature profile measurements," Society of Petroleum Engineers (SPE), in SPE Annual Technical Conference and Exhibition, Society of Petroleum Engineers, Oct. 30-Nov. 2, 2011, Jan. 2011, 16 pages.
Tathed et al., "Hydrocarbon saturation in Bakken Petroleum System based on joint inversion of resistivity and dielectric dispersion logs," Fuel, 233:, Dec. 2018, 45-55, 11 pages.
Technically Recoverable Shale Oil and Shale Gas Resources: An Assessment of 137 Shale Formations in 41 Countries Outside the United States, United States Energy Information Administration, Jun. 2013, 730 pages.
Tian et al., "Off-Resonant Gold Superstructures as Ultrabright Minimally Invasive Surface-Enhanced Raman Scattering (SERS) Probes," American Chemical Society, Jul. 2015, 7 pages.
Till and Spears, "The determination of quartz in sedimentary rocks using an x-ray diffraction method," Clays and Clay Minerals, 17: 323-327, 1969, 5 pages.

Tong et al., "Committed Emissions from Existing Energy Infrastructure Jeopardize 1.5° C. Climate Target," Nature, 2019, 572(7769): 373-377, 17 pages.
Trippetta et al., "The seismic signature of heavy oil on carbonate reservoir through laboratory experiments and AVA modelling," Journal of Petroleum Science and Engineering, 177:, 2019, 849-860, 12 pages.
Ulm et al., "Material Invariant Poromechanics Properties of Shales," 2005, 8 pages.
Ulm et al., "The Nanogranular Nature of Shale," Acta Geotechnica, 2006, 12 pages.
Vanlandingham, "Review of Instrumented Indentation," Journal of Research of the National Institute of Standards and Technology, 108:4, Jul.-Aug. 2003, 17 pages.
Vernik and Landis, "Elastic Anisotropy of Source Rocks: Implications for Hydrocarbon Generation and Primary Migration," 80:4, Apr. 1996, 14 pages.
Vernik et al., "Ultrasonic Velocity and Anisotropy of Hydrocarbon Source Rocks," Geophysics, 57:5, May 1992, 9 pages.
Walters et al., "Kinetic rheology of hydraulic fracturing fluids," SPE 71660, Society of Petroleum Engineers, presented at the 2001 SPE Annual Technical Conference and Exhibition, Sep. 30-Oct. 3, 2001, 12 pages.
Wang et al., "Characterization of electrical properties of organic-rich shales at nano/micro scales," Marine and Petroleum Geology, 86:563-572, Jun. 16, 2017, 10 pages.
Wang et al., "Iron Sulfide Scale Dissolvers: How Effective Are They?" SPE 168063, Society of Petroleum Engineers (SPE), presented at the SPE Saudi Arabia section Annual Technical Symposium and Exhibition, May 19-22, 2013, 22 pages.
Wang et al., "Molecular Simulation of CO2/CH4 Competitive Adsorption on Shale Kerogen for CO2 Sequestration and Enhanced Gas Recovery," J. Phys. Chem. C, 2018, 122, 30, 17009-17018, 29 pages.
Wang et al., "The Flattened Brazilian Disc Specimen Used for Testing Elastic Modulus, Tensile Strength and Fracture Toughness of Brittle Rocks: Analytical and Numerical Results," International Journal of Rock Mechanics and Mining Sciences, 41:2 (245-253).
Warpinski, "Understanding Hydraulic Fracture Growth, Effectiveness, and Safety Through Microseismic Monitoring," Intech, May 17, 2013, 14 pages.
Wegst et al., "Bioinspired structural materials," Nature Materials, Jan. 14, 2015, 14 pages.
Wenk et al., "Preferred Orientation and Elastic Anisotropy of Illite-Rich Shale," Geophysics, 72:2, Mar.-Apr. 2007, 7 pages.
Wessels et al., "Identifying fault activation during hydraulic stimulation in the Barnett shale: source mechanisms, b values, and energy release analyses of microseismicity," presented at the SEG San Antonio 2011 Annual Meeting, Sep. 18-23, 2011, 5 pages.
West and Shakoor, "Chapter 8: Engineering properties of rocks," in Geology Applied to Engineering, 2nd Edition, Waveland Press, Inc, ISBM 1-4786-3500-2, p. 170, 2018, 1 page.
White et al., "A thermoplasticity model for oil shale," LLNL-CONF-667671, Lawrence Livermore National Labtoratory, presented at the Fifth International Conference on Coupled Thermo-Hydro-Mechanical-Chemical Processes in Geosystems, Feb. 25-27, 2015, 20 pages.
Wilson et al., "Fracture testing of bulk silicon microcantilever beams subjected to a side load," Journal of Microelectromechanical Systems, 5:3, Sep. 1996, 9 pages.
Wu et al., "A reusable biosensor chip for SERS-fluorescence dual mode immunoassay," Proc. SPIE 9543, Third International Symposium on Laser Interaction with Matter, 954317, May 4, 2015, 6 pages.
Wu et al., "A SERS-Assisted 3D Barcode Chip for High-Throughput Biosensing," Small Journal 11:23, Jun. 11, 2015, 9 pages.
Wurster et al., "Characterization of the fracture toughness of micro-sized tungsten single crystal notched specimens," Philosophical Magazine, 92:14, May 2012, 23 pages.
Xu et al., "Measurement of two-photon excitation cross sections of molecular fluorophores with data from 690 to 1050 nm," Journal of the Optical Society of America B, Mar. 1996, 11 pages.

(56) References Cited

OTHER PUBLICATIONS

Yan and Han, "Measurement of elastic properties of kerogen," SEG Houston 2013 Annual Meeting, SEG Technical Program Expanded Abstracts, Sep. 2013, 5 pages.

Yang et al., "Nanoscale geochemical and geomechanical characterization of organic matter in shale," Nature Communications, 8:2179, Dec. 19, 2017, 9 pages.

Zamberi et al., "Improved Reservoir Surveillance Through Injected Tracers in a Saudi Arabian Field: Case Study," SPE 166005, Society of Petroleum Engineers (SPE), presented at SPE Reservoir Characterization and Simulation Conference and Exhibition, Sep. 16-18, 2013, 15 pages.

Zemel, "Chapter 3: Interwell Water Tracers," in Tracers in the Oil Field, 43, 1st Edition, Elsevier Science, Jan. 13, 1995, 47 pages.

Zeszotarski et al., "Imaging and Mechanical Property Measurements of Kerogen via Nanoindentation," Geochimica et Cosmochimica Acta, 68:20, Oct. 15, 2004, 7 pages.

Zhou et al., "Three-Dimensional Hierarchical Porous Carbon Cathode Derived from Waste Tea Leaves for the Electrocatalytic Degradation of Phenol," Langmuir, Oct. 2019, 35(4):12914-12926.

Zhou et al., "Upconversion luminescent materials: advances and applications," Chem Rev., Jan. 14, 2015, 71 pages.

\* cited by examiner

FIG. 6A

ALL Wt % from XRD — Wt%

| Type | Depth (ft) | Quartz | Albite | K-Feldspar | Mica-Ill-Smec | Chlorite | Kaolinite | Calcite | Dolomite | Siderite | Pyrite | Anatase | Apatite | Barite | Anhydrite | Halite | Hematite | Smectite | Illite | Chlorite | Magnesite | Gypsum | Celestine | SUM |
|---|---|---|---|---|---|---|---|---|---|---|---|---|---|---|---|---|---|---|---|---|---|---|---|---|
| 01G-10491P5 | 10,491.5 | 3.7 | 0.0 | 1.1 | 13.9 | 0.5 | 12.0 | 61.7 | 0.7 | 0.3 | 5.0 | 0.5 | 0.1 | 0.0 | | | 0.0 | 0.0 | 0.0 | 0.0 | 0.0 | | | 99.4 |
| 02G-10500P5 | 10,500.5 | 6.7 | 0.0 | 1.1 | 12.9 | 0.0 | 8.6 | 65.0 | 0.5 | 0.2 | 4.4 | 0.4 | 0.1 | 0.0 | | | 0.0 | 0.0 | 0.0 | 0.0 | 0.0 | | | 99.5 |
| 03G-10509P5 | 10,509.5 | 7.7 | 0.1 | 1.1 | 13.1 | 0.0 | 9.2 | 61.6 | 0.3 | 0.2 | 4.9 | 0.4 | 0.0 | 0.0 | | | 0.0 | 0.0 | 0.0 | 0.0 | 0.0 | | | 99.0 |
| 04G-10524 | 10,524.0 | 5.8 | 0.1 | 1.2 | 13.2 | 0.2 | 6.9 | 66.0 | 0.4 | 0.2 | 4.3 | 0.5 | 0.0 | 0.0 | | | 0.0 | 0.0 | 0.0 | 0.0 | 0.0 | | | 99.7 |
| 05G-10530 | 10,530.0 | 5.3 | 0.2 | 1.2 | 12.4 | 0.8 | 6.5 | 68.0 | 0.2 | 0.2 | 4.4 | 0.4 | 0.0 | 0.0 | | | 0.0 | 0.0 | 0.0 | 0.0 | 0.0 | | | 99.7 |
| 06G-10536.5 | 10,536.5 | 6.2 | 0.2 | 0.7 | 14.7 | 0.0 | 5.6 | 65.5 | 0.2 | 0.3 | 4.4 | 0.2 | 0.0 | 0.0 | | | 0.0 | 0.0 | 0.0 | 0.0 | 0.0 | | | 99.2 |
| 07G-10548 | 10,548.0 | 6.3 | 0.1 | 1.0 | 11.6 | 0.0 | 4.8 | 71.1 | 1.4 | 0.4 | 2.4 | 0.1 | 0.2 | 0.0 | | | 0.0 | 0.0 | 0.0 | 0.0 | 0.0 | | | 99.5 |
| 08G-10581 | 10,581.0 | 1.7 | 0.0 | 0.3 | 7.9 | 0.0 | 0.6 | 86.2 | 7.9 | 0.5 | 0.4 | 0.0 | 0.1 | 0.0 | | | 0.0 | 0.0 | 0.0 | 0.0 | 0.0 | | | 99.7 |
| 09G-10590 | 10,590.0 | 0.5 | 0.0 | 0.1 | 1.2 | 0.0 | 0.2 | 93.7 | 4.1 | 0.4 | 0.3 | 0.0 | 0.2 | 0.0 | | | 0.0 | 0.0 | 0.0 | 0.0 | 0.0 | | | 99.3 |
| 10G-10605 | 10,605.0 | 0.6 | 0.0 | 0.6 | 0.5 | 0.0 | 0.3 | 92.4 | 2.4 | 0.3 | 1.0 | 0.0 | 0.4 | 0.0 | | | 0.0 | 0.0 | 0.0 | 0.0 | 0.0 | | | 99.8 |
| 11G-10623 | 10,623.0 | 1.1 | 0.0 | 0.2 | 1.7 | 0.0 | 0.6 | 88.7 | 2.3 | 0.1 | 0.7 | 0.2 | 0.2 | 0.0 | | | 0.0 | 0.0 | 0.0 | 0.0 | 0.0 | | | 99.8 |
| 12G-10644.5 | 10,644.5 | 2.1 | 0.1 | 0.8 | 2.2 | 0.0 | 1.2 | 88.2 | 3.3 | 0.3 | 0.6 | 0.1 | 0.4 | 0.0 | | | 0.0 | 0.0 | 0.0 | 0.0 | 0.0 | | | 99.3 |
| 13G-10665 | 10,665.0 | 2.4 | 0.0 | 0.5 | 3.6 | 0.0 | 2.0 | 82.6 | 2.2 | 0.2 | 0.8 | 0.2 | 0.2 | 0.0 | | | 0.0 | 0.0 | 0.0 | 0.0 | 0.0 | | | 99.8 |
| 14G-10672.5 | 10,672.5 | 2.0 | 0.1 | 1.0 | 6.2 | 0.1 | 1.4 | 82.5 | 2.0 | 0.2 | 2.8 | 0.4 | 0.1 | 0.0 | | | 0.0 | 0.0 | 0.0 | 0.0 | 0.0 | | | 99.4 |
| 15G-10677.5 | 10,677.5 | 3.0 | 0.1 | 0.8 | 10.8 | 0.1 | 2.0 | 74.4 | 1.6 | 0.5 | 4.7 | 0.2 | 0.3 | 0.0 | | | 0.0 | 0.0 | 0.0 | 0.0 | 0.0 | | | 99.5 |
| 16hb-10692.5 | 10,692.5 | 1.5 | 0.0 | 0.2 | 2.4 | 0.0 | 0.8 | 90.7 | 2.0 | 0.3 | 0.9 | 0.1 | 0.4 | 0.0 | | | 0.0 | 0.0 | 0.0 | 0.0 | 0.0 | | | 99.6 |
| 17G-10698.5 | 10,698.5 | 2.5 | 0.1 | 0.5 | 5.4 | 0.0 | 1.0 | 88.2 | 2.9 | 0.2 | 1.1 | 0.2 | 0.1 | 0.0 | | | 0.0 | 0.0 | 0.0 | 0.0 | 0.0 | | | 99.7 |
| 18G-10704.5 | 10,704.5 | 1.5 | 0.3 | 0.5 | 3.6 | 0.0 | 0.5 | 86.7 | 4.7 | 0.5 | 1.1 | 0.3 | 0.2 | 0.0 | | | 0.0 | 0.0 | 0.0 | 0.0 | 0.0 | | | 99.2 |
| 19G-10707.5 | 10,707.5 | 2.5 | 0.1 | 0.5 | 4.9 | 0.0 | 0.7 | 83.4 | 3.4 | 0.3 | 1.2 | 0.3 | 0.2 | 0.0 | | | 0.0 | 0.0 | 0.0 | 0.0 | 0.0 | | | 99.3 |
| 20G-10710.5 | 10,710.5 | 2.7 | 0.2 | 0.6 | 5.4 | 0.0 | 0.8 | 87.5 | 1.1 | 0.1 | 1.3 | 0.2 | 0.2 | 0.0 | | | 0.0 | 0.0 | 0.0 | 0.0 | 0.0 | | | 99.0 |
| 21G-10719.5 | 10,719.5 | 2.4 | 0.3 | 0.5 | 4.6 | 0.0 | 1.0 | 85.3 | 2.7 | 0.3 | 1.3 | 0.3 | 0.2 | 0.0 | | | 0.0 | 0.0 | 0.0 | 0.0 | 0.0 | | | 99.4 |
| 22G-10725.5 | 10,725.5 | 3.9 | 0.2 | 0.7 | 2.6 | 0.1 | 2.2 | 85.4 | 3.4 | 0.4 | 1.3 | 0.2 | 0.2 | 0.0 | | | 0.0 | 0.0 | 0.0 | 0.0 | 0.0 | | | 99.2 |
| 24G-10731.5 | 10,731.5 | 3.7 | 0.1 | 0.7 | 7.7 | 0.1 | 3.2 | 75.8 | 1.8 | 0.4 | 5.1 | 0.3 | 0.8 | 0.0 | | | 0.0 | 0.0 | 0.0 | 0.0 | 0.0 | | | 99.6 |
| 25G-10737.5 | 10,737.5 | 5.2 | 0.0 | 0.3 | 4.5 | 0.1 | 5.4 | 79.8 | 0.4 | 0.2 | 3.6 | 0.2 | 0.1 | 0.0 | | | 0.0 | 0.0 | 0.0 | 0.0 | 0.0 | | | 99.8 |
| Type | Depth (ft) | Quartz | Albite | K-Feldspar | Mica-Ill-Smec | Chlorite | Kaolinite | Calcite | Dolomite | Siderite | Pyrite | Anatase | Apatite | Barite | Anhydrite | Halite | Hematite | Smectite | Illite | Chlorite | Magnesite | Gypsum | Water | |

FIG. 6B

ALL wt % ARE ADJUSTED from XRD IN FIG. 6A WHEN KEROGEN WT % IS ENTERED ON RIGHT

| Type | Depth | Quartz | Albite | K-Spar | Ill/Sme | Fe-Chlorite | Kaolinite | Calcite | Ca.5Mg.5CO3 | Siderite | Pyrite | Anatase | Apatite | Barite | Anhydrite | Halite | Hematite | Smectite | Illite | Chlorite | Magnesite | Gypsum | Celestine | Kerogen | DENSITY | SUM |
|---|---|---|---|---|---|---|---|---|---|---|---|---|---|---|---|---|---|---|---|---|---|---|---|---|---|---|
| 01G-10491P5 | 10,491.5 | 3.6 | 0.0 | 1.1 | 13.6 | 0.5 | 11.7 | 60.4 | 0.7 | 0.3 | 4.9 | 0.5 | 0.1 | 0.0 | 0.0 | 0.0 | 0.0 | 0.0 | 0.0 | 0.0 | 0.0 | 0.0 | 0.0 | 2.1 | 2.72 | 99.4 |
| 02G-10500P5 | 10,500.5 | 6.5 | 0.0 | 1.0 | 12.6 | 0.0 | 8.4 | 63.4 | 0.3 | 0.1 | 4.3 | 0.3 | 0.1 | 0.0 | 0.0 | 0.0 | 0.0 | 0.0 | 0.0 | 0.0 | 0.0 | 0.0 | 0.0 | 2.6 | 2.70 | 99.5 |
| 03G-10509P5 | 10,509.5 | 7.5 | 0.0 | 1.2 | 12.8 | 0.0 | 9.0 | 60.4 | 0.5 | 0.2 | 4.8 | 0.4 | 0.0 | 0.0 | 0.0 | 0.0 | 0.0 | 0.0 | 0.0 | 0.0 | 0.0 | 0.0 | 0.0 | 2.4 | 2.72 | 99.0 |
| 04G-10524 | 10,524.0 | 5.8 | 0.1 | 1.2 | 13.0 | 0.2 | 6.8 | 66.1 | 0.4 | 0.2 | 4.3 | 0.5 | 0.1 | 0.0 | 0.0 | 0.0 | 0.0 | 0.0 | 0.0 | 0.0 | 0.0 | 0.0 | 0.0 | 1.1 | 2.74 | 99.7 |
| 05G-10530 | 10,530.0 | 6.2 | 0.2 | 1.2 | 12.1 | 0.7 | 5.4 | 66.7 | 0.2 | 0.3 | 4.3 | 0.4 | 0.2 | 0.0 | 0.0 | 0.0 | 0.0 | 0.0 | 0.0 | 0.0 | 0.0 | 0.0 | 0.0 | 2.0 | 2.72 | 99.7 |
| 06G-10536.5 | 10,536.5 | 6.0 | 0.1 | 0.9 | 14.3 | 0.2 | 5.4 | 64.6 | 0.3 | 0.3 | 4.3 | 0.4 | 0.1 | 0.0 | 0.0 | 0.0 | 0.0 | 0.0 | 0.0 | 0.0 | 0.0 | 0.0 | 0.0 | 2.9 | 2.68 | 99.7 |
| 07G-10548 | 10,548.0 | 6.2 | 0.1 | 0.7 | 11.4 | 0.0 | 4.7 | 69.3 | 1.4 | 0.4 | 2.4 | 0.2 | 0.2 | 0.0 | 0.0 | 0.0 | 0.0 | 0.0 | 0.0 | 0.0 | 0.0 | 0.0 | 0.0 | 1.9 | 2.71 | 99.2 |
| 08G-10561 | 10,561.0 | 1.7 | 0.0 | 0.3 | 1.2 | 0.3 | 0.6 | 85.6 | 7.8 | 0.5 | 0.4 | 0.1 | 0.3 | 0.0 | 0.0 | 0.0 | 0.0 | 0.0 | 0.0 | 0.0 | 0.0 | 0.0 | 0.0 | 0.8 | 2.77 | 99.5 |
| 09G-10590 | 10,590.0 | 0.2 | 0.0 | 0.1 | 0.5 | 0.2 | 0.2 | 93.5 | 4.1 | 0.4 | 0.4 | 0.2 | 0.6 | 0.0 | 0.0 | 0.0 | 0.0 | 0.0 | 0.0 | 0.0 | 0.0 | 0.0 | 0.0 | 0.2 | 2.73 | 99.7 |
| 10G-10605 | 10,605.0 | 0.6 | 0.0 | 0.0 | 0.7 | 0.2 | 0.8 | 87.5 | 4.2 | 0.3 | 0.7 | 0.1 | 0.4 | 0.0 | 0.0 | 0.0 | 0.0 | 0.0 | 0.0 | 0.0 | 0.0 | 0.0 | 0.0 | 3.0 | 2.66 | 99.3 |
| 11G-10623 | 10,623.0 | 1.1 | 0.0 | 0.0 | 1.6 | 0.3 | 0.6 | 89.2 | 4.0 | 0.2 | 0.7 | 0.2 | 0.1 | 0.0 | 0.0 | 0.0 | 0.0 | 0.0 | 0.0 | 0.0 | 0.0 | 0.0 | 0.0 | 3.5 | 2.66 | 99.3 |
| 12G-10644P5 | 10,644.5 | 2.0 | 0.1 | 0.6 | 2.2 | 0.2 | 0.8 | 86.3 | 3.3 | 0.2 | 0.6 | 0.2 | 0.1 | 0.0 | 0.0 | 0.0 | 0.0 | 0.0 | 0.0 | 0.0 | 0.0 | 0.0 | 0.0 | 2.7 | 2.62 | 99.4 |
| 13G-10665P5 | 10,665.5 | 2.4 | 0.0 | 0.3 | 3.5 | 0.1 | 0.3 | 87.0 | 4.0 | 0.2 | 0.8 | 0.2 | 0.2 | 0.0 | 0.0 | 0.0 | 0.0 | 0.0 | 0.0 | 0.0 | 0.0 | 0.0 | 0.0 | 1.5 | 2.70 | 99.5 |
| 14G-10671P5 | 10,671.5 | 1.9 | 0.1 | 0.9 | 5.8 | 0.0 | 1.9 | 78.0 | 2.0 | 0.5 | 2.7 | 0.2 | 0.4 | 0.0 | 0.0 | 0.0 | 0.0 | 0.0 | 0.0 | 0.0 | 0.0 | 0.0 | 0.0 | 5.8 | 2.59 | 99.5 |
| 15G-10677P5 | 10,677.5 | 2.7 | 0.1 | 0.4 | 10.0 | 0.1 | 2.5 | 68.8 | 1.9 | 0.2 | 4.3 | 0.3 | 0.2 | 0.0 | 0.0 | 0.0 | 0.0 | 0.0 | 0.0 | 0.0 | 0.0 | 0.0 | 0.0 | 7.5 | 2.56 | 99.5 |
| 16h-10692.5 | 10,692.5 | 1.5 | 0.0 | 0.0 | 0.9 | 0.2 | 0.8 | 86.7 | 1.6 | 0.2 | 0.9 | 0.1 | 0.4 | 0.0 | 0.0 | 0.0 | 0.0 | 0.0 | 0.0 | 0.0 | 0.0 | 0.0 | 0.0 | 4.4 | 2.61 | 99.6 |
| 17G-10698P5 | 10,698.5 | 2.2 | 0.1 | 0.6 | 2.3 | 0.1 | 0.2 | 90.4 | 2.1 | 0.5 | 0.4 | 0.2 | 0.2 | 0.0 | 0.0 | 0.0 | 0.0 | 0.0 | 0.0 | 0.0 | 0.0 | 0.0 | 0.0 | 2.2 | 2.66 | 99.7 |
| 18G-10701P5 | 10,701.5 | 1.4 | 0.0 | 0.4 | 1.1 | 0.1 | 0.5 | 82.3 | 2.7 | 0.3 | 1.2 | 0.1 | 0.3 | 0.0 | 0.0 | 0.0 | 0.0 | 0.0 | 0.0 | 0.0 | 0.0 | 0.0 | 0.0 | 6.7 | 2.55 | 99.4 |
| 19G-10704P5 | 10,704.5 | 2.2 | 0.0 | 0.4 | 3.4 | 0.0 | 1.0 | 76.5 | 1.9 | 0.4 | 1.1 | 0.1 | 0.4 | 0.0 | 0.0 | 0.0 | 0.0 | 0.0 | 0.0 | 0.0 | 0.0 | 0.0 | 0.0 | 11.7 | 2.41 | 99.3 |
| 20G-10707P5 | 10,707.5 | 1.8 | 0.0 | 0.7 | 4.9 | 0.0 | 1.0 | 75.7 | 4.2 | 0.2 | 1.0 | 0.2 | 0.2 | 0.0 | 0.0 | 0.0 | 0.0 | 0.0 | 0.0 | 0.0 | 0.0 | 0.0 | 0.0 | 8.3 | 2.48 | 99.3 |
| 21G-10710P5 | 10,710.5 | 2.5 | 0.2 | 0.5 | 3.7 | 0.1 | 2.0 | 79.2 | 2.5 | 0.3 | 1.2 | 0.2 | 0.4 | 0.0 | 0.0 | 0.0 | 0.0 | 0.0 | 0.0 | 0.0 | 0.0 | 0.0 | 0.0 | 8.8 | 2.49 | 99.1 |
| 22G-10719P5 | 10,719.5 | 2.8 | 0.2 | 0.7 | 4.3 | 0.0 | 1.0 | 80.6 | 1.8 | 0.4 | 1.2 | 0.2 | 0.8 | 0.0 | 0.0 | 0.0 | 0.0 | 0.0 | 0.0 | 0.0 | 0.0 | 0.0 | 0.0 | 7.2 | 2.54 | 99.4 |
| 23G-10725P5 | 10,725.5 | 1.8 | 2.0 | 0.3 | 3.7 | 0.1 | 2.0 | 72.4 | 2.5 | 0.4 | 4.9 | 0.2 | 0.2 | 0.0 | 0.0 | 0.0 | 0.0 | 0.0 | 0.0 | 0.0 | 0.0 | 0.0 | 0.0 | 5.8 | 2.58 | 99.6 |
| 24G-10731P5 | 10,731.5 | 3.5 | 1.0 | 0.7 | 7.3 | 0.0 | 3.0 | 74.2 | 1.8 | 0.2 | 1.2 | 0.2 | 0.1 | 0.0 | 0.0 | 0.0 | 0.0 | 0.0 | 0.0 | 0.0 | 0.0 | 0.0 | 0.0 | 4.5 | 2.65 | 99.1 |
| 25G-10737P5 | 10,737.5 | 5.2 | 0.0 | 0.3 | 4.5 | 0.1 | 5.4 | 79.5 | 0.4 | 0.2 | 3.6 | 0.2 | 0.1 | 0.0 | 0.0 | 0.0 | 0.0 | 0.0 | 0.0 | 0.0 | 0.0 | 0.0 | 0.0 | 0.4 | 2.75 | 99.8 |

SOURCE PRODUCTIVITY ASSAY INTEGRATING PYROLYSIS DATA AND X-RAY DIFFRACTION DATA

FIELD

The disclosure relates to a source productivity assay integrating pyrolysis data and X-ray diffraction data.

BACKGROUND

It is often desirable to determine the volume, chemistry, density, and hydrocarbon phases that could be generated from a source rock. This information can be used in the calibration of basin models that emulate the kinetics and thermodynamics surrounding the burial history of the source rock. The information can also be used assess economic risks associated with drilling and completing unconventional reservoirs. In general, analytical laboratory protocols are used to acquire or measure properties from a source rock and/or a produced fluid from the source rock.

SUMMARY

The disclosure relates to a source productivity assay integrating pyrolysis data and X-ray diffraction data. The assay can provide a relatively fast and/or relatively inexpensive way to predict the productivity of a source, such as a source rock. In some embodiments, the assay can be used to obtain information about the productivity of a source rock reservoir after the reservoir has been completely drilled. In certain embodiments, the assay can be used for exploration purposes (e.g., before a reservoir is completely drilled).

In some embodiments, the assay can be used to provide information relating to what might otherwise be unknown parameters in a basin model for simulating the burial history of the basin and its relationship to the timing, generation and/or migration of fluid volumes generated from source rocks as they are buried. In certain embodiments, a regional basin model with this information can be used to assess the relative risk of various regions of the basin, which can be used to localize regions for drilling that may produce a greater quantity and/or quality of hydrocarbons. This information can be used for exploration and/or for determining the thermogenic maturity of source rock, which can be useful in various applications.

In some embodiments, the assay can be used to investigate a source rock to determine a volume of hydrocarbons in place, a gas to oil ratio, and/or an intra-kerogen porosity. In certain embodiments, the assay can be used to determine information relating to the maturity of the source rock. This information can be used predict fluid densities of the source rock, which in turn can be used to determine one or more of the properties noted in the preceding sentence.

In first aspect, the disclosure provides a method that includes determining at least one parameter based on a combination of pyrolysis data for a source rock and X-ray diffraction (XRD) data for the source rock.

In some embodiments, the parameter includes a gas/oil ratio.

In some embodiments, the method is used to evaluate a productivity of the source rock.

In some embodiments, the method further includes determining a ratio of an oil specific gravity of the source rock to a density of the source rock (API) using the equation $$API = Ln(\% Ro/0.2534)/.0345,$$

where % Ro is a maturity of the rock sample.

In some embodiments, the method further includes determining a ratio of saturated fluids to aromatic fluids in the source rock (Sat/Aro) using the equation $$Sat/Aro = (\% Ro/.7842)^{(1/0.3571)}.$$

In some embodiments, the method further includes determining a percent loss of a $C_{15+}$ fraction of bitumen of the rock source using the equation $$\% \text{ Loss } n\text{-}C_{15+} = API/7.2379^{(1/.4508)}.$$

In some embodiments, the method further includes determining a corrected milligrams of distillable hydrocarbon of the rock source per gram of the rock source ($S1_{corr}$) using the equation $$S1_{corr} = S1_o/(1-(\% \text{ Loss}/100)),$$

where $S1_o$ is an original value of the milligrams of distillable hydrocarbon of the rock source per gram of the rock source.

In some embodiments, the method further includes determining a percent loss of a $C_{15+}$ fraction of bitumen of the rock source using the equation $$\% \text{ Loss } n\text{-}C_{15+} = API/7.2379^{(1/.4508)}.$$

In some embodiments, the method is used to determine hydrocarbons in place of the source rock.

In a second aspect, the disclosure provides a method of evaluating a source rock, wherein the method includes determining a ratio of an oil specific gravity of the source rock to a density of the source rock (API) using the equation $$API = Ln(\% Ro/0.2534)/.0345,$$

where % Ro is a maturity of the rock sample.

In a third aspect, the disclosure provides a method of evaluating a source rock, wherein the method includes determining a ratio of saturated fluids to aromatic fluids in the source rock (Sat/Aro) using the equation $$Sat/Aro = (\% Ro/.7842)^{(1/0.3571)},$$

where % Ro is a maturity of the rock sample.

In a fourth aspect, the disclosure provides a method of evaluating a source rock, wherein the method includes determining a percent loss of a $C_{15+}$ fraction of bitumen of the rock source using the equation $$\% \text{ Loss } n\text{-}C_{15+} = API/7.2379^{(1/.4508)},$$

where API is a ratio of an oil specific gravity of the source rock to a density of the source rock.

In a fifth aspect, the disclosure provides a method of evaluating a source rock, which includes determining a corrected milligrams of distillable hydrocarbon of the rock source per gram of the rock source ($S1_{corr}$) using the equation $$S1_{corr} = S1_o/(1-(\% \text{ Loss}/100)),$$

where $S1_o$ is an original value of the milligrams of distillable hydrocarbon of the rock source per gram of the rock source and (% Loss/100) is scales the loss value to a fraction.

In a sixth aspect, the disclosure provides one or more machine-readable hardware storage devices including instructions that are executable by one or more processing devices to perform operations that include a method disclosed herein.

In a seventh aspect, the disclosure provides a system that includes one or more processing devices, and one or more machine-readable hardware storage devices that include instructions that are executable by the one or more processing devices to perform operations including a method disclosed herein.

BRIEF DESCRIPTION OF THE FIGURES

FIGS. 6A and 6B are mineral to element calculators used to compute bulk density and other formation given inputs of XRD and wt % kerogen.

DETAILED DESCRIPTION

Figure 1:
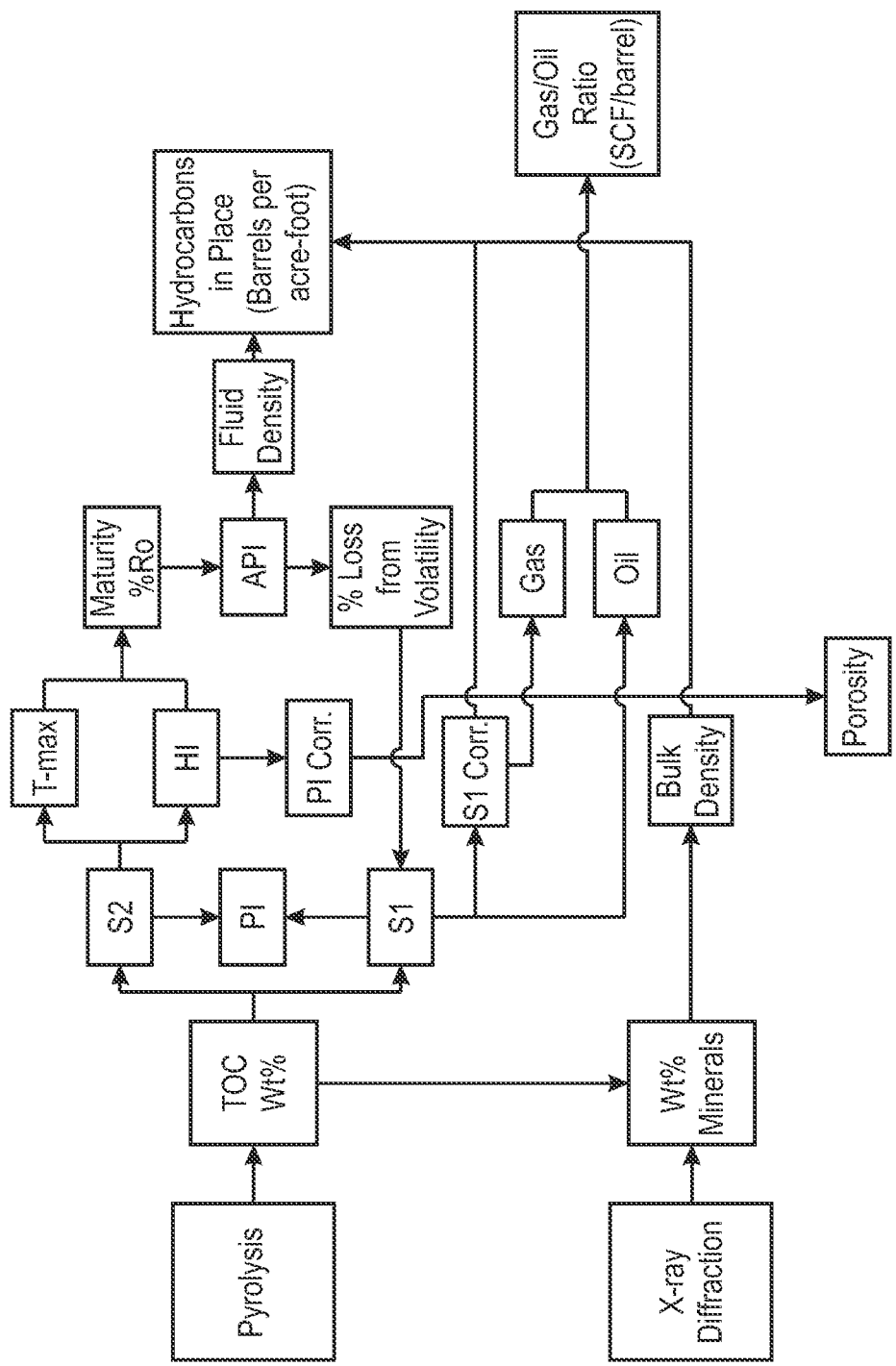
FIG. 1 is a schematic flow diagram of an assay.

FIG. 1 is a schematic flow diagram of an assay 1000 that is a source productivity assay integrating pyrolysis data and X-ray diffraction data. The following is a legend for some of the parameters in FIG. 1. TOC is the total organic carbon (wt %). S1 is the milligrams of distillable hydrocarbon per gram of rock (mgHC/gm rock). S2 is the remaining hydrocarbon generative potential of kerogen (mg/HC/gm rock). P1 is the productivity index=S1/(S1+S2). HI is the hydrogen index=S2/TOC*100. T-max is the maximum temperature of S2 (° C.). Maturity (% Ro) is the percentage of vitrinite reflectance in oil equivalent calculated from T-max or HI. API is the oil specific gravity/density. % loss from Volatility is the percentage loss of hydrocarbon due to volatility. S1 Corr is S1 corrected for losses due to volatility. Hydrocarbons in Place is the Barrels per acre-foot (barrel/ft$^3$). Gas is the computed gas from S1 corrected (standard cubic foot, SCF). Oil is the computed oil from S1 (stock tank barrel, STB). Gas/Oil ratio is the computed gas to oil ratio from S1 corrected (cubic feet per barrel, ft$^3$/barrel). PI Corr is the productivity index corrected (computed from HI). Bulk Density is the bulk density of the rock (gm/cc). Hydrocarbon Fluid Density is the oil density (gm/cc). Porosity is the computed porosity from HI (Km/sec).

In general, pyrolysis is a method of measure organic matter in a source rock. Generally, the method includes introducing a sample of the source of known mass into a sealed oven, which is programmed to heat the sample at a predetermined rate of increasing temperature until a predetermined temperature, such as 650° C., is reached. Higher or lower final temperatures can be used as appropriate. For example, the final temperature can be up to 850° C. if pyrolysis is being used to determine pyrobitumen and carbonate mineralogy.

As the temperature is increased, gases emitted by the sample are carried away from the sample by a gas stream (e.g., a stream of nitrogen or helium). The gas stream is subsequently split so that a portion of the gas stream reaches a flame ionization detector to measure hydrogen ($H_2$) emitted by the sample, and another portion of the gas stream reaches a thermal conductivity detector to measure the carbon dioxide ($CO_2$) emitted by the sample. Thus, the method provides, as a function of temperature, the amount of hydrogen and carbon dioxide emitted by the sample.

Figure 2:
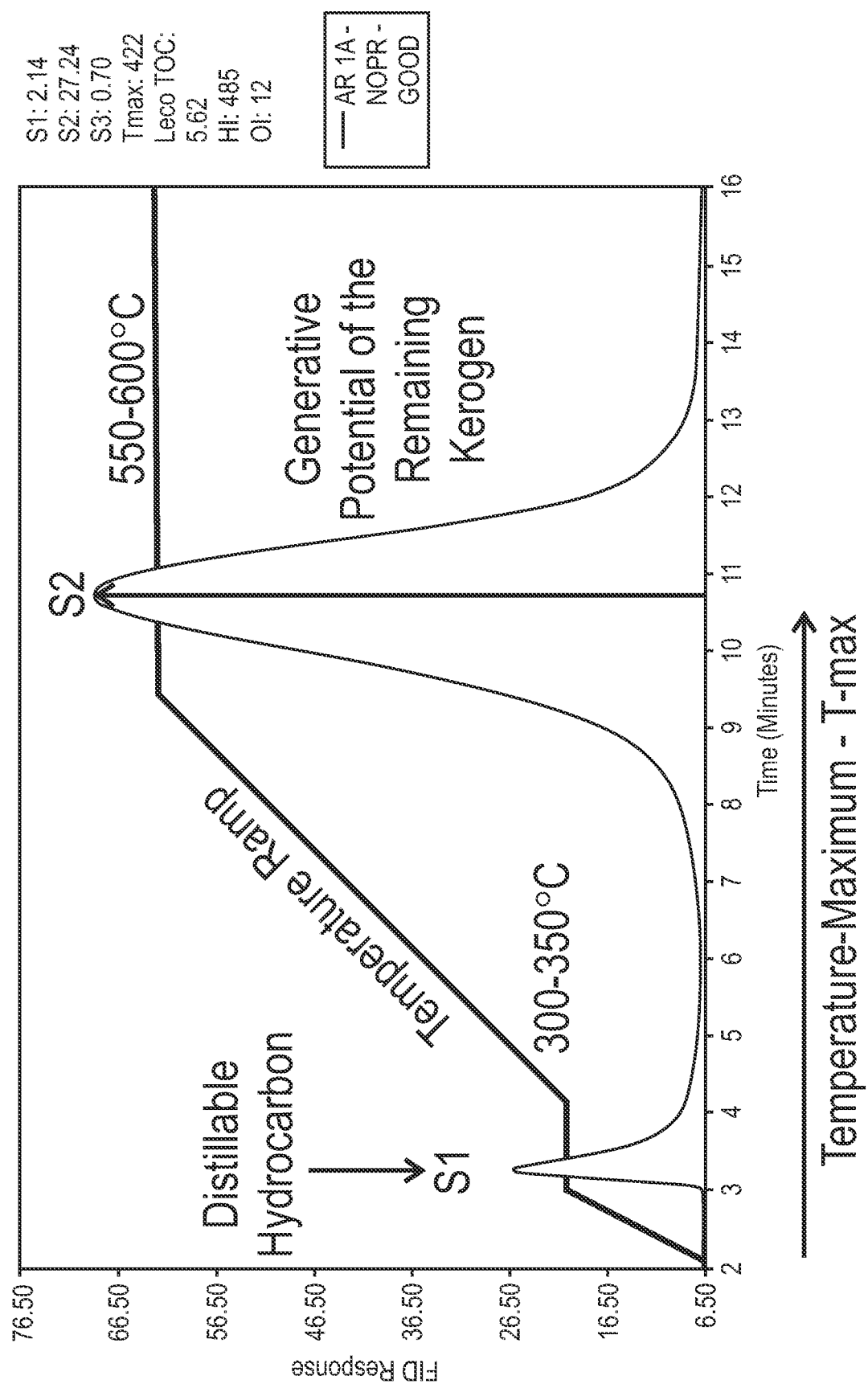
FIG. 2 is a pyrogram.

FIG. 2 depicts an example of a pyrogram 2000. As shown in FIG. 2, upon reaching a threshold temperature in the region of 300-350° C., a significant amount of hydrogen is recorded. This hydrogen evolves from the combustion of distillable hydrocarbon in the rock, which is generated by the kerogen in the sample depending upon its stage of transformation. This hydrogen is labelled S1 in FIG. 2. S1 is calculated by integrating the area under the S1 peak, with the total representing the milligrams of distillable hydrocarbon per gram of rock (mgHC/gm rck) measured. As the temperature is increased beyond 350° C., another threshold is reached in the region of 550-600° C. where more hydrogen evolves from the rock. This hydrogen labelled S2 in FIG. 2. S2 is the amount hydrocarbon that would be generated if the remaining hydrocarbon generative potential of the kerogen for a given stage of transformation was converted into hydrocarbons. The maximum temperature at which this maximum potential is reached is also recorded and called a T-max value. S2 is calculated by integrating the area under the S2 peak as mgHC/gm rck, similar to S1. S1 and S2 are part of the generative part of the total organic carbon in the kerogen in source rocks in weight percent (wt %).

The pyrolysis results are used to determine the stage of transformation of a source rock conversion into hydrocarbons as a function of maturity (% Ro). Because S1 and S2 are determined in mg HC per gm of rock, they can be used to determine the fluid properties or the remaining mass of hydrocarbons that have been produced or have the potential to be produced versus a mass of rock, as a function of maturity. This then allows for the upscaling of these properties to describe that expected at the scale of a source rock reservoir. Maturity can be determined from pyrolysis data via a T-max equation or a hydrogen index equation (HI=S2/TOC*100). Maturity can also be qualitatively determined by the productivity index (PI=S1/(S1+S2)) and even inferred from other measurements apart from pyrolysis.

The bulk H/C composition of kerogen thus can be described according to the following equation.

$$\text{Total H/C} = \% \text{ Liptinite (H/C)} + \% \text{ Virinite (H/C)} + \% \text{ Inertinite (H/C)}$$

When kerogens of variable H/C composition, composing source rocks, are thermogenically transformed into hydrocarbons with burial, they lose H/C. It may be considered that they are losing their hydrocarbon volatility in the process and in turn producing hydrocarbons in the form of bitumen, which produces oil and gas. Relative to H/C of kerogen, the generation of oil and bitumen reaches a maximum some-where around peak maturity and then steadily declines as the remaining bitumen and oil is thermogenically cracked to gas during gas stage maturity.

As the H/C ratio decreases in the kerogen, so too does the S2. The S2 then, is analogous to that of the H/C of kerogen when it is used in a ratio against the measured TOC and scaled by 100 to provide HI. This means that the HI can be used as a maturity indicator. At the same time, the bitumen which is increasing with this transformation prior to reaching its maximum, can be tracked by comparing the change in S1 relative to the change in S2. The S1 is minimal in concentration similar to the bitumen at the immature stage, but, upon reaching peak maturity, where the amount of bitumen is at its maximum, the S1 steadily reaches a maximum relative to S2 and continues to increase thereafter through to late maturity, where the amount of bitumen decreases. Thus if the ratio of S1 to the sum of S1 and S2 is determined, a productivity index (PI) can be used as an indication of this progressive transformation which also can be plotted against the T-max reached from the S2 measured. Likewise, S1/TOC*100 can also provide an equivalent for tracking this transformation as a function of HI. The T-max values are thermal stress indicators of this transformation an have been used to compute an equivalent % Ro by Jarvie (2001). That value is used to determine maturity. Also, a specially developed equation using HI has also been developed as a way of determining maturity and for checking the validity of the % Ro Jarvie equation.

$$\% \text{ Ro} = .0180 * \text{T-max} - 7.16 \text{ (Jarvie, 2001)} \quad (1)$$

To compare to the equivalent % Ro from T-max, companion values are determined from that of HI using the equation which has been derived to compute an equivalent % Ro which is as follows.

$$\% \text{ Ro} = -.404 * \text{Ln(HI)} + 3.1359 \text{ (Jacobi, 2020)} \quad (2)$$

Figure 3A:
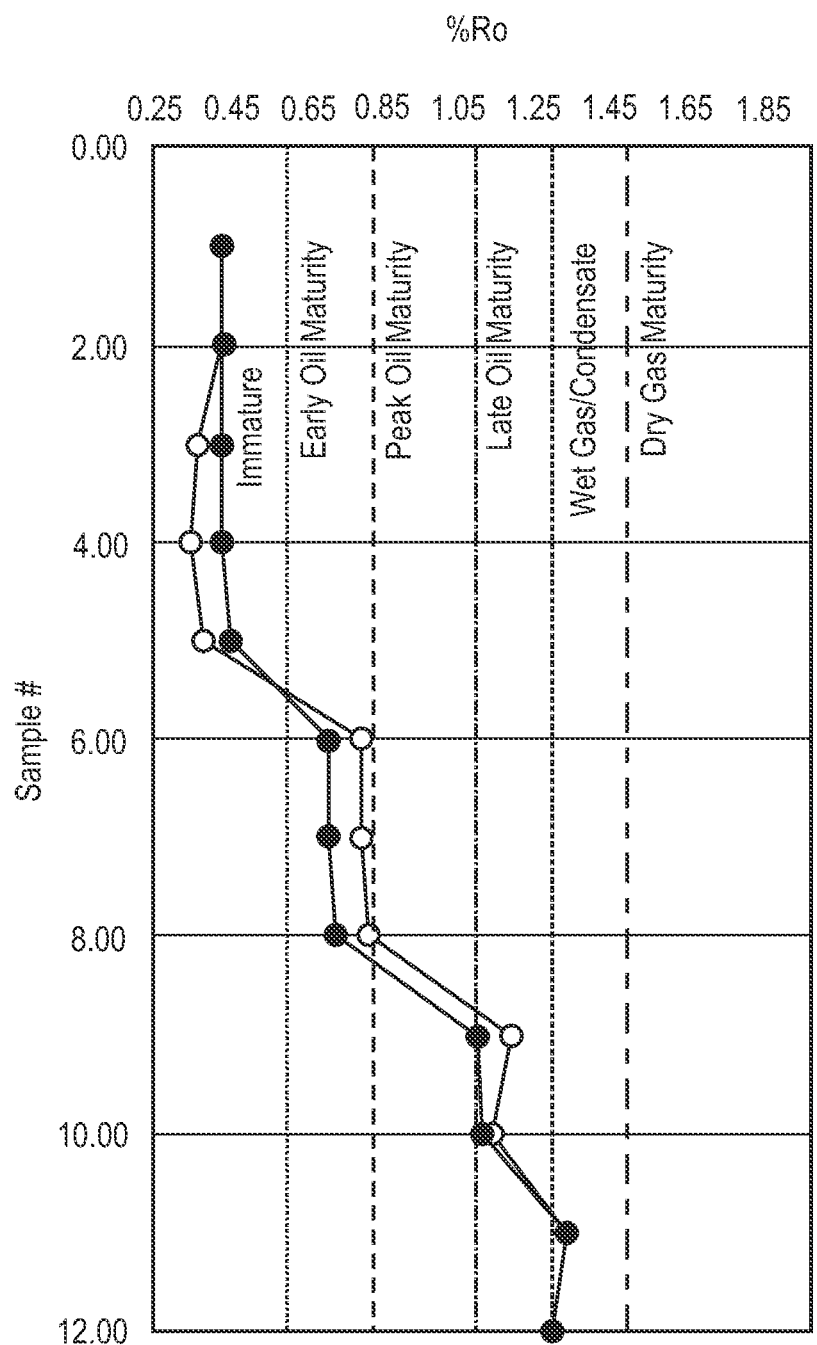
FIGS. 3A-3C are plots showing the estimate of maturity.
Figure 3B:
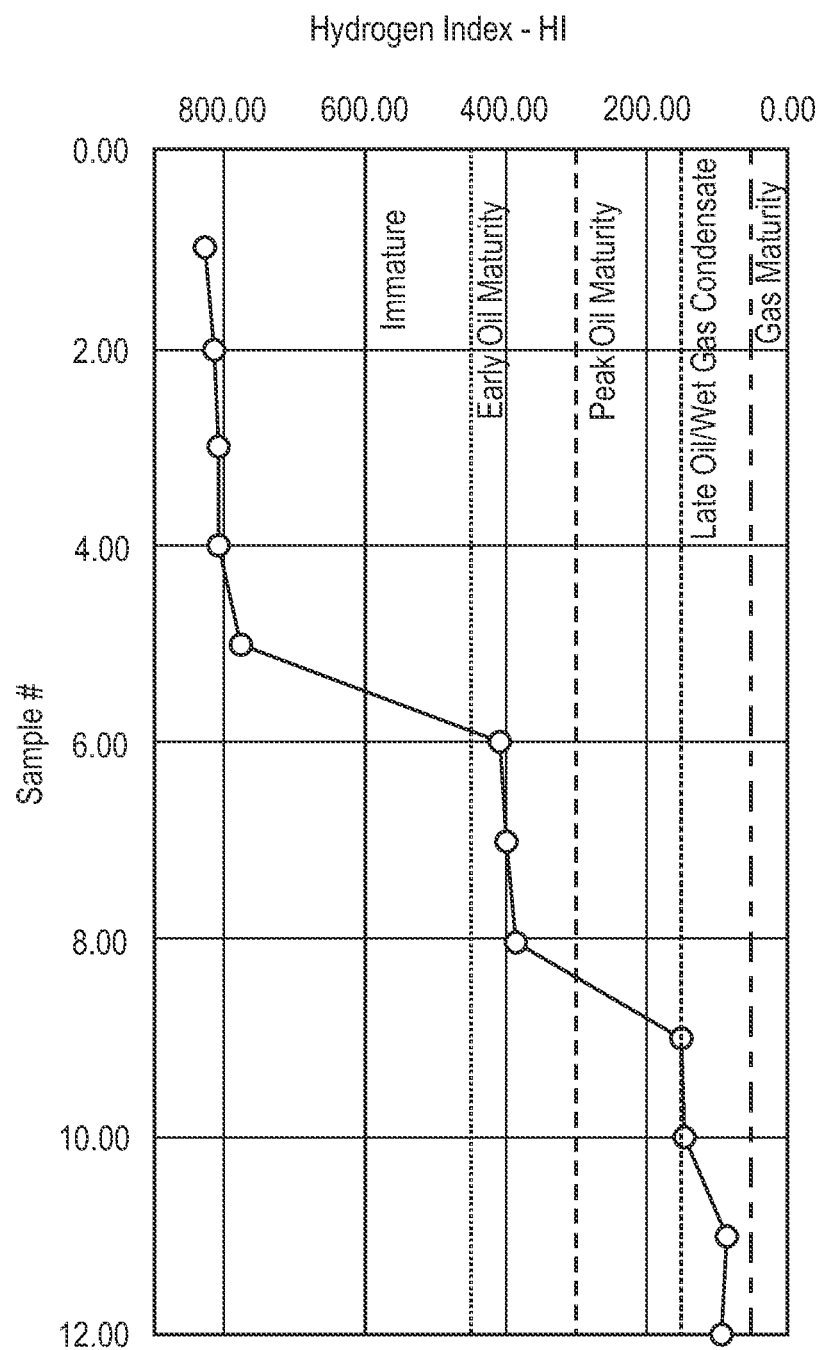
Figure 3C:
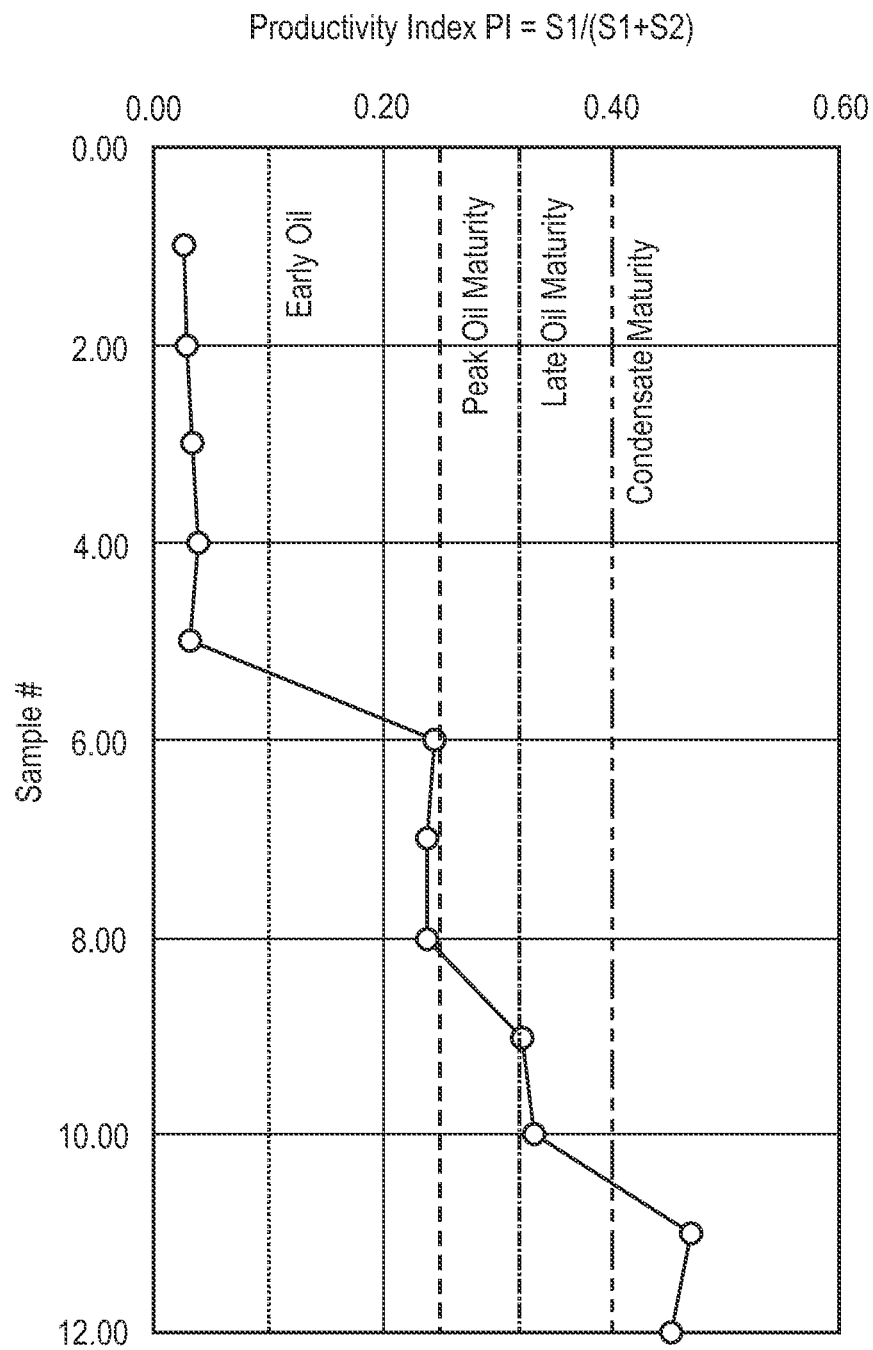

FIGS. 3A-3C show the estimate of maturity based on equations 1 and 2 and the productivity index for three samples. The % Ro maturity was determined for immature samples (samples 1-5), early oil maturity samples (samples 6-8), late oil maturity for samples (samples 9 and 10), and wet gas maturity samples (samples 11 and 12). % Ro computed from T-max are white those from HI are black. Both the productivity index and the HI indicators also suggest similar maturity trends.

While certain approaches to determining % Ro have been described, the disclosure is not limited to such approaches. Other approaches are known to those skilled in the art that can be used.

As can be seen, the producitivity index (PI) can be valuable for evaluating the equivalent % Ro from T-max and HI. The transformation represented by the PI value accompanies a change in fluid composition as well. As the kerogen loses hydrogen relative to carbon as represented by the decreasing HI and H/C ratio of the kerogen, the fluids generated become progressively lighter. This is demonstrated by an increase in saturates relative to the aromatics in the saturated/aromatic ratio (SARA) ternary in the bitumen and the produced oils. The produced oils also exhibit a change in density that corresponds to that transformation. This is measured according to the API, which is an assessment of the specific gravity of stock tank oil measured against that of water at 60° F. according to the following equation:

$$° \text{API} = 141.5/(\text{specific gravity } 60°/60° F.) - 131.5 \quad (3)$$

According to the disclosure, a transform has been developed to compute the saturate/aromatic ratio of the bitumen content as a function of maturity as an indication of what type of fluid that one could expect to generate. However, it is not used to determine the API simply because of the volatility issues concerning the S1 as the rock matures. Remembering, the S1 value measured from pyrolysis represents hydrocarbon fluids known as bitumen, it is also referred to as the n-C15+ fraction, meaning, the fraction of generated hydrocarbon compounds which has not volatilized or evaporated from the rock.

Unlike oil, which contains the whole range of normal alkanes from light to heavy, the bitumen in source rocks contains the heavier fractions of those components because the lighter molecules are lost. As a result, any transform developed from the saturate/aromatic ratio of bitumen may be hampered, as that volatility increases exponentially as the rock matures. The significance of the change in volatility of the hydrocarbons is discussed below. However, the main factor that drives this change in volatility is due to the density of the fluids which become lighter and lighter with increasing maturity. Therefore, according to the disclosure, the % Ro computed is initially used to determine the API and the saturate to aromatic ratio of the bitumen according to the following equation.

$$\text{API} = \text{Ln}(\% \text{ Ro}/0.2534)/.0345 \quad (4)$$

And, the corresponding saturate-aromatic ratio is computed using the following equation developed similar to the API equation presented.

$$\text{Sat/Aro} = (\% \text{ Ro}/.7842)^{(1/0.3571)} \quad (5)$$

Figure 4A:
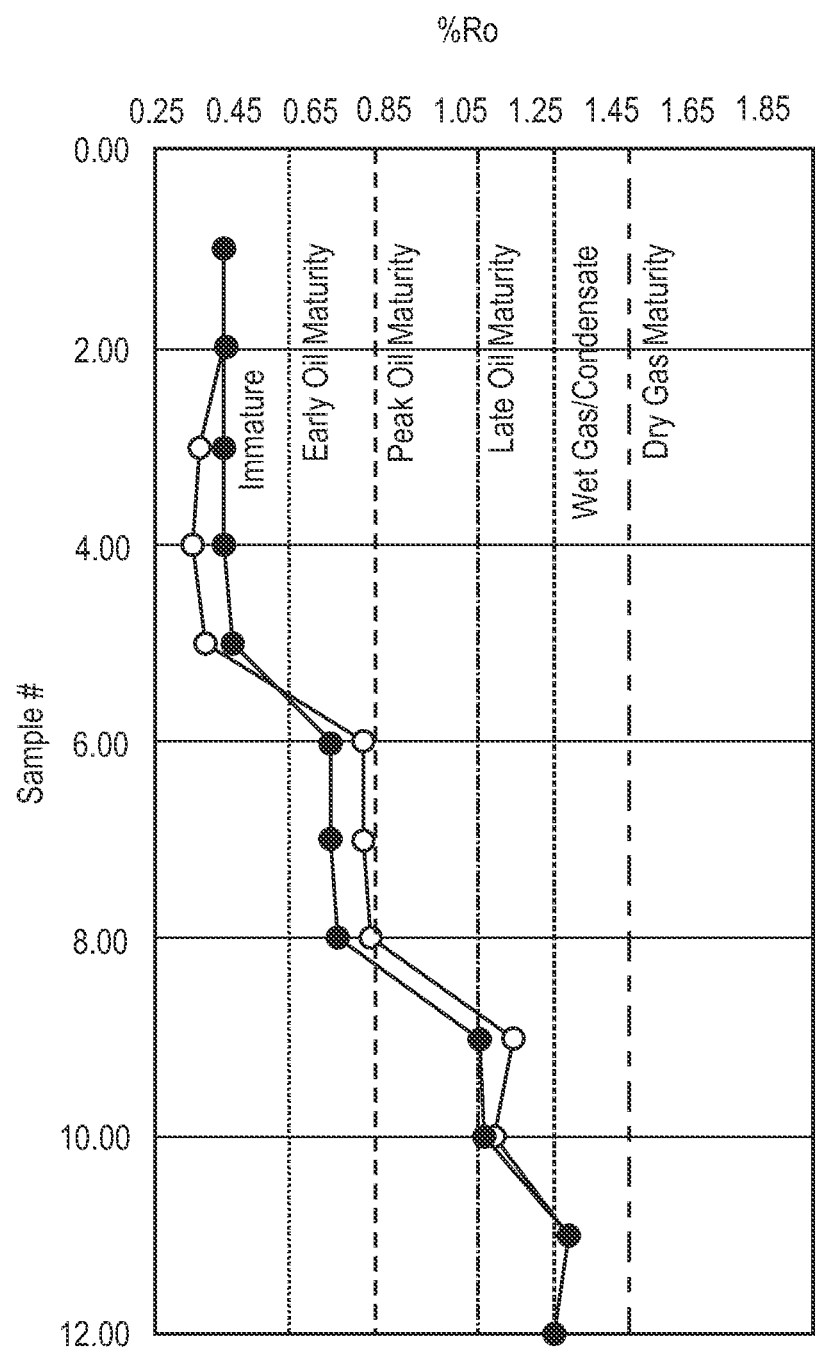
FIGS. 4A-4C are plots of % Ro-T-max and % Ro-HI (A), the computed API (B) and the saturate/aromatic ratio of the fluids (C).
Figure 4B:
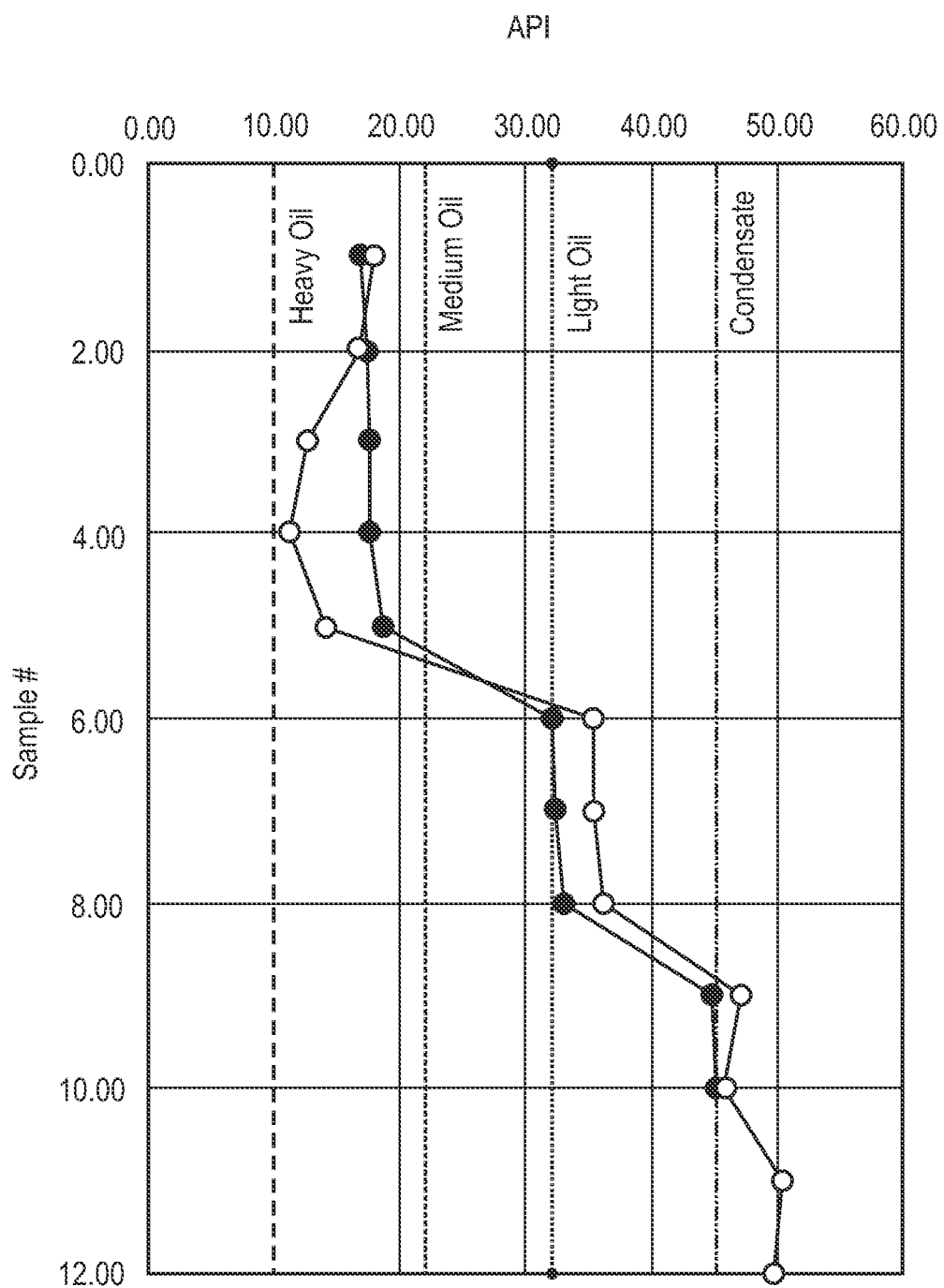
Figure 4C:
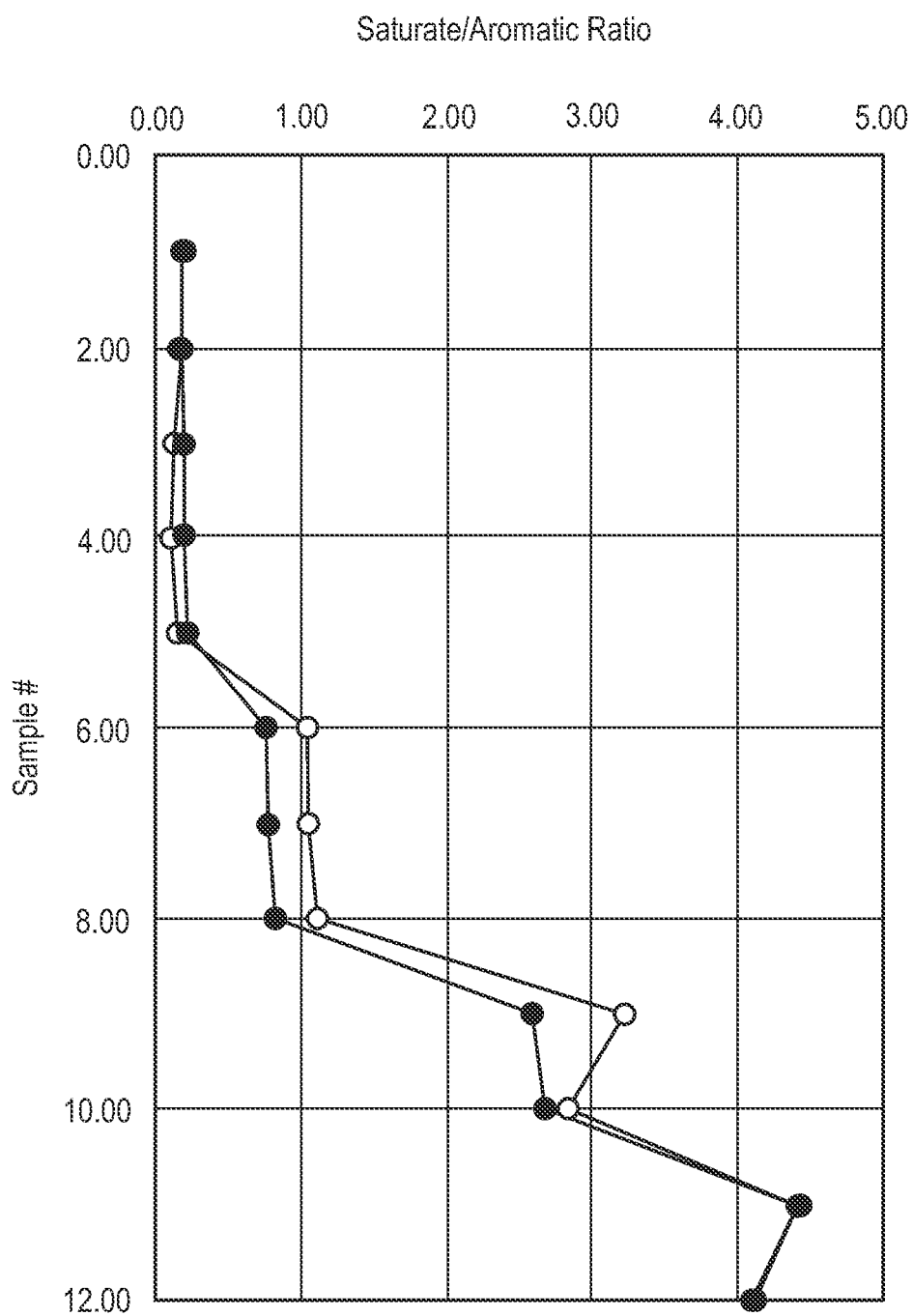

These equations were developed as a guide for monitoring the API of produced fluid relative to the maturity of the rock which was also confirmed by biomarker isomerization and kerogen aromaticity. FIGS. 4A-4C plot % Ro-T-max (white) and % Ro-HI (black) versus the computed API and the changing saturate/aromatic ratio of the fluids showing comparable fluid densities with the maturities estimated. There are significant differences in the fluid densities at the immature stage. Such heavy densities might suggest the % Ro-HI may be a more reliable indicator of maturity. FIGS. 4A-4C show that the fluid density based on the computed maturity from both T-Max and HI progressively decreases with increasing API number from heavy oil samples 1-5, to light oil samples 6-8, and then transitioning from light oil samples 9 and 10 to condensate for samples 11-12.

The volatility differences due to maturity, which inturn controls the density of fluid, is what causes the rock to lose hydrocarbons as it is brought to the surface, thus leaving behind the C15+ fraction, as the volatiles escape as the C15- fraction. The original S1 measured from pyrolysis can be corrected for that loss of the C15- fraction to determine the hydrocarbons in place. The percent mass lost of volatile hydrocarbons from the rock is determined according to the API established via the computed % Ro. The change in the potential loss via API can be seen by looking at the concentration trend of the GC chemistry of produced oils. The volume of the lighter ends versus the heavier fractions are steadily increasing with API. Thus a greater fraction will be lost from the rock based on that increasing concentration of volatiles.

Both the results from the recent equations were used to help develop the equation to predict the loss of the S1 from the source rock as a function of the change in volatility via the API computed earlier. However, the transform is exponential and is extrapolated back to the beginning of generation at a % Ro of 0.25. And, because the % Ro can be computed via the T-max derived value and the HI, two estimates are then computed in SPARK to provide a probable range. With this information the percent loss of hydrocarbon can be computed that has occurred due to this changing volatility according to the following equation:

$$\% \text{ Loss } n\text{-}C_{15-} = \text{API}/7.2379^{(1/.4508)} \quad (6)$$

Figure 5A:
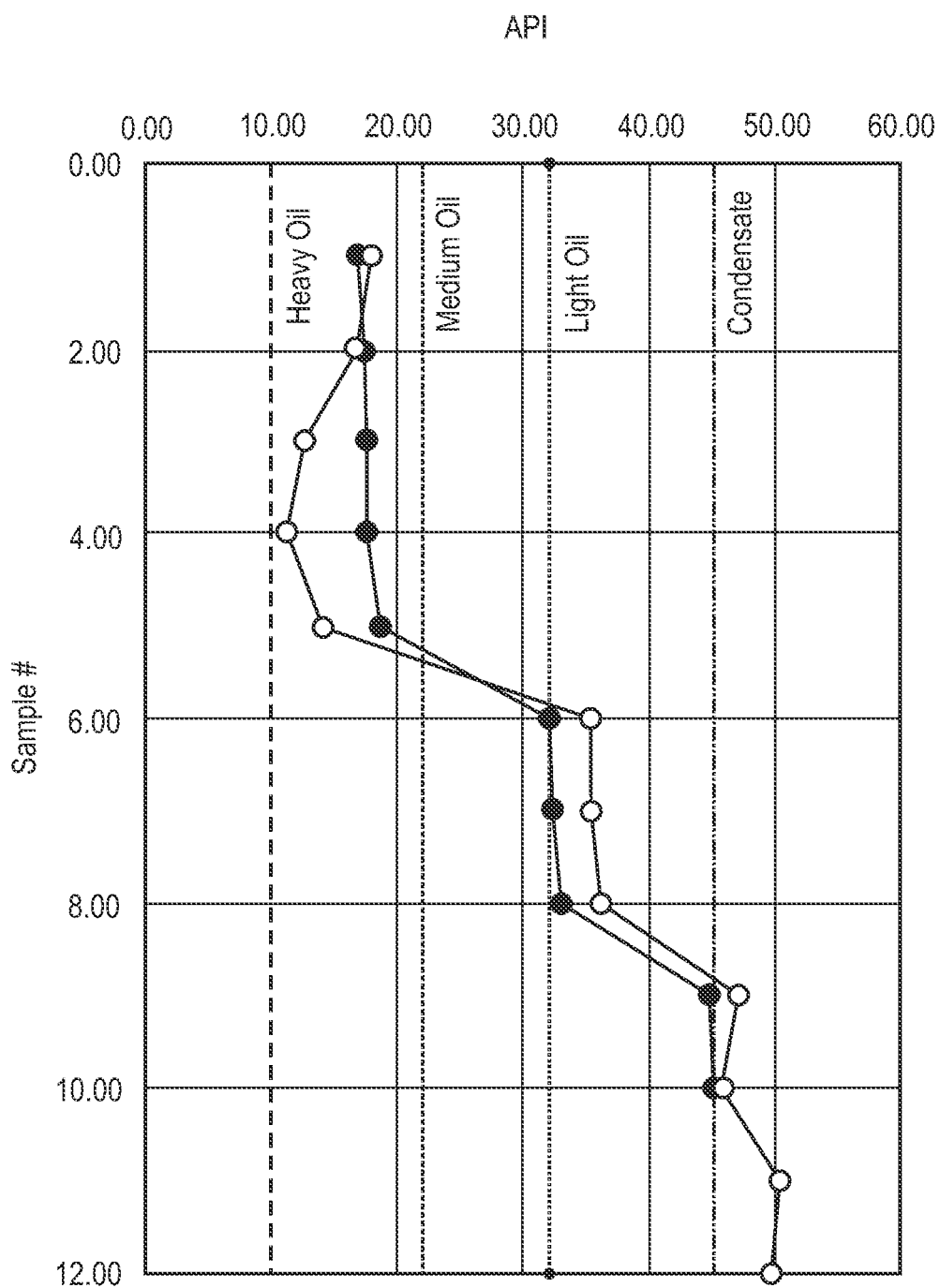
FIGS. 5A-5C are plots of the API (A), % loss computed that was used to correct the S1 value due to volatility (B) and a comparison of the uncorrected and corrected S1 (C).
Figure 5B:
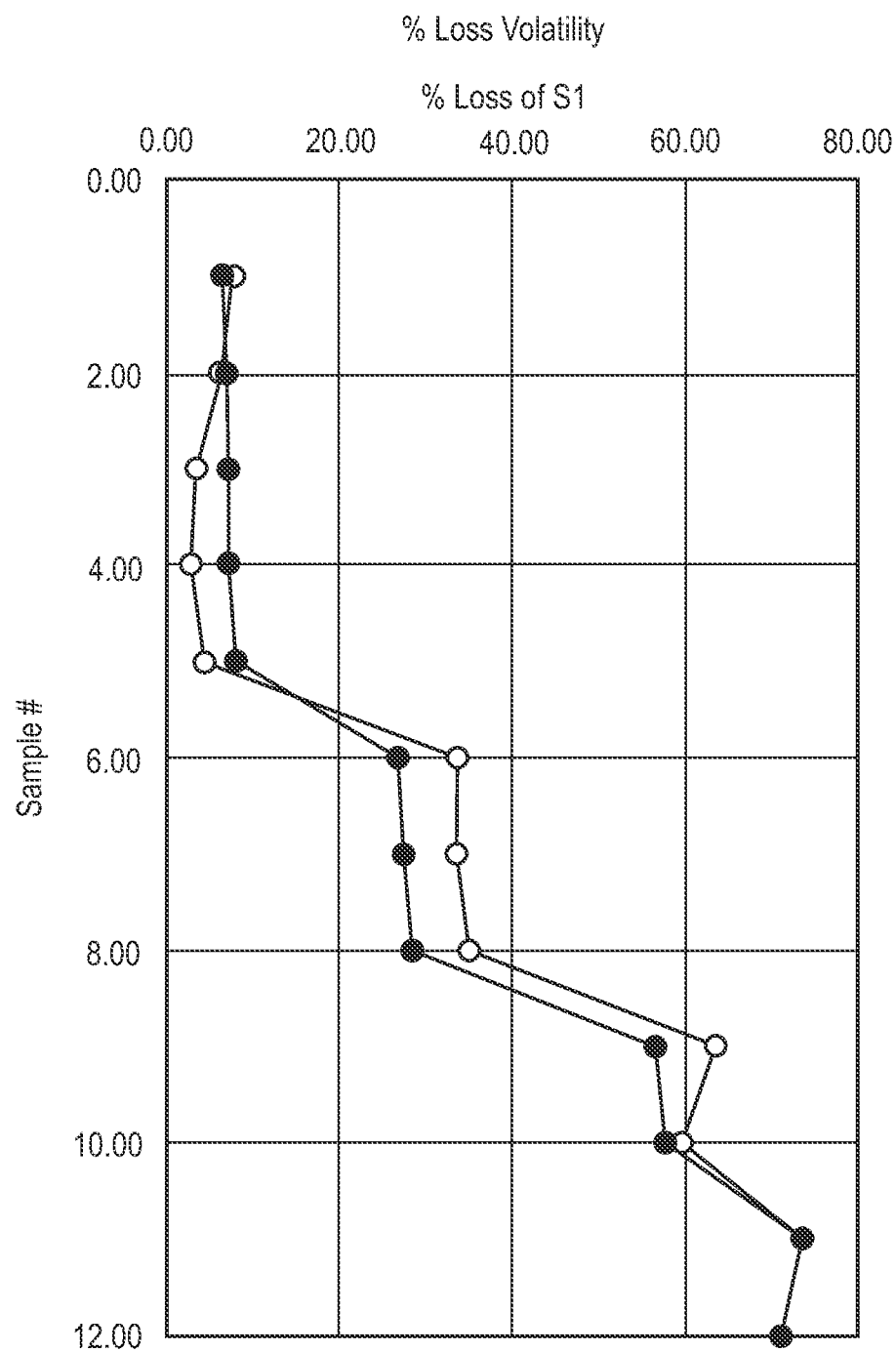
Figure 5C:
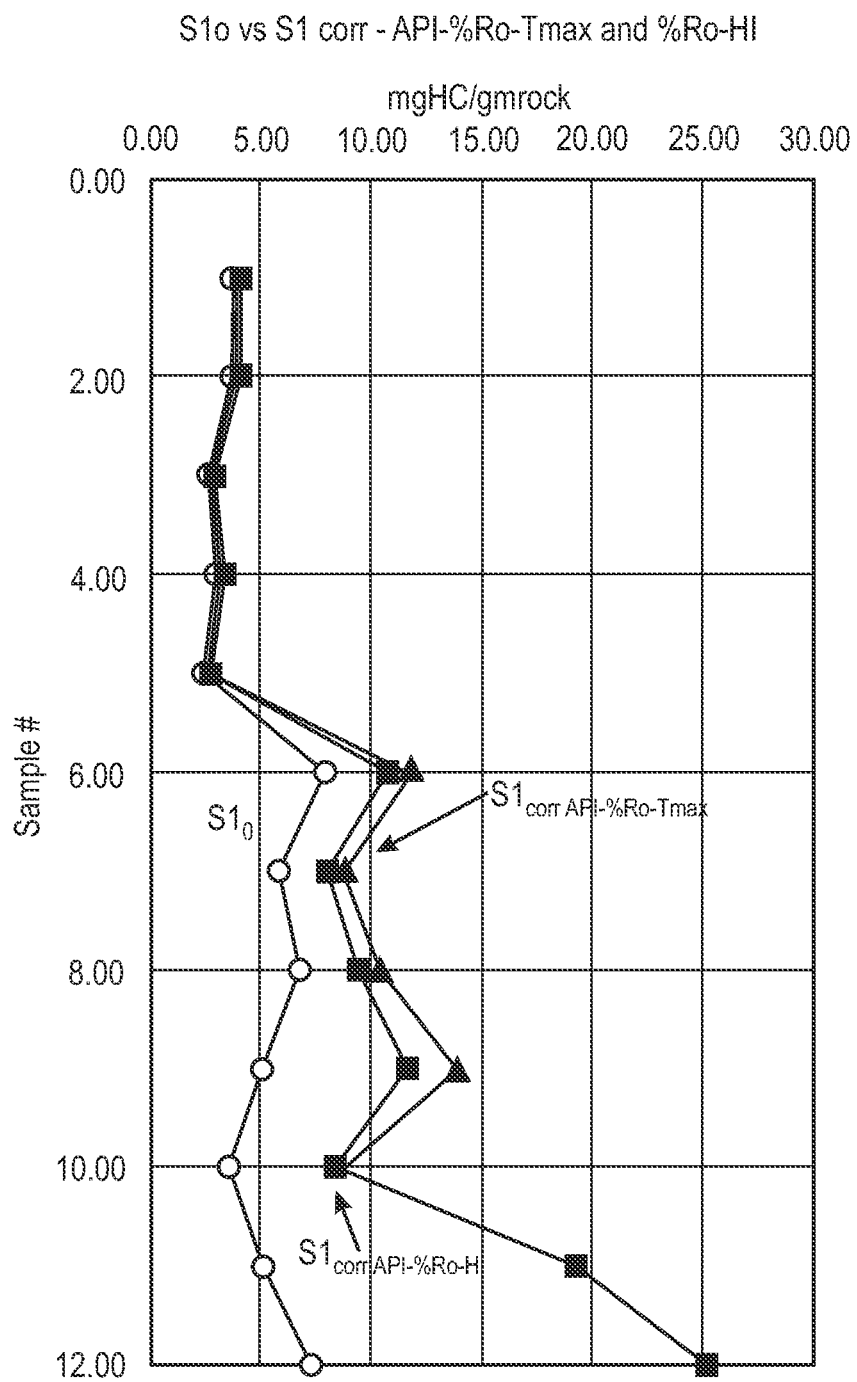

This then is used to adjust and correct the S1 accordingly for the loss of these fractions according to the following equation:

$$S1_{corr} = S1_o/(1-(\% \text{ Loss}/100)) \quad (7)$$

Where $S1_{corr}$ represents the value of the corrected S1 and $S1_o$ the original S1 and the (% Loss/100) is used to scale the loss value back to a fraction. Thus, when this relationship is used, the value of S1 via the % loss calculated can be corrected as defined by either the calculated API or a known API which can be supplied if needed. FIGS. 5A-5C plot the API with % loss computed that was used to correct the S1 value due to volatility related to maturity and hydrocarbon potential. Referring to the maturity in FIGS. 3A-3C as a reference for evaluating FIGS. 5A-5C, the samples 1-5 that have the lowest maturity and also lowest API, also have minimal loss compared to those at peak maturity and finally those that are of condensate maturity which have the greatest loss. With this correction, hydrocarbons in place can be determined according to the density of the fluids, and with this corrected fluid volume the hydrocarbons in place can then be determined.

To determine hydrocarbons in place via barrels per acre-foot, it is desirable to know the bulk density of the rock. The assay of fluid volumes is not computed according to porosity because S1 represents the volume of fluid via mg HC/gm rock that would be contained within the pores created during maturity due to intra-kerogen porosity. Therefore, the estimate of hydrocarbons in place is based on what should be in place based on the transformation of the generative potential of the organic matter into hydrocarbons that should be present currently based on the corrected S0 1 value. The assay disclosed herein contains a mineral to element calculator that can compute the bulk density given input from results from X-ray diffraction. This is shown in FIGS. 6A and 6B. The wt % kerogen used is the total organic carbon (TOC) value that is provided by pyrolysis. Bulk density is calculated as $p_b = p_g (1-\emptyset) + p_{fl} (\emptyset)$, where $p_b$=bulk density, $p_g$ is the grain density, $p_{fl}$ the fluid density and $\emptyset$ is the porosity. The grain density can be computed as $p_g = \Sigma (M_i * p_{g\ i})$ where $M_i$ is the weight fraction and $p_{g\ i}$ the grain density of each mineral. A normalized adjusted value for each mineral and TOC as wt % is computed as Scaled Mineralogy with TOC=$(M_i/(\Sigma M_i + M_j))*100\%)$ where $M_i$=minerals $M_j$=TOC.

Thus, with the known fluid densities computed from API and the bulk densities and unit conversion factors, estimates of the hydrocarbons in place per interval can be computed as follows (FIGS. 6A and 6B):

$$\text{Barrels/acre-foot} = S1_{corrected}(\text{mgHC/gm rck}) \times 1 \text{ gm}/1000 \text{ mg} \times p_b (\text{gm/cc})/p_f \quad (8) \quad (\text{gm/cc})/100^\wedge 3/.159 \text{ m}^3 \times 100^\wedge 3 \times 1233.5 \text{ m}^3$$

Where $p_b$ is the bulk density and the $p_r$ is hydrocarbon fluid density computed from API and .159 m$^3$=1 barrel and 1233.5 m$^3$=1 acre-foot (Hunt, 1979). The hydrocarbon fluid density can be computed as $p_f=141.1/(\text{API}+131.5)$.

Figure 7A:
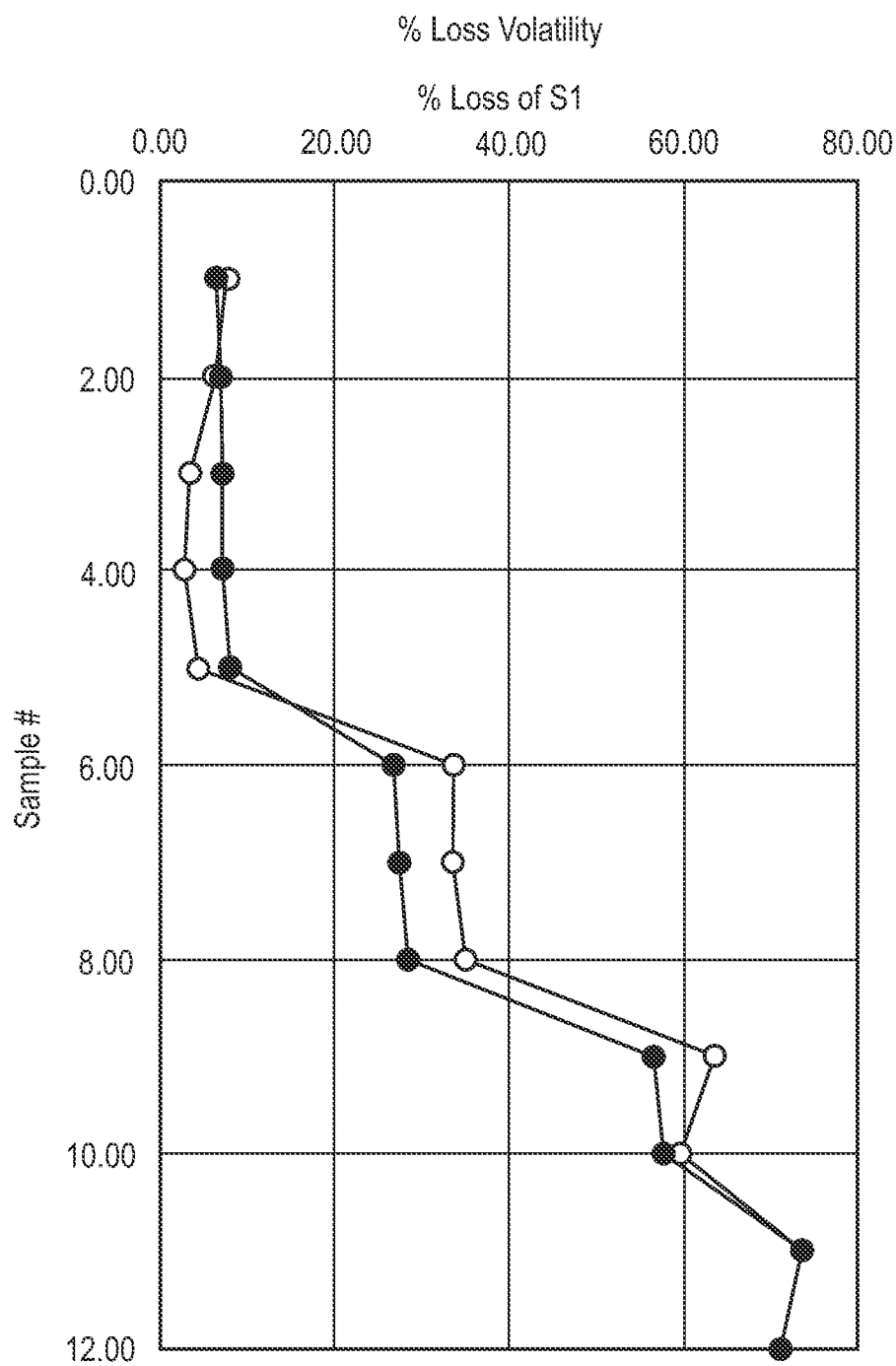
FIGS. 7A-7C are plots of the computed loss due to volatility (A), the corresponding S1 correction (B) and the computed hydrocarbons in place (C).
Figure 7B:
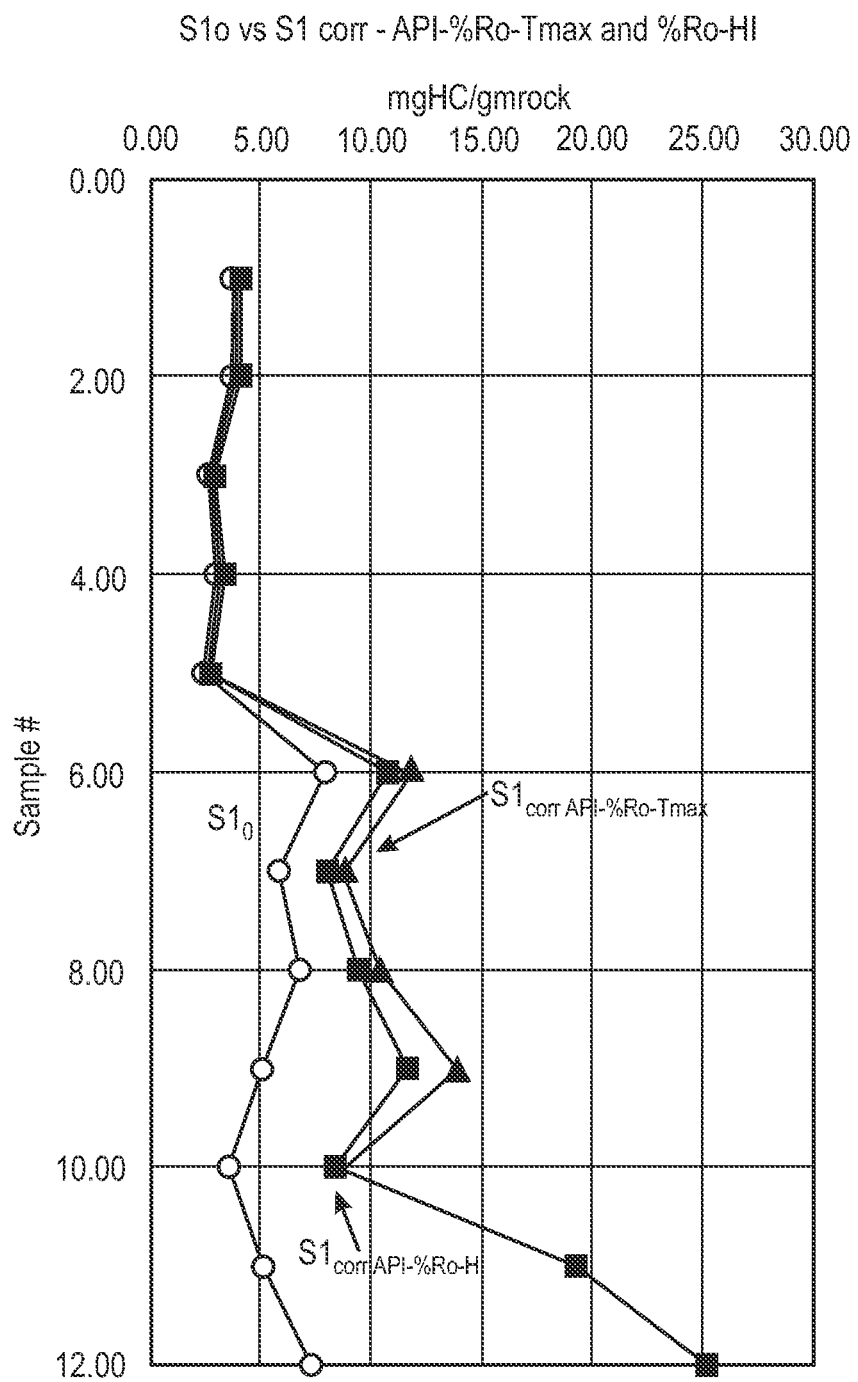
Figure 7C:
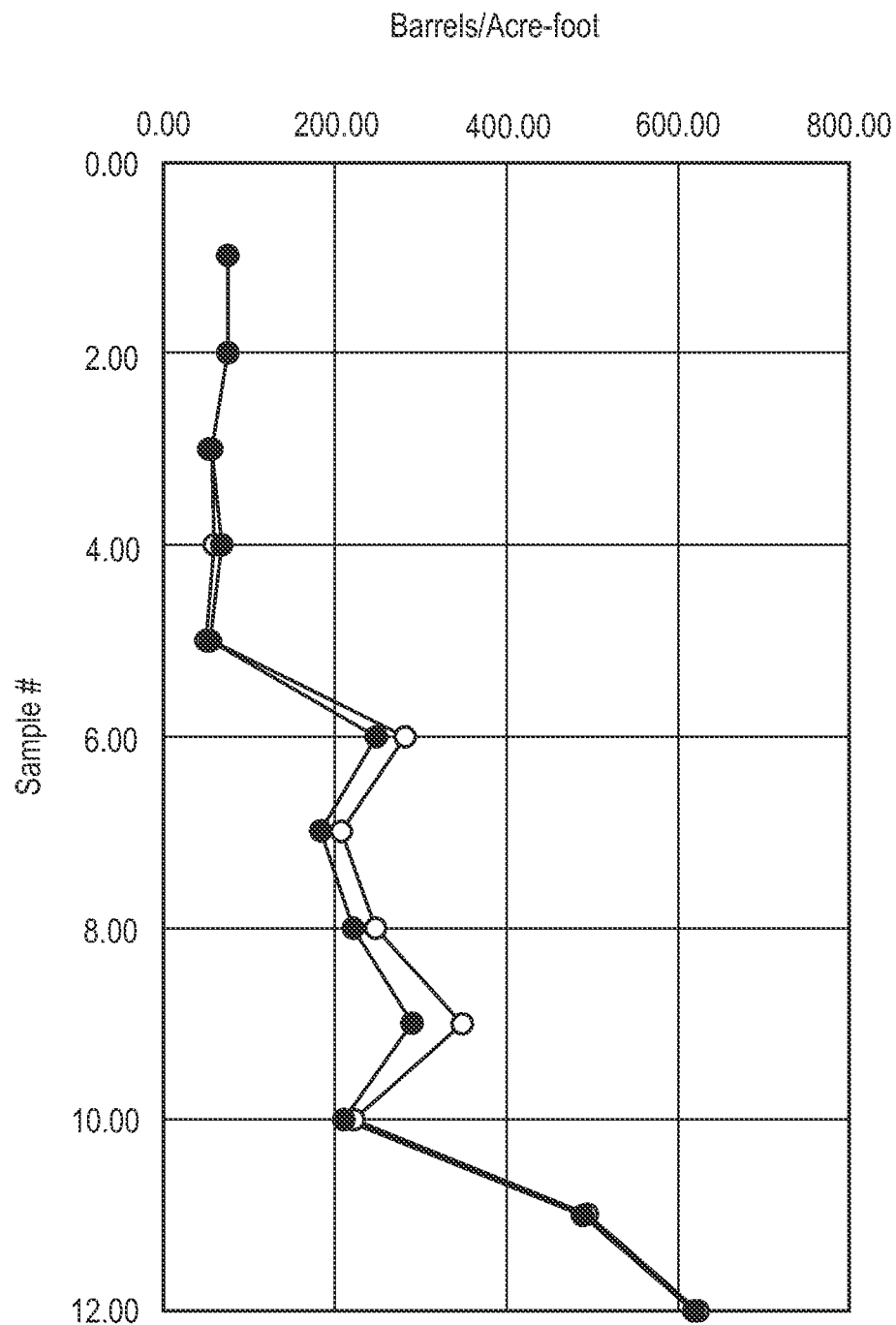

FIGS. 7A-7C shows the computed loss due to volatility, the corresponding S1 correction and the computed hydrocarbons in place. As can be seen, the hydrocarbons in place steadily increase with increasing maturity and the intervals having the highest maturity have the largest volume of hydrocarbons, near 600 barrels per acre foot because their generative potential has been converted into hydrocarbons. This value does not represent the total volume of what was generated because a significant amount of hydrocarbon was expelled during initial generation. This value represents the remainder still in the rock after generation and expulsion, which represents the estimated hydrocarbon in the source rock reservoir. The percentage of that which would be producible would be constrained by the porosities and permeabilities and pressures of the reservoir.

Accompanying that increase in hydrocarbon volume is also an increase in intra-kerogen porosity. The assay disclosed herein predicts intra-kerogen porosity using the HI via a transform that was developed. The transform accounts for both changes in density and development of porosity at the same time in reference to the H/C ratio as measured and defined by the aromaticity measured using solid state nuclear magnetic resonance. That pore volume relative to the H/C is presented. That data also coupled with the known densities of the kerogen analyzed were used to develop the relationship as follows:

$$\% \text{ Intra-kerogen porosity} = 7.4748 \text{ (HI)}^{-0.739} \times 100 \quad (9)$$

Figure 8:
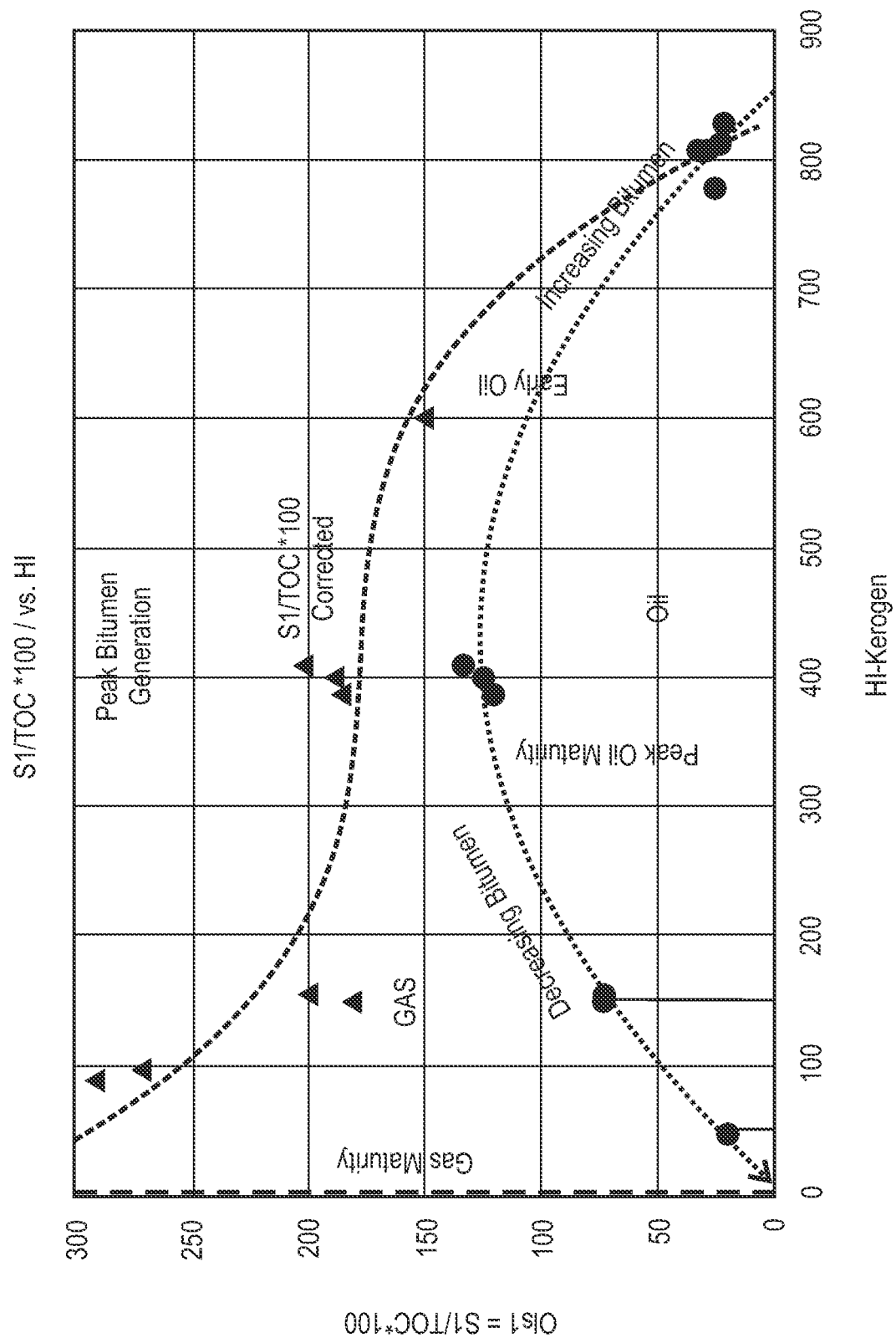
FIG. 8 is a plot showing the distribution of the original bitumen as S1 relative to TOC in reference to HI.

Now intra-kerogen porosity typically will start to increase in the rock as gas oil ratio increases due to oil to gas cracking. The corrected S1 not only provides a way to compute the hydrocarbons in place, but also offers the potential to compute a gas oil ratio. With the assumption that the S1 restored was the fraction that escaped from the rock, the bulk of which was gas or highly volatile hydrocarbons, the corrected value, can be subtracted from the initial S1 value, assuming that it represents oil, to compute a gas oil ratio. This is visualized in FIG. 8 via a plot of the corrected S1 value as a ratio of the TOC similar to the oil index described earlier. Note the corrected value is minimal at 800 HI and then increases gradually through to early oil and then to peak oil and afterward increases rather abruptly after late oil into gas maturity. The trend follows a third order polynomial fit similar to that of a transformation ratio.

Figure 9A:
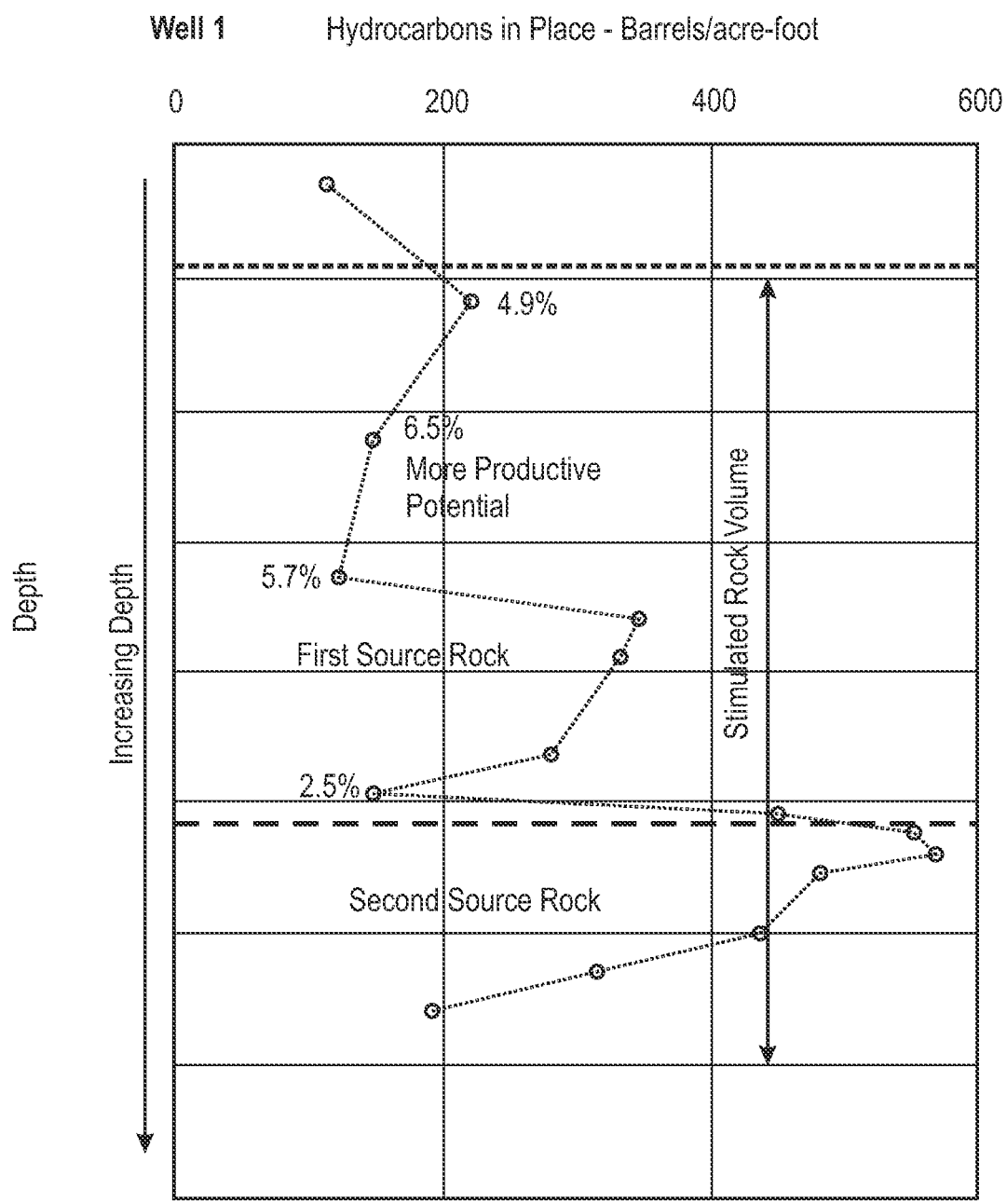
FIGS. 9A and 9B are plots showing computation of Hydrocarbons in Place versus depth for two wells.
Figure 9B:
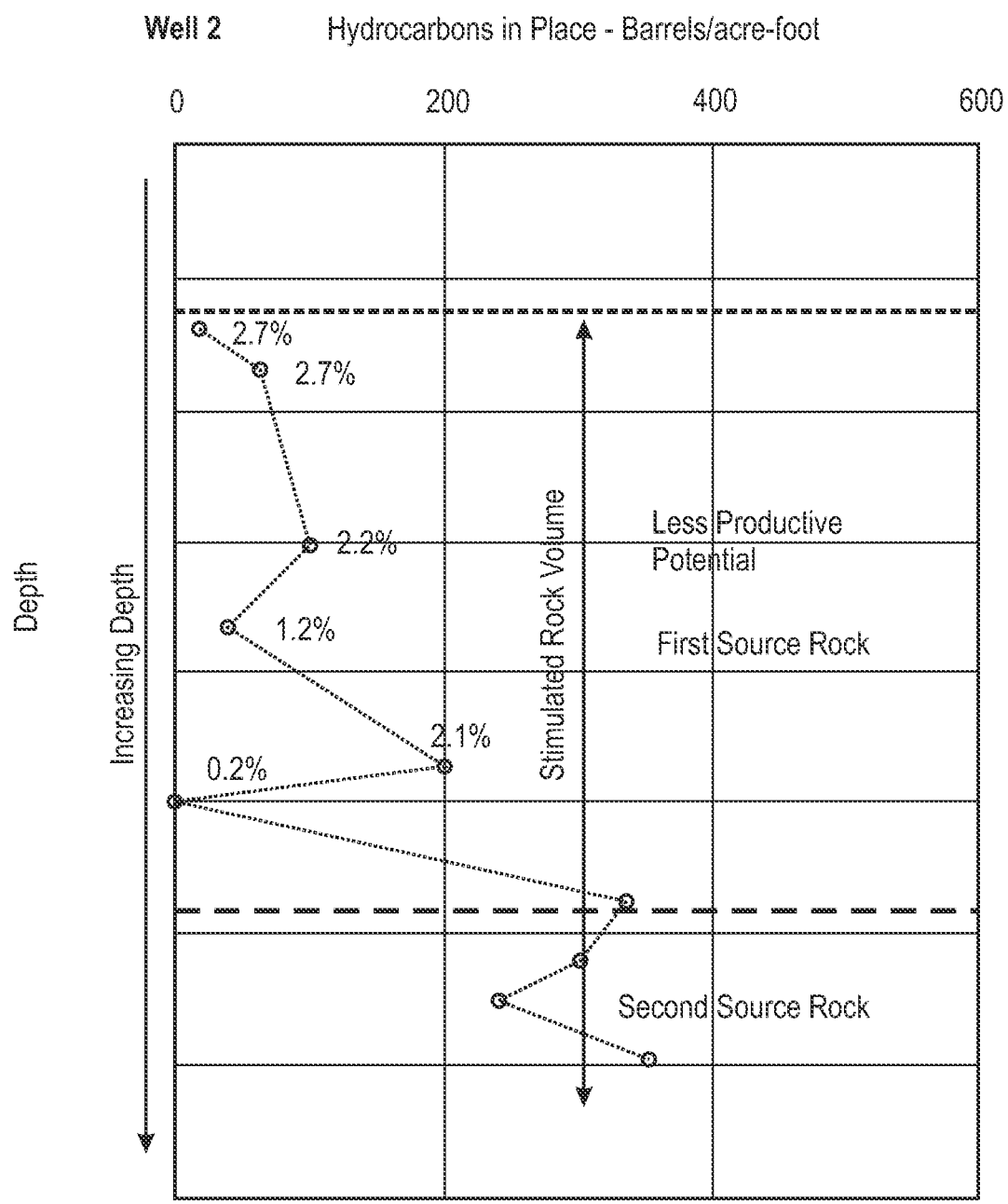

The trend also shows that as the kerogen enters later maturities, the S1 value increases significantly in the rock in the reservoir relative to the TOC, but at the same time it is observed to be declining in the rock analyzed, showing the rock is losing that component generated due to volatility driven by its changing gas and fluid properties (FIGS. 9A and 9B). Therefore, as soon as the rock reaches the surface that component of S1 is lost and therefore can be considered a gas. Thus, since a barrel of oil is equivalent to 3200 ft$^3$ of gas on a chemical basis (Hunt, 1979) the following equation has been developed to compute the gas-oil ratio for the samples:

$$\text{Gas/Oil (Ft}^3/\text{barrel}) = ((S1corr - S1o)/1000/pf \text{ (gm/cc)}/ 100^\wedge 3/0.159 \text{ m}^3 * 3200 \text{ ft}^3))/((S1o \text{ mgHC/gm rck}/1000/\text{ pf (gm/cc)}/100^\wedge 3/0.159)) \quad (10)$$

Figure 10A:
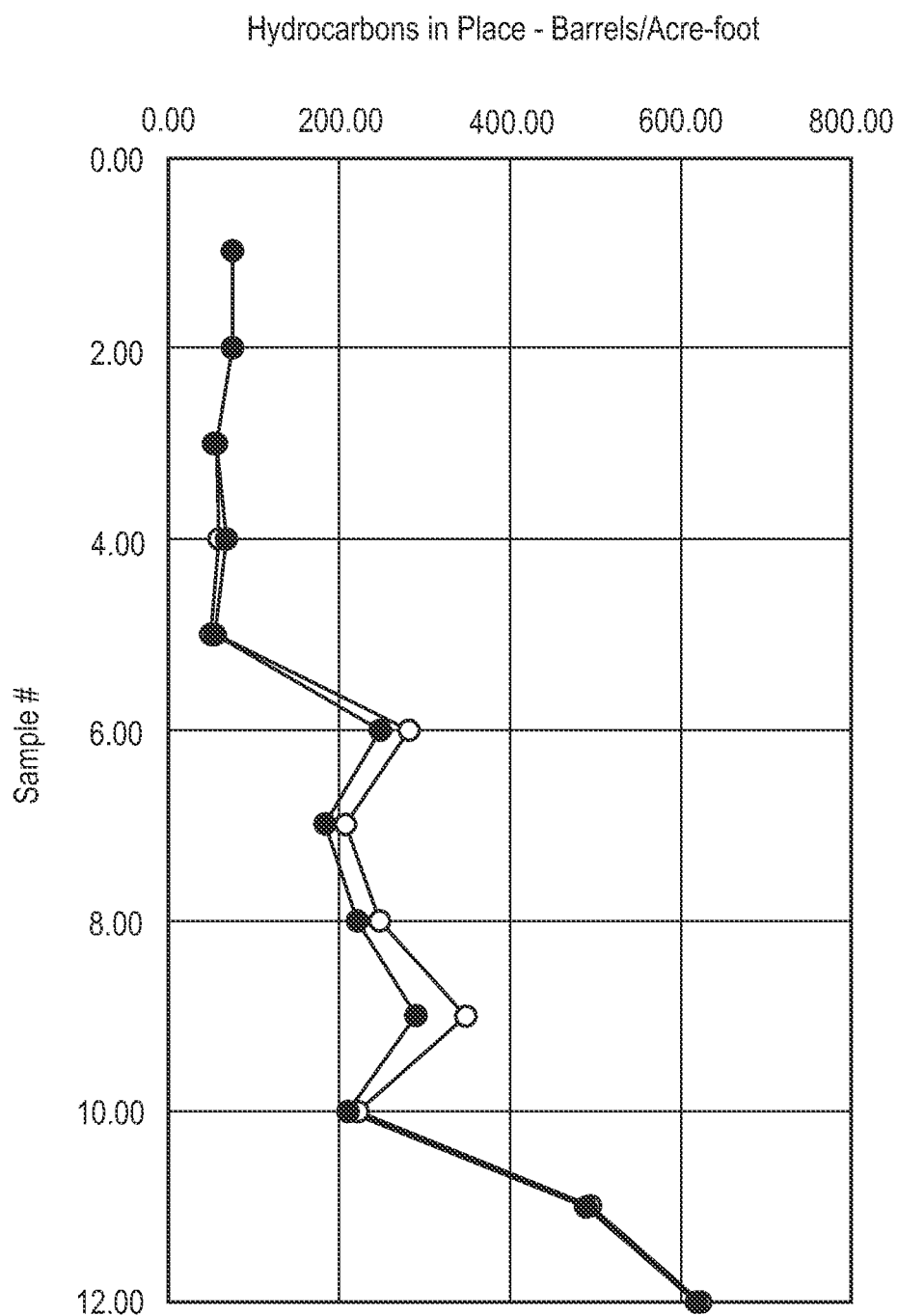
FIGS. 10A-10C are plots of the hydrocarbons in place (A), the intra-kerogen porosity (B) and the computed gas-oil ratio (C).
Figure 10B:
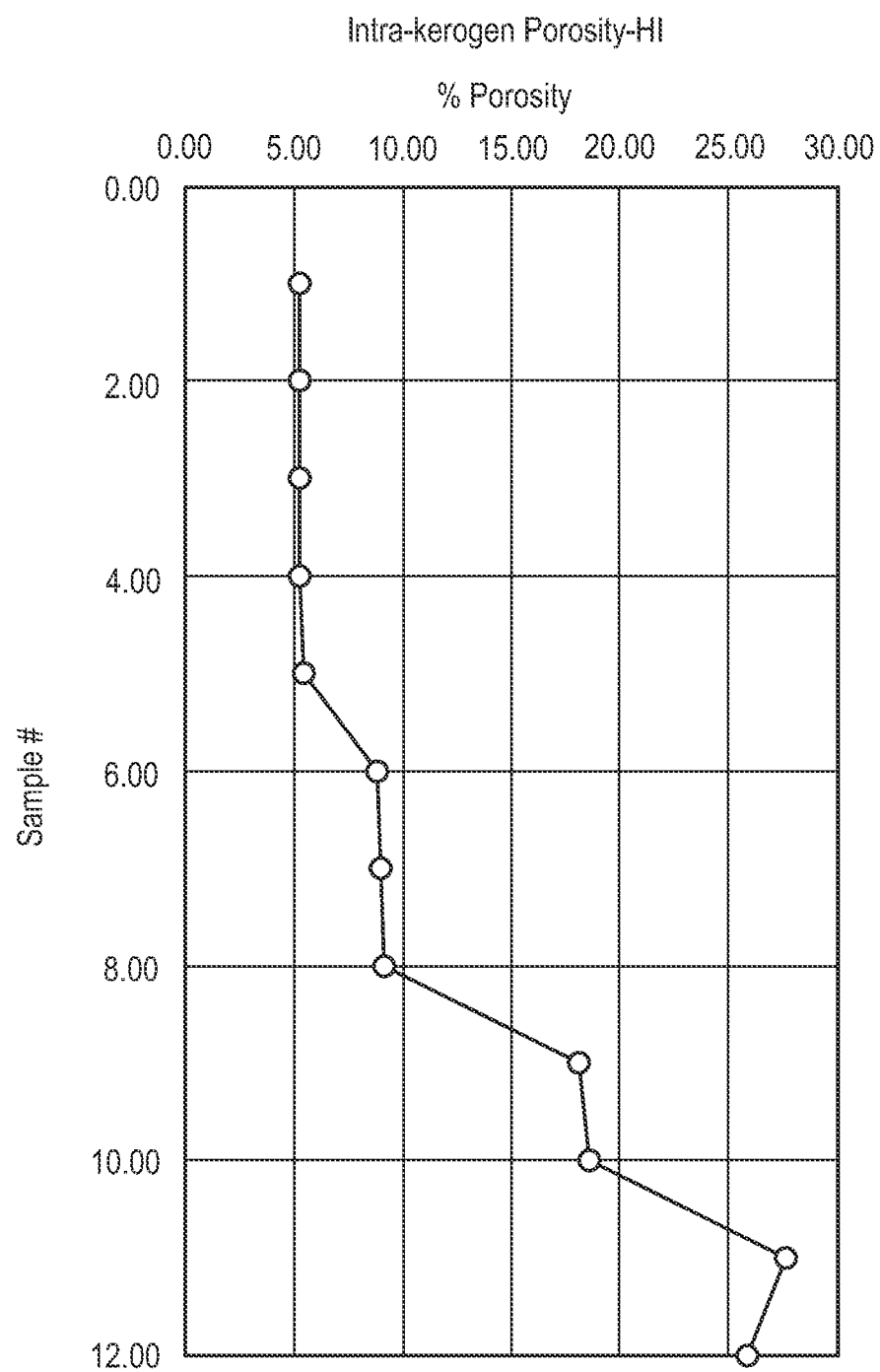
Figure 10C:
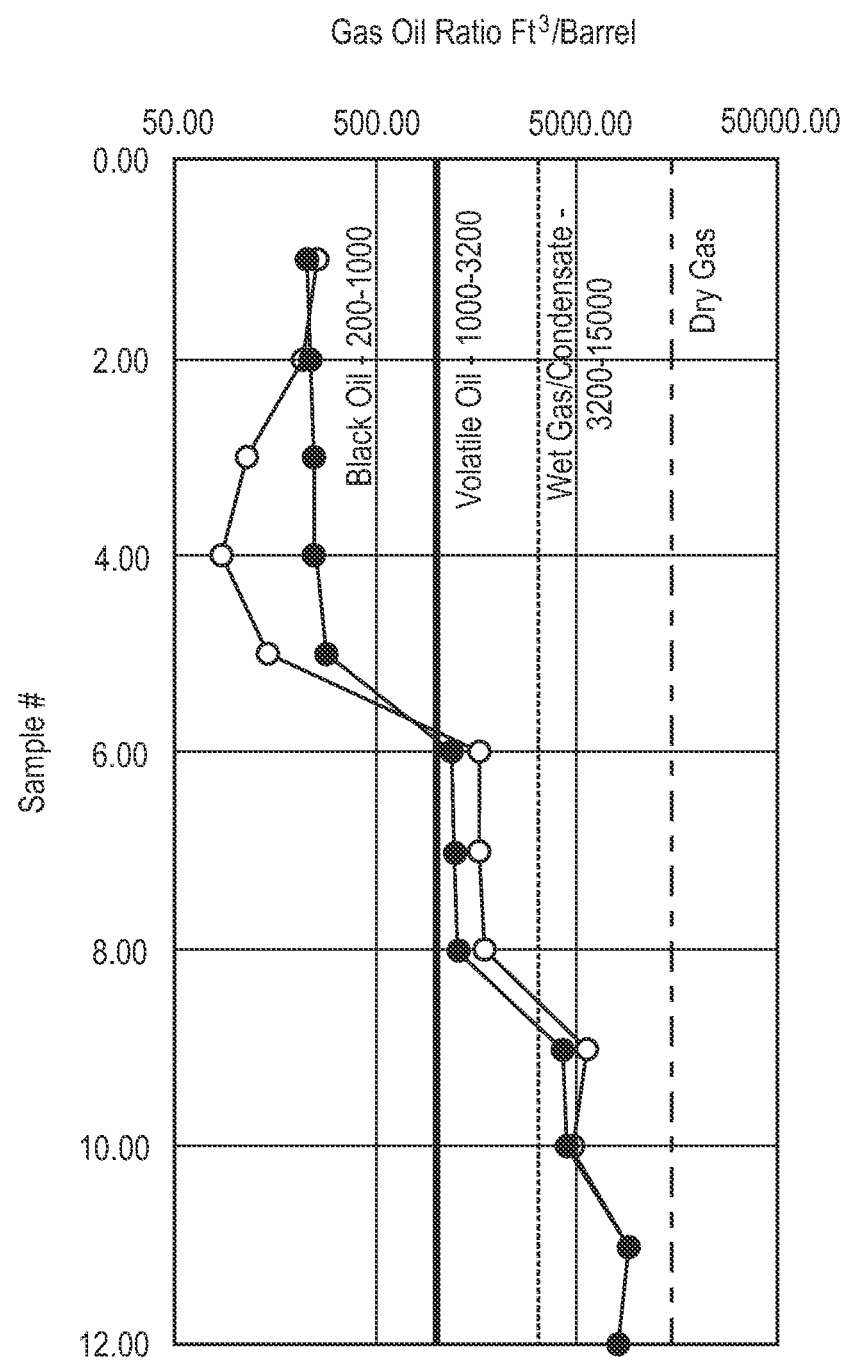

The hydrocarbons in place computed earlier are compared to the computation of the gas/oil ratio and kerogen porosity in FIGS. 10A-10C. Parameters computed from T-max are white those from HI are black. The gas oil ratio predicted is in line with the maturity established earlier.

Figure 11:
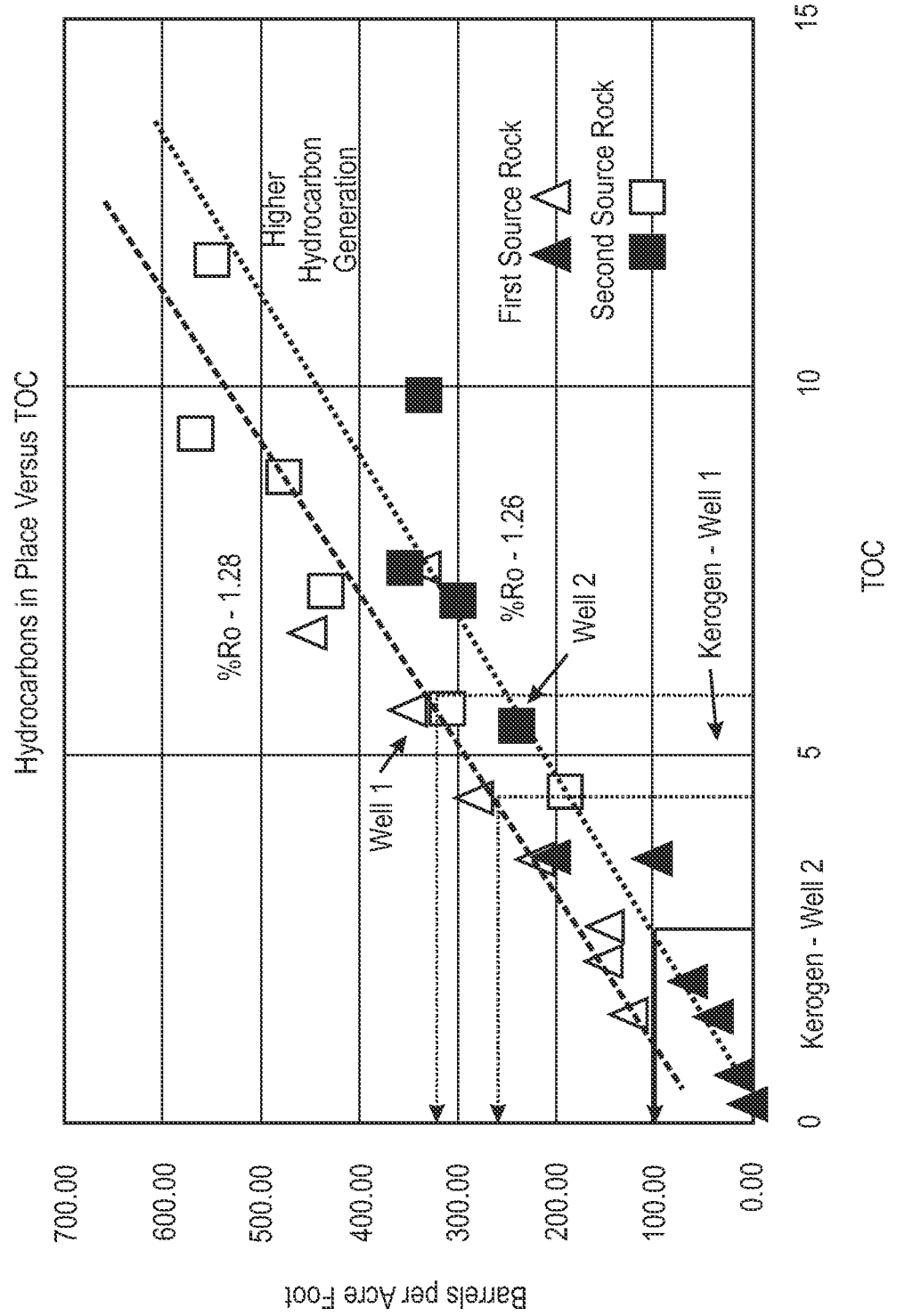
FIG. 11 is a plot showing the hydrocarbon in place for two wells computed from as described in the disclosure compared to TOC.
Figure 12A:
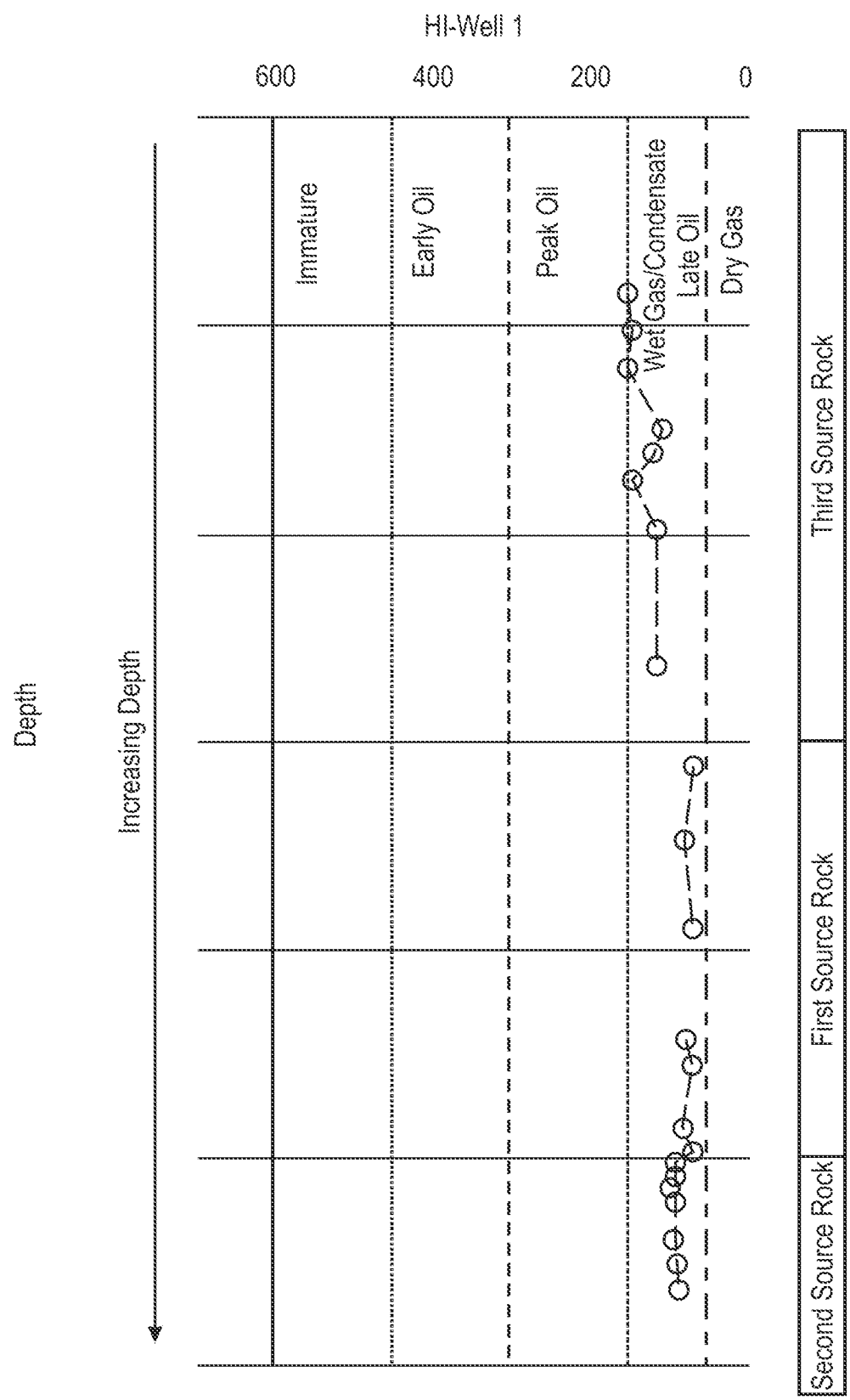
FIGS. 12A-12C are plots showing hydrogen index, maturity and corresponding API density, respectively.
Figure 12B:
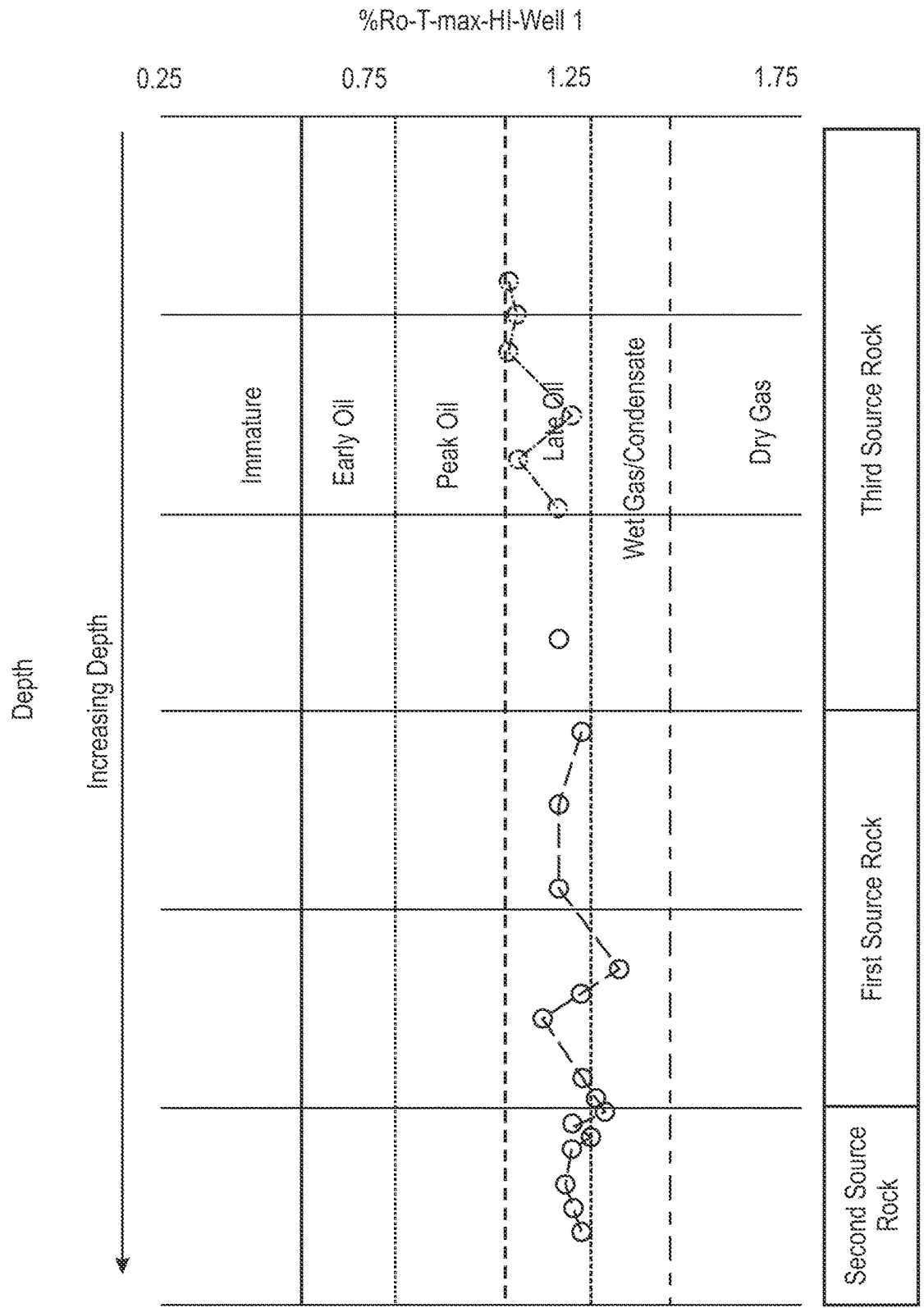
Figure 12C:
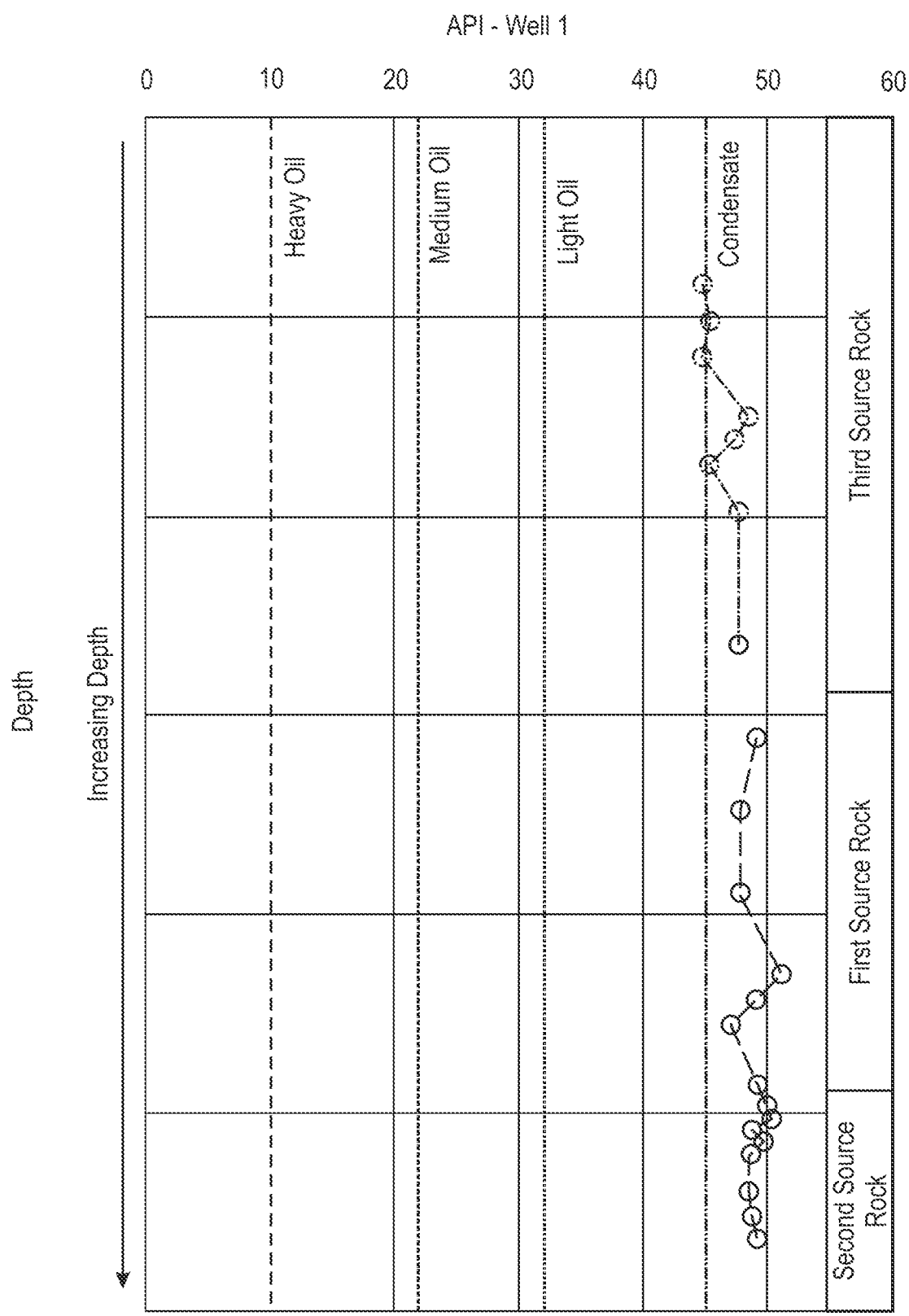
Figure 13A:
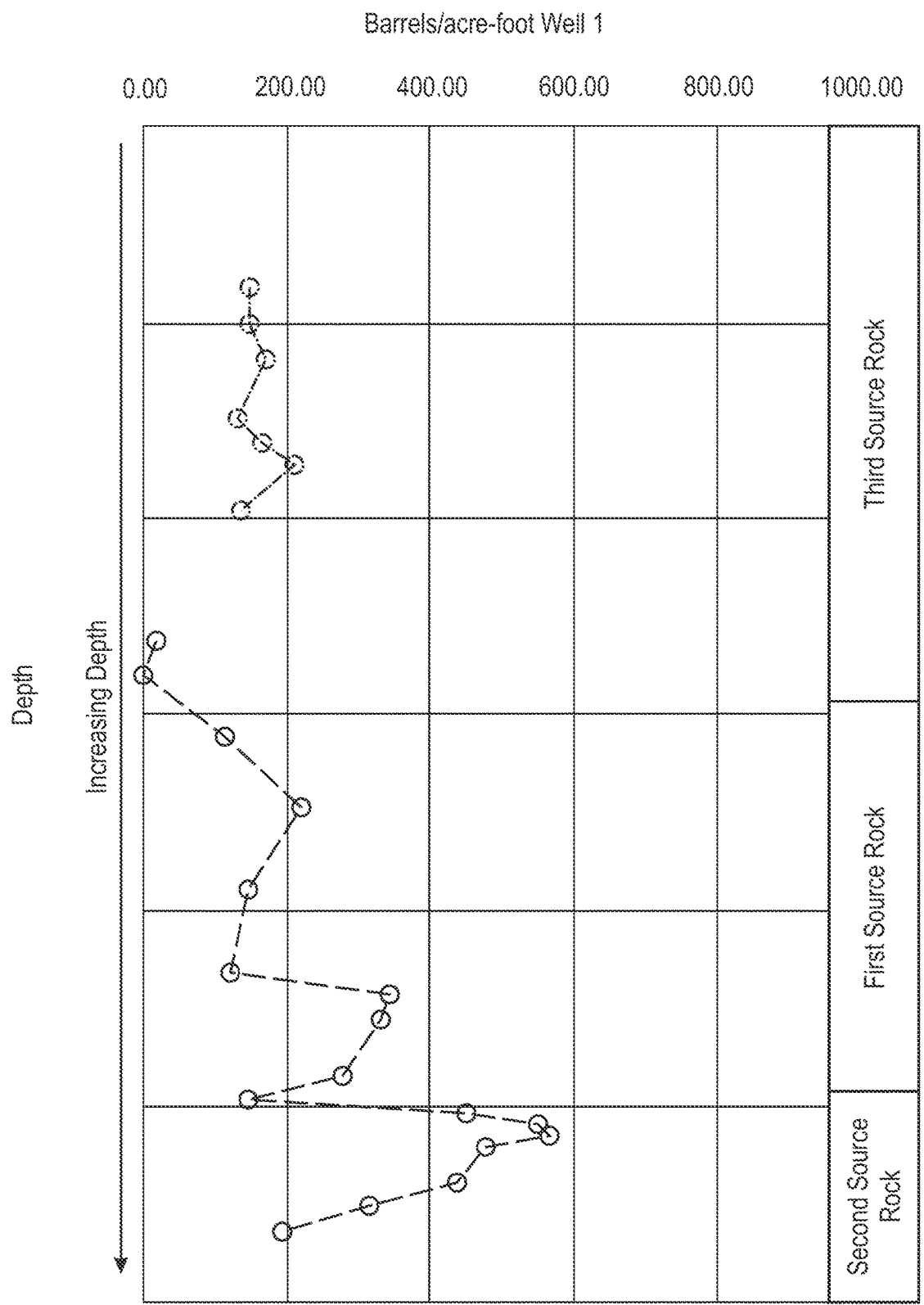
FIGS. 13A-13C are plots of hydrocarbons in place, the gas oil ratio predicted for those fluids, and the intrakerogen porosity available for their recovery, respectively.
Figure 13B:
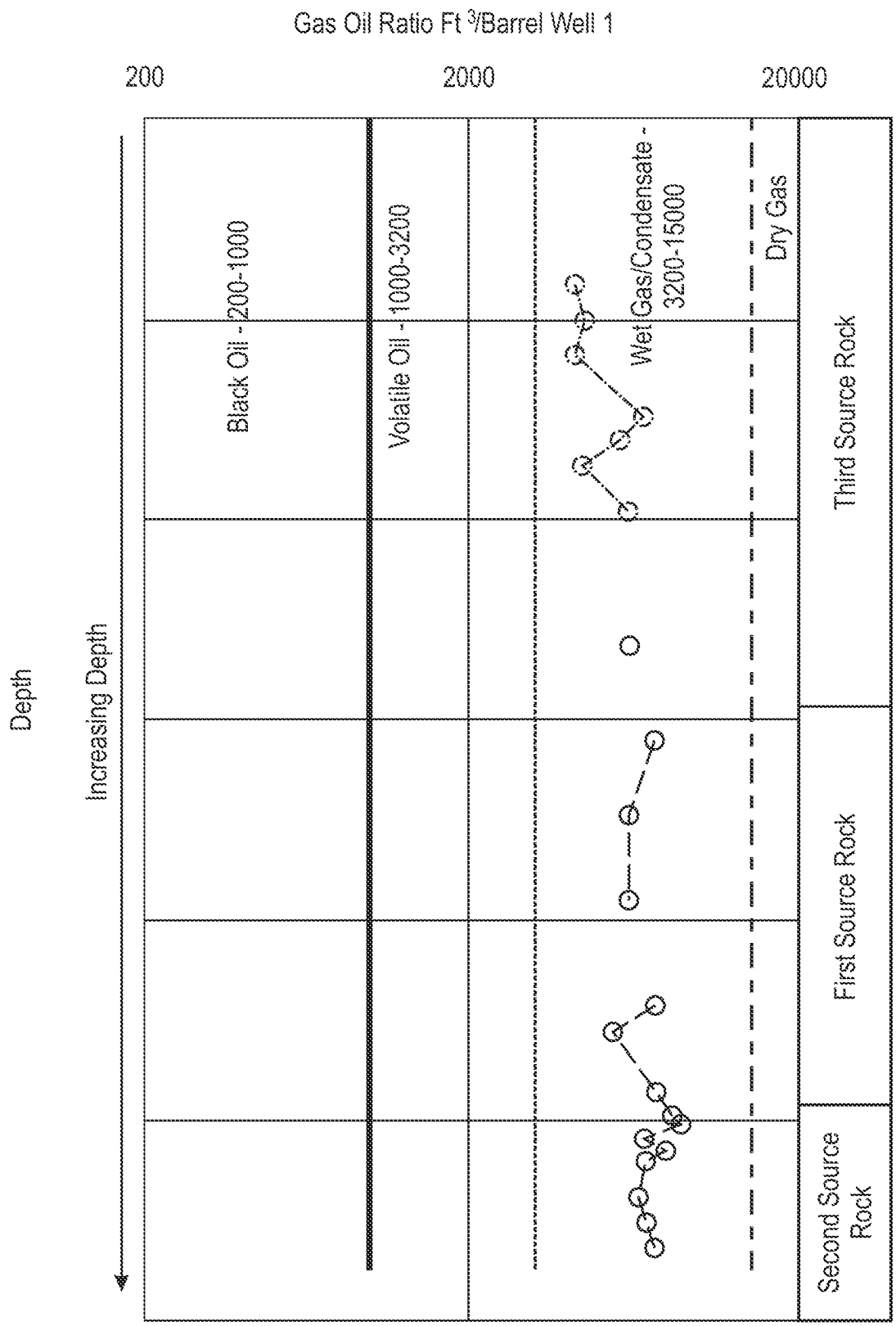
Figure 13C:
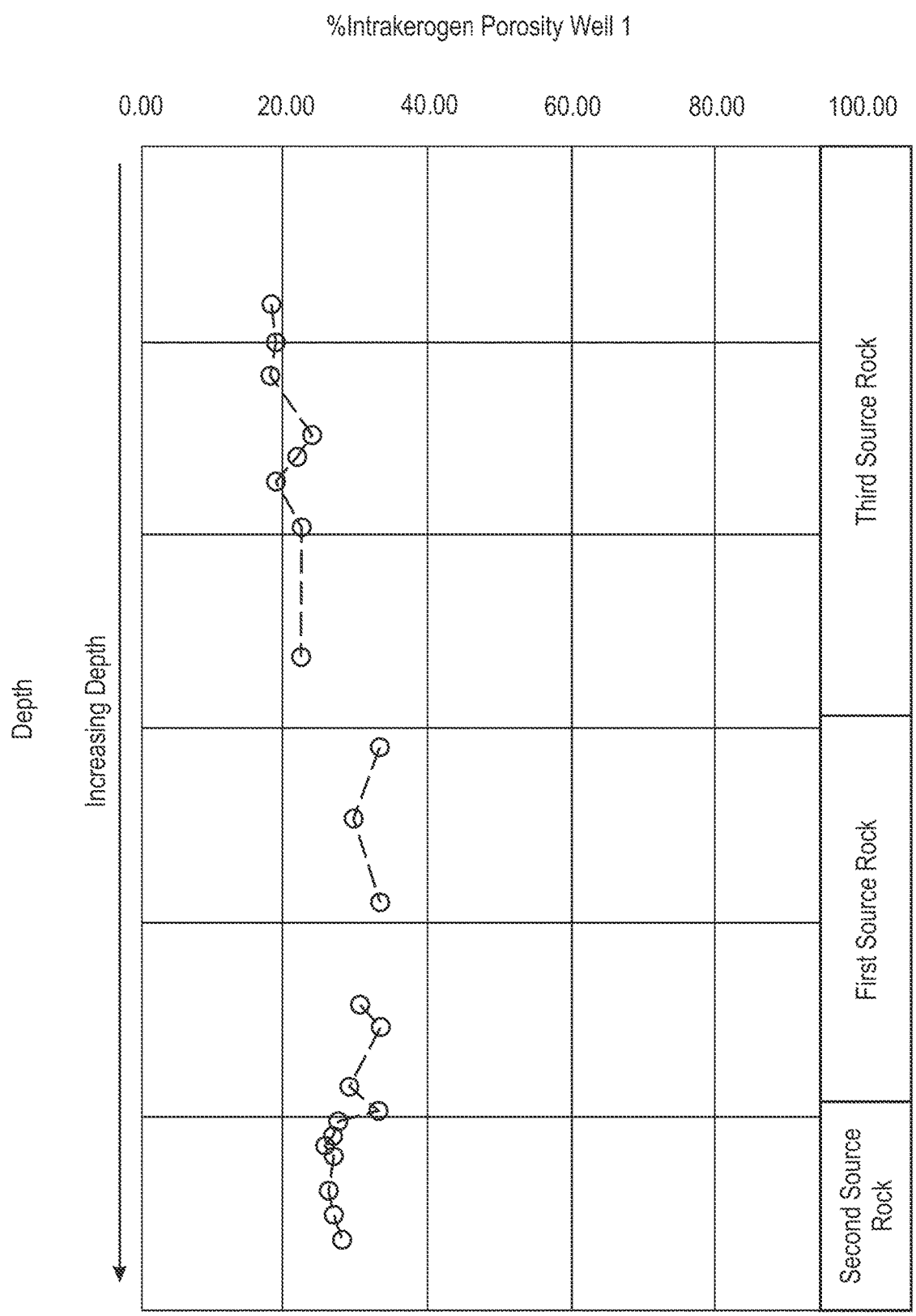

With the assay disclosed herein, a regional assessment can be made of the potential fluid properties of source rock reservoirs distributed across a basin which can be used for improving exploration for exploiting more favorable drilling targets than others, to improve recovery. All of these properties can be mapped out across a region using ARC-GIS mapping software that can be superimposed on basin model predictions about other properties. Also, the application of the assay for predicting the hydrocarbons in place along the vertical strata of individual wells can be used to predict the reservoirs properties of the potential stimulated rock volume thereby improving potential well fracking strategies. FIG. 11 shows the hydrocarbon in place for two wells computed with the assay compared to TOC. This demonstrates that though the same source rock reservoirs have a similar maturity, their difference in the potential hydrocarbons that could be recovered are different even when their TOC is similar. FIG. 9 shows the computation of hydrocarbons in place vs. depth for two wells. This demonstrates that when the data are plotted according to depth from which it originated, an architecture emerges about the stimulated rock volume and potential hydrocarbons that can be recovered from each of these wells. It can be seen that Well 1 has a more potential for recovering hydrocarbons than Well 2. After the potential well is completed, the assay provides a full assessment of the fluid properties and potential intra-kerogen porosity that provides insight into the potential success of that recovery as well. FIGS. 12A-12C respectively show hydrogen index, maturity and corresponding API density predicted for the stimulated rock volume. FIGS. 13A-13C respectively show hydrocarbons in place, the gas oil ratio predicted for those fluids, and the intra-kerogen porosity available for their recovery. Solid circles are values calculated from HI, dashed circles are values calculated from T-max.

Figure 14:
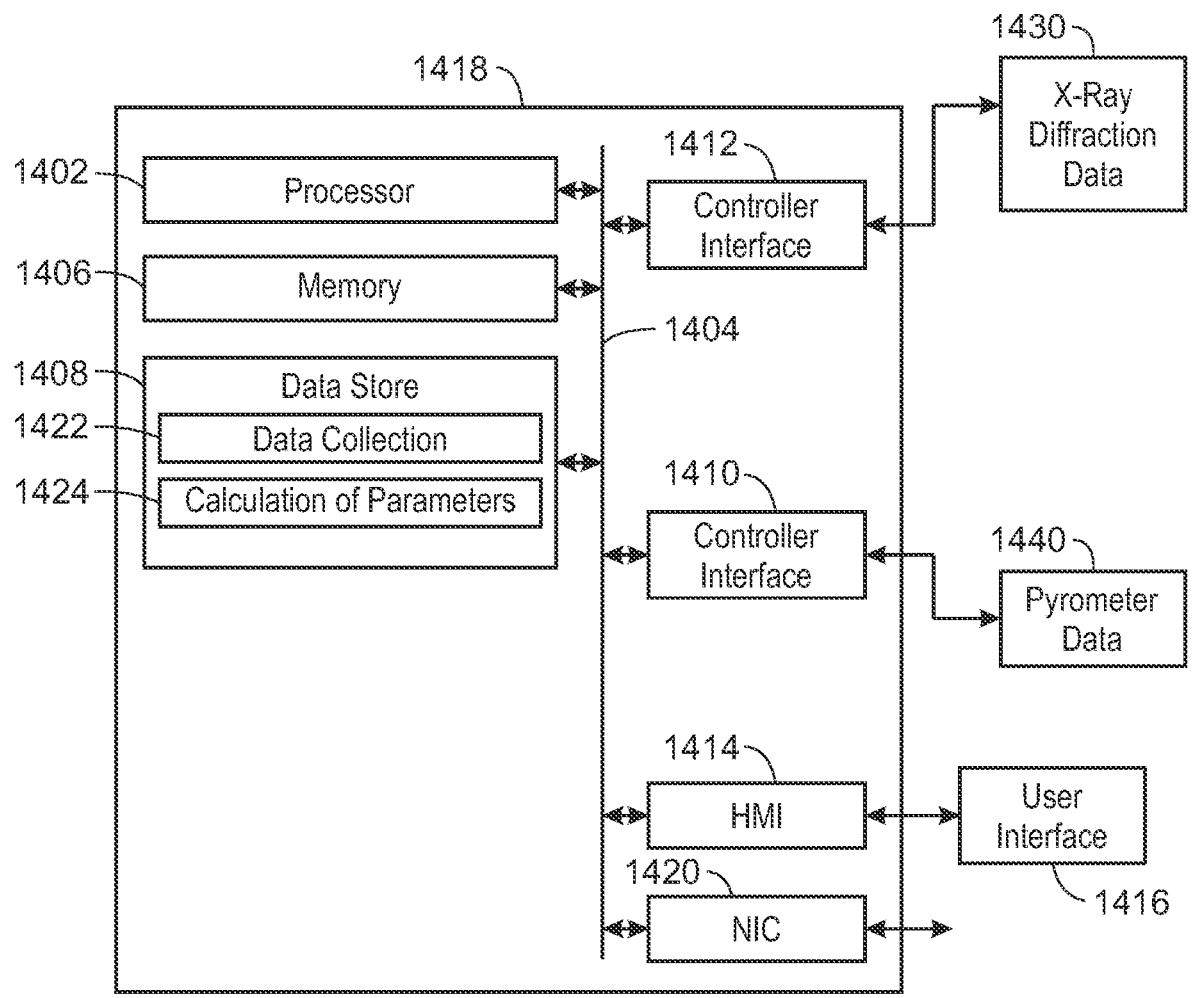
FIG. 14 is a block diagram of the describing a system for performing the assay.

FIG. 14 is a block diagram of a controller 1400 for controlling the assay disclosed herein. The controller 1400 may be used to provide more robust process control and higher efficiency.

In some embodiments, the controller 1400 may be a separate unit mounted in the field or plant, such as a programmable logic controller (PLC), for example, as part of a supervisory control and data acquisition (SCADA) or Fieldbus network. In certain embodiments, the controller 1400 may interface to a distributed control system (DCS) installed in a central control center. In some embodiments, the controller 1400 may be a virtual controller running on a processor in a DCS, on a virtual processor in a cloud server, or using other real or virtual processors.

The controller 1400 includes a processor 1402. The processor 1402 may be a microprocessor, a multi-core processor, a multithreaded processor, an ultra-low-voltage processor, an embedded processor, or a virtual processor. The processor 1402 may be part of a system-on-a-chip (SoC) in which the processor 1402 and other components are formed into a single integrated package. In various embodiments, the processor 1402 may include processors from Intel® Corporation of Santa Clara, California, from Advanced Micro Devices, Inc. (AMD) of Sunnyvale, California, or from ARM holdings, LTD., of Cambridge England. Any number of other processors from other suppliers may also be used.

The processor 1402 may communicate with other components of the controller 1400 over a bus 1404. The bus 1404 may include any number of technologies, such as industry standard architecture (ISA), extended ISA (EISA), peripheral component interconnect (PCI), peripheral component interconnect extended (PCIx), PCI express (PCIe), or any number of other technologies. The bus 1404 may be a proprietary bus, for example, used in an SoC based system. Other bus technologies may be used, in addition to, or instead of, the technologies above. For example, plant interface systems may include I2C buses, serial peripheral interface (SPI) buses, Fieldbus, and the like.

The bus 1404 may couple the processor 1402 to a memory 1406. In some embodiments, such as in PLCs and other process control units, the memory 1406 is integrated with a data store 1408 used for long-term storage of programs and data. The memory 1406 include any number of volatile and nonvolatile memory devices, such as volatile random-access memory (RAM), static random-access memory (SRAM), flash memory, and the like. In smaller devices, such as PLCs, the memory 1406 may include registers associated with the processor itself. The data store 1408 is used for the persistent storage of information, such as data, applications, operating systems, and so forth. The data store 1408 may be a nonvolatile RAM, a solid-state disk drive, or a flash drive, among others. In some embodiments, the data store 1408 will include a hard disk drive, such as a micro hard disk drive, a regular hard disk drive, or an array of hard disk drives, for example, associated with a DCS or a cloud server.

The bus 1404 couples the controller 1400 to a controller interface 1410. The controller interface 1410 may be an interface to a plant bus, such as a Fieldbus, an I2C bus, an SPI bus, and the like. The controller interface 1410 couples the controller 1400 to a pyrometer 1440.

A controller interface 1412 couples the controller 1400 to an X-ray diffractometer 1430. The interface 1412 may be an interface to a plant bus, such as a Fieldbus, an I2C bus, an SPI bus, and the like.

If the controller 1400 is located in the field, a local human machine interface (HMI) 1414 may be used to input control parameters. The local HMI 1414 may be coupled to a user interface 1416, including, for example, a display that includes a multiline LCD display, or a display screen, among others. The user interface 1416 may also include a keypad for the entry of control parameters, such as the starting parameters for the flow of the lean solvent into the contactor. Generally, the controller 1400 will either be part of a plant control system, such as a DCS, or coupled through a plant bus system to the plant control system.

In some embodiments, the controller 1400 is linked to a control system for the assay through a network interface controller (NIC) 1420. The NIC 1420 can be an Ethernet interface, a wireless network interface, or a plant bus interface, such as Fieldbus.

The data store 1408 includes blocks of stored instructions that, when executed, direct the processor 1402 to implement the control functions for the assay. The data store 1408 includes a block 1422 of instructions to direct the processor to collect data through the interface 1412.

The data store 1408 also includes a block 1424 of instructions to direct the processor to calculate one or more parameters from data received from the X-ray diffractometer and/or a pyrometer 1440. Any number of blocks may be included in the data store 1408 to implement of the various functions and/or steps of the assay disclosed herein. Such blocks can be used individually or in combination as appropriate.

What is claimed is:

1. A method, comprising:
    performing pyrolysis on a source rock, wherein performing pyrolysis on the source rock comprises heating the source rock in an oven;
    obtaining pyrolysis data on the source rock based on performing pyrolysis on the source rock;
    determining a hydrocarbon generative potential (S2) of kerogen in the source rock from the pyrolysis data;
    determining a total organic carbon (TOC) content (in weight %) of the source rock from the pyrolysis data;
    determining a maturity of the reservoir (% Ro) from S2 and TOC;

determining a ratio of an oil specific gravity of the source rock to a density of the source rock (API) using the equation $API = Ln(\% Ro/0.2534)/.0345;$ obtaining x-ray diffraction (XRD) data for the source rock; and determining an additional parameter from the pyrolysis data, the X-ray diffraction (XRD) data, or both.

2. The method of claim 1, wherein determining the additional parameter comprises determining a gas/oil ratio.

3. The method of claim 1, wherein determining the additional parameter comprises determining a productivity of the source rock.

4. The method of claim 1, further comprising determining a ratio of saturated fluids to aromatic fluids in the source rock (Sat/Aro) using the equation $Sat/Aro = (\% Ro/.7842)^{(1/.3571)}$ 5. The method of claim 1, further comprising determining a percent loss of a $C_{15+}$ fraction (% Loss n–$C_{15+}$) of bitumen of the source rock using the equation % Loss n–$C_{15+}$ = $API/7.2379^{(1/.4508)}$.

6. The method of claim 5, further comprising determining a corrected milligrams of distillable hydrocarbon of the source rock per gram of the source rock ($S1_{corr}$) using the equation $S1_{corr} = S1_o/(1 - (\% \text{Loss } n-C_{15+}/100))$, wherein $S1_o$ is an original value of the milligrams of distillable hydrocarbon of the source rock per gram of the source rock.

7. The method of claim 1, further comprising determining a percent loss of a $C_{15+}$ fraction (% Loss n–$C_{15+}$) of bitumen of the source rock using the equation % Loss n–$C_{15+}$ = $API/7.2379^{(1/.4508)}$.

8. The method of claim 7, further comprising determining a corrected milligrams of distillable hydrocarbon of the source rock per gram of the source rock ($S1_{corr}$) using the equation $S1_{corr} = S1_o/(1 - (\% \text{Loss } n-C_{15+}/100))$, wherein $S1_o$ is an original value of the milligrams of distillable hydrocarbon of the source rock per gram of the source rock as measured by pyrolysis.

9. The method of claim 1, further comprising determining a ratio of saturated fluids to aromatic fluids in the source rock (Sat/Aro) using the equation $Sat/Aro = (\% Ro/.7842)^{(1/.3571)}$, wherein % Ro is a maturity of the source rock.

10. The method of claim 1, wherein determining the additional parameter comprises determining hydrocarbons in place in the source rock.

11. A method of evaluating a source rock, the method comprising:
 performing pyrolysis on the source rock, wherein performing pyrolysis on the source rock comprises heating the source rock in an oven;
 obtaining pyrolysis data for the source rock based on performing pyrolysis on the source rock;
 determining a hydrocarbon generative potential (S2) of kerogen in the source rock from the pyrolysis data;
 determining a total organic carbon (TOC) content (in weight %) of the source rock from the pyrolysis data;
 determining a maturity of the reservoir (% Ro) from S2 and TOC; and
 determining a ratio of an oil specific gravity of the source rock to a density of the source rock (API) using the equation $API = Ln(\% Ro/0.2534)/.0345,$ wherein % Ro is a maturity of the source rock.

12. The method of claim 11, further comprising determining a ratio of saturated fluids to aromatic fluids in the source rock (Sat/Aro) using the equation $Sat/Aro = (\% Ro/.7842)^{(1/.3571)}$.

13. The method of claim 11, further comprising determining a percent loss of a $C_{15+}$ fraction (% Loss n–$C_{15+}$) of bitumen of the source rock using the equation % Loss n–$C_{15+}$ = $API/7.2379^{(1/.4508)}$.

14. The method of claim 13, further comprising determining a corrected milligrams of distillable hydrocarbon of the source rock per gram of the source rock ($S1_{corr}$) using the equation $S1_{corr} = S1_o/(1 - (\% \text{Loss } n-C_{15+}/100))$, wherein $S1_o$ is an original value of the milligrams of distillable hydrocarbon of the source rock per gram of the source rock and (% Loss n–$C_{15+}$/100) scales the loss value to a fraction.

15. A method of evaluating a source rock, the method comprising:
 performing pyrolysis on the source rock, wherein performing pyrolysis on the source rock comprises heating the source rock in an oven;
 obtaining pyrolysis data for the source rock based on performing pyrolysis on the source rock;
 determining a hydrocarbon generative potential (S2) of kerogen in the source rock from the pyrolysis data;
 determining a total organic carbon (TOC) content (in weight %) of the source rock from the pyrolysis data;
 determining a maturity of the reservoir (% Ro) from S2 and TOC; and
 determining a ratio of saturated fluids to aromatic fluids in the source rock (Sat/Aro) using the equation $Sat/Aro = (\% Ro/.7842)^{(1/.3571)}$.

16. A method of evaluating a source rock, the method comprising:
 performing pyrolysis on the source rock, wherein performing pyrolysis on the source rock comprises heating the source rock in an oven;
 obtaining pyrolysis data for the source rock based on performing pyrolysis on the source rock;
 determining a hydrocarbon generative potential (S2) of kerogen in the source rock from the pyrolysis data;
 determining a total organic carbon (TOC) content (in weight %) of the source rock from the pyrolysis data;
 determining a maturity of the reservoir (% Ro) from S2 and TOC;
 determining a ratio of an oil specific gravity of the source rock to a density of the source rock (API) using the equation $API = Ln(\% Ro/0.2534)/.0345;$ and determining a percent loss of a $C_{15+}$ fraction (% Loss n–$C_{15+}$) of bitumen of the source rock using the equation % Loss n–$C_{15+}$ = $API/7.2379^{(1/.4508)}$.

17. A method of evaluating a source rock, the method comprising:

performing pyrolysis on the source rock, wherein performing pyrolysis on the source rock comprises heating the source rock in an oven;

obtaining pyrolysis data for the source rock based on performing pyrolysis on the source rock;

determining a distillable hydrocarbon (S1) of kerogen in the source rock from the pyrolysis data;

determining a total organic carbon (TOC) content (in weight %) of the source rock from the pyrolysis data; and determining a corrected milligrams of distillable hydrocarbon of the source rock per gram of the source rock ($S1_{corr}$) using the equation $$S1_{corr} = S1_o/(1-(\% \text{ Loss n-}C_{15+}/100)),$$

wherein $S1_o$ is an original value of the milligrams of distillable hydrocarbon of the source rock per gram of the source rock and % Loss n–$C_{15+}$ is a percent loss of a C15+ fraction of bitumen of the source rock.

* * * * *